United States Patent [19]

Watanabe et al.

[11] Patent Number: 5,145,502
[45] Date of Patent: Sep. 8, 1992

[54] SUBSTITUTED BENZOYL DERIVATIVES AND HERBICIDAL COMPOSITIONS

[75] Inventors: Junichi Watanabe; Yasuo Kondo, both of Funabashi; Masataka Hatanaka, Shiraoka; Takashi Ikai, Shiraoka; Koichi Suzuki, Shiraoka; Tsutomu Nawamaki, Shiraoka; Shigeomi Watanabe, Shiraoka, all of Japan

[73] Assignee: Nissan Chemical Industries Ltd., Tokyo, Japan

[21] Appl. No.: 640,808

[22] Filed: Jan. 14, 1991

Related U.S. Application Data

[62] Division of Ser. No. 460,631, Feb. 8, 1991.

[51] Int. Cl.$^5$ ............................................. A01N 43/02
[52] U.S. Cl. ............................................ 71/90; 71/91
[58] Field of Search ...................... 549/64; 71/90, 91

[56] References Cited

U.S. PATENT DOCUMENTS 5,034,049 7/1991 Kober .................................. 549/64

OTHER PUBLICATIONS

Rossy, "Aromatization . . . ", J. Org. Chem, 45(4) 617–20, 1980.
Konosu, "Synthesis . . . " Chem. Pharm. Bull, 38 (5) 1258–1265, 1990.

*Primary Examiner*—Alan L. Rotman
*Assistant Examiner*—Catherine Scalzo
*Attorney, Agent, or Firm*—Oblon, Spivak, McClelland, Maier & Neustadt

[57] ABSTRACT

A substituted benzoyl derivative of the formula:

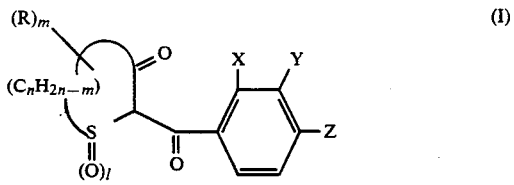

ps wherein
R is a lower alkyl group, or a phenyl group unsubstituted or substituted by a lower alkyl group, halogen atom or a lower alkoxy group;
n is an integer of 2 Or 3;
m is an integer of from 0 to 6, and when m is an integer of from 2 to 6, the plurality of R may be the same or different fron one another;
l is an integer of 0, 1 or 2;
X is a halogen atom, a nitro group, a cyano group, a lower alkyl group, a lower alkoxy group, or a lower haloalkyl group;
Y is a hydrogen atom, a halogen atom, a nitro group, a lower alkyl group unsubstituted or substituted by a halogen atom or a lower alkoxy group, a lower alkoxy group, or a lower alkoxy carbonyl group; and
Z is a halogen atom, a nitro group, a cyano group, a trifluoromethyl group, a lower alkoxy group, a lower alkylthio group, a lower haloalkylthio group, a lower alkylsulfinyl group, a lower haloalkylsulfinyl group, a lower alkylsulfonyl group, or a lower haloalkylsulfonyl group.

6 Claims, No Drawings

SUBSTITUTED BENZOYL DERIVATIVES AND HERBICIDAL COMPOSITIONS

This application is a divisional of Ser. No. 460,631, filed Feb. 8, 1991.

BACKGROUND OF THE INVENTION

Field of the Invention

The present invention relates to novel substituted benzoyl derivatives, processes for their production and herbicidal compositions containing them.

Discussion of Background

As a result of extensive researches over years, the present inventors have found that the compounds of the present invention have herbicidal activities remarkably high as compared with conventional herbicides, and many of the compounds of the present invention have excellent selectivity for certain crop plants, particularly for gramineous crop plants such as corn and wheat, and thus are practically useful. The present invention has been accomplished on the basis of these discoveries.

Namely, the compounds of the present invention are so effective that the dose of the active ingredient per unit area can substantially be reduced as compared with conventional herbicidal compounds, and their phytotoxicity against crop plants is extremely low as compared with conventional herbicides. Therefore, their economical effects are substantial. Further, with the compounds of the present invention, it is possible to substantially reduce a danger of environmental pollution due to application of agricultural chemicals in large amounts, and little adverse effects to other crop plants due to the effects remaining in soil are observed. Therefore, the compounds of the present invention may be regarded as epoch-making herbicides.

SUMMARY OF THE INVENTION

The present invention provides a substituted benzoyl derivative of the formula:

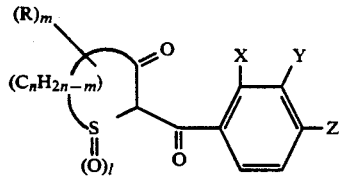
(I)

wherein
- R is a lower alkyl group, or a phenyl group unsubstituted or substituted by a lower alkyl group, halogen atom or a lower alkoxy group;
- n is an integer of 2 or 3;
- m is an integer of from 0 to 6, and when m is an integer of from 2 to 6, the plurality of R may be the same or different from one another;
- l is an integer of 0, 1 or 2;
- X is a halogen atom, a nitro group, a cyano group, a lower alkyl group, a lower alkoxy group, or a lower haloalkyl group;
- Y is a hydrogen atom, a halogen atom, a nitro group, a lower alkyl group unsubstituted or substituted by a halogen atom or a lower alkoxy group, a lower alkoxy group, or a lower alkoxy carbonyl group; and
- Z is a halogen atom, a nitro group, a cyano group, a trifluoromethyl group, a lower alkoxy group, a lower alkylthio group, a lower haloalkylthio group, a lower alkylsulfinyl group, a lower haloalkylsulfinyl group, a lower alkylsulfonyl group, or a lower haloalkylsulfonyl group.

The present invention also provides a herbicidal composition comprising a herbicidally effective amount of the substituted benzoyl derivative of the formula I and an agricultural carrier or diluent.

Now, the present invention will be described in detail with reference to the preferred embodiments.

The compound of the present invention is a novel compound not disclosed in literatures and has excellent physiological activities as a herbicide.

The compound of the present invention takes the following three structures by tautomerism;

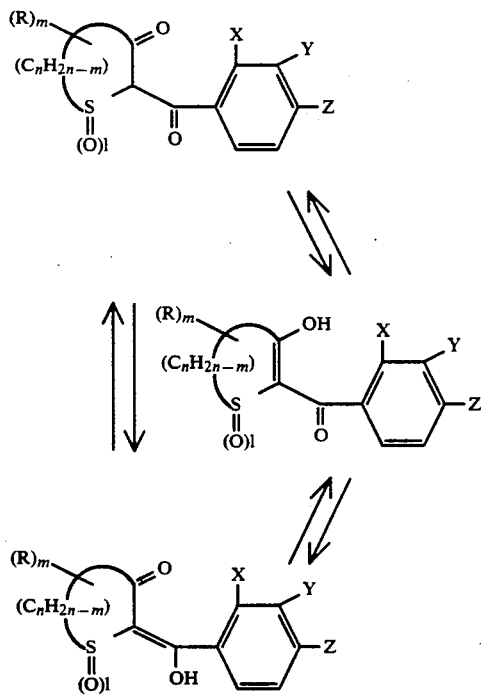

In the above formulas, R, n, m, l, X, Y and Z are as defined above. The compound of the formula I of the present invention can easily be produced by the following reaction.

Reaction scheme

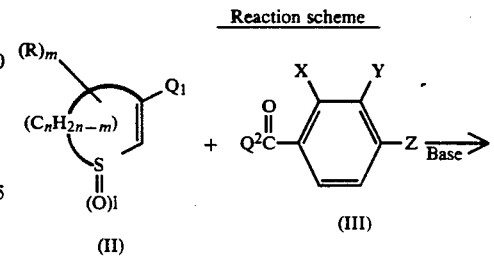

-continued
Reaction scheme

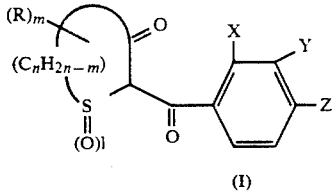

In the above formulas, $Q^1$ is $-N(CH_3)_2$, $-N(CH_2CH_3)_2$,

$Q^2$ is a halogen atom, and R, n, m, l, X, Y and Z are as defined above.

The compound of the formula II (l=0) can be obtained in good yield in accordance with the reaction disclosed in e.g. Synthesis, p. 368 (1978), J. Amer. Chem. Soc. Vol. 74, p. 1569 (1952). The compound of the formula III can be prepared in accordance with the methods disclosed in e.g. Journal of the Chemical Society, p. 1406 (1934), and the Journal of Organic Chemistry, Vol. 39, p 725 (1974).

The compounds of the formulas II and III are reacted in a suitable solvent, if necessary in the presence of an organic base such as pyridine or triethylamine, whereby the compound of the formula I (l=0) of the present invention can be prepared in good yield. If necessary, the compound of the formula I (l=0) of the present invention is reacted with an oxidizing agent such as m-chloroperbenzoic acid or an aqueous hydrogen peroxide solution to obtain the compound of the formula I (l=1 or 2) of the present invention. Now, the compound of the formula I of the present invention will be described in further detail with reference to Preparation Examples of some representative compounds.

PREPARATION EXAMPLE 1

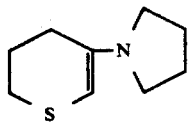

To a solution of 27.6 g of tetrahydrothiopyran-3-one (J. Amer. Chem. Soc. 74, 1569 (1952)) in 300 ml of benzene, 20.3 g of pyrrolidine and 0.5 g of p-toluene sulfonic acid were added, and the mixture was refluxed for five hours by means of a Dean-Stark trap. After cooling the mixture, the solvent was distilled off, and the residue was subjected to distillation under reduced pressure to obtain 36.3 g of a fraction distilled at a temperature of from 98° to 100° C. under 0.3 mmHg (yield 89%). By the $^1$H-NMR analysis, the product was ascertained to be the above identified pyrrolidine enamine.

PREPARATION EXAMPLE 2

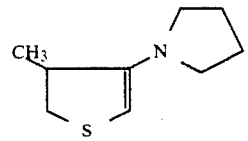

To a solution of 9 g of 4-methyl-3-oxotetrahydrothiophene (Synthesis 368 (1978)) in 80 ml of benzene, 6 g of pyrrolidine and 0.1 g of p-toluenesulfonic acid were added, and the mixture was refluxed for 3 hours by means of a Dean-Stark trap. After cooling the mixture, the solvent was distilled off and the residue was subjected to distillation under reduced pressure to obtain 9.6 g of a fraction distilled at a temperature of from 70° to 85° C. under 0.2 mmHg (yield: 74%). From the $^1$H-NMR analysis, the product was ascertained to be the above identified enamine.

PREPARATION EXAMPLE 3

Compound No. 1 of the Present Invention

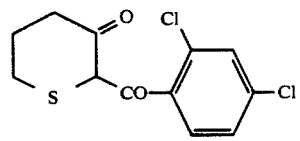

3.8 g (22 mmol) of the enamine obtained in Preparation Example 1 was dissolved in 60 ml of methylene chloride, and 2.45 g (24 mmol) of triethylamine was added thereto. Then, 4.7 g (22 mmol) of 2,4-dichlorobenzoic acid chloride was added thereto, and the mixture was stirred at room temperature overnight. Then, 18 ml of a 2.5N hydrochloric acid aqueous solution was added thereto, and the mixture was stirred for two hours. The reaction solution was extracted with methylene chloride, washed with water and then dried under anhydrous sodium sulfate. After filtration and removal of the solvent by distillation, the product was purified by column chromatography to obtain 3.26 g of a crystal product (melting point: 134°-135° C.). By the $^1$H-NMR and Mass analyses, the product was found to comprise two benzoyl molecules bonded to each other.

1.47 g (3.2 mmol) of the crystal product was dissolved in 10 ml of ethanol, and 10 ml of an aqueous solution having 0.27 g of sodium hydroxide dissolved therein, was added thereto. The mixture was stirred at room temperature overnight. Then, the mixture was acidified with an aqueous hydrochloric acid solution and then extracted with chloroform and dried. After filtration and removal of the solvent by distillation, the product was purified by column chromatography to obtain 0.68 g of a brown liquid. From the $^1$H-NMR and Mass analyses, the product was ascertained to be 2-(2,4-dichlorobenzoyl)-tetrahydrothiopyran-3-one [yield: 74%, brown liquid, refractive index $n_D20$ 1.6288.

$^1$H-NMR δvalue: ((CDCl$_3$)) 2.16((tt, J=6Hz, 6Hz, 2H) 2.60(t, J=6Hz, 2H), 2.73(t, J=6Hz, 2H), 7.13(s, 2H), 7.31(s, 1H)]

PREPARATION EXAMPLE 4

Compound No. 1736 of the Present Invention

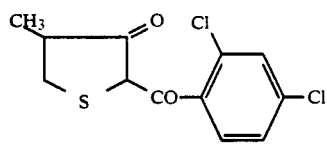

2.5 g (15 mmol) of the enamine obtained in Preparation Example 2 was dissolved in 50 ml of methylene chloride, and 1.65 g (16 mmol) of triethylamine was added thereto. Then, 3.1 g (14 mmol) of 2,4-dichlorobenzoic acid chloride was added thereto, and the mixture was stirred at room temperature overnight. To the reaction solution, 20 ml of a 2.5N hydrochloric acid aqueous solution was added, and the mixture was stirred at room temperature for 4 hours. Then, the mixture was extracted with chloroform, washed with water and dried over anhydrous sodium sulfate. After filtration and removal of the solvent by distillation, the product was purified by column chromatography to obtain 1.57 g of a crystal product. From the $^1$H-NMR and Mass analyses, the product was ascertained to be 2-(2,4-dichlorobenzoyl)-tetrahydrohydrothiophen-3-one.

[Yield: 37%, dark green crystal, melting point: 55°-58° C., $^1$H-NMR δvalue: ((CDCl$_3$)) 1.26–1.37(m, 3H), 2.73–3.28(m,3H), 7.25–7.50(m, 3H), 12.5–13.5(b,1H)]

PREPARATION EXAMPLE 5

Compound No. 32 of the Present Invention

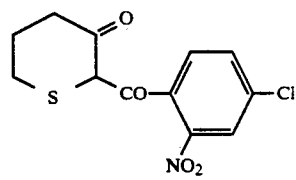

2.5 g (15 mmol) of the enamine obtained in Preparation Example 1 was dissolved in 60 ml of methylene chloride, and then 4.4 g (44 mmol) of triethylamine and 0.05 g of 4-dimethylaminopyridine were added thereto. The mixture was cooled with ice. The, 3.2 g (14 mmol) of 4-chloro-2-nitrobenzoic acid chloride was gradually added thereto. The mixture was stirred at room temperature overnight. To the reaction solution, 20 ml of a 2.5 N hydrochloric acid aqueous solution was added, and the mixture was stirred for further three hours. The mixture was extracted with chloroform, washed with water and dried over anhydrous sodium sulfate. After filtration and removal of the solvent by distillation, the product was purified by column chromatography to obtain 1.38 g of a reddish brown crystal product. From the $^1$H-NMR and Mass analyses, the product was ascertained to be 2-(4-chloro-2-nitrobenzoyl)-tetrahydrothiopyran-3-one.

[Yield: 32%, reddish brown crystal,
melting point: 113°–116° C., $^1$H-NMR δvalue: ((CDCl$_3$)) 2.16((tt, J=6Hz, 6Hz, 2H), 2.61(t, J=6Hz, 2H), 2.72(t, J=6Hz, 2H), 7.34(d, J=8Hz, 1H), 7.71(dd, J=2Hz, J=8Hz, 1H), 8.15(d, J=2Hz, 1H)]

PREPARATION EXAMPLE 6

Compound No. 3 of the Present Invention

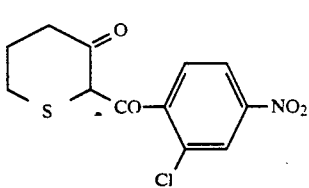

Two g (11.8 mmol) of the enamine obtained in Preparation Example 1 and 3.6 g (3equivalent) of triethylamine were dissolved in dry methylene chloride, and while cooling the mixture in an ice bath, 2.6 (11.8 mmol) of 2-chloro-4-nitrobenzoic acid chloride was dropwise added thereto, and the mixture was stirred at room temperature overnight.

Then, 20 ml of a 2N hydrochloric acid aqueous solution was added thereto, and the mixture was stirred for 3 hours. Then, water was added thereto, and the mixture was extracted with chloroform. The extract was dried over anhydrous sodium sulfate, and chloroform was distilled off under reduced pressure. The product was isolated by column chromatography to obtain 0.35 g (yield: 10%, melting point: 59.2°–62.5° C.) of desired 2-(2-chloro-4-nitrobenzoyl) tetrahydrothiopyran-3-one.

$^1$H-NMR δvalue: ((CDCl$_3$)) 2–3.2 ppm(m, 6H), 7.1–8.5 ppm(m, 3H), 15.2 ppm(br, 1H).

MS: M+=299

Melting point: 59.5°–62.5° C.]

PREPARATION EXAMPLE 7

Compound No. 2 of the Present Invention

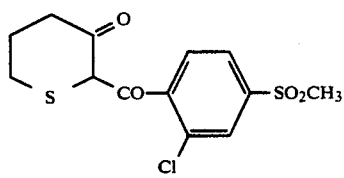

1.33 g (7.9 mmol) of the enamine prepared in Preparation Example 1 and 1.2 g (11.9 mmol) of triethylamine were dissolved in 60 ml of tetrahydrofuran and cooled with ice. Then, 2 g (7.9 mmol) of 2-chloro-4-methylsulfonylbenzoic acid chloride was dissolved in 10 ml of tetrahydrofuran and gradually added to the above solution. The mixture was stirred at room temperature for one hour and then stirred at a temperature of from 60° to 70° C. for two hours. After cooling the mixture, the solvent was distilled off, and 50 ml of chloroform and 20 ml of an aqueous hydrochloric acid solution were added to the residue, and the mixture was stirred at room temperature for one hour. Then, the product was extracted with chloroform, washed with water and dried over anhydrous sodium sulfate. After filtration and removal of the solvent by distillation, the product was purified by column chromatography to obtain 0.32 g of slightly yellow crystal. From the $^1$H-NMR analysis, the product was ascertained to be 2-(2-chloro-4-methylsulfonylbenzoyl)-tetrahydrothiopyran-3-one.

[Yield: 12%, slightly yellow crystal, melting point: 111°–113° C.,

1H-NMR δvalue: ((CDCl3)) 2.22(tt, J=6HZ, 2H), 2.68(t, J=6Hz, 2H), 2.79(t, J=6Hz, 2H), 3.09(s, 3H), 7.51(d, J=8Hz, 1H), 7.90(dd, J=2Hz, 8Hz, 1H), 8.00(d, J=2Hz, 1H), 15.77(b,1H)]

PREPARATION EXAMPLE 8

Compound No. 17 of the Present Invention

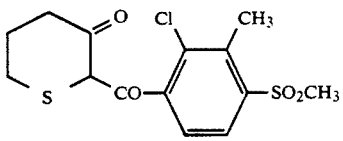

Two g (11.8 mmol) of the enamine obtained in Preparation Example 1 and 1.8 g (1.5 equivalent) of triethylamine were dissolved in 50 ml of dry tetrahydrofuran, and 2.4 g (9 mmol) of 2-chloro-3-methyl-4-methylsulfonylbenzoic acid chloride was dropwise added thereto while cooling with an ice bath, and the mixture was stirred at room temperature overnight.

Then, tetrahydrofuran was distilled off under reduced pressure, and then, 30 ml of chloroform was added thereto. Further, 20 ml of a 2N hydrochloric acid aqueous solution was added thereto, and the mixture was stirred for three hours. After an addition of water, the product was extracted with chloroform and dried over anhydrous sodium sulfate. Then, chloroform was distilled off under reduced pressure, and the product was purified by column chromatography to obtain 0.33 g (yield: 10.6%, melting point: 141.5°–144.0° C.) of 2-(2-chloro-3-methyl-4-methylsulfonylbenzoyl)-tetrahydrothiopyran-3-one.

1H-NMR δvalue; ((CDCl3)) 1.8–3.0 ppm(m, 6H), 2.8 ppm(s, 3H), 3.1 ppm(s, 3H), 7.3 ppm(d, 2H), 8.05 ppm(d, 2H), 1.52 ppm(br, 1H)

MS: M+ =346, melting point: 14.5°–144.0° C.]

PREPARATION EXAMPLE 9

Compound No. 29 of the Present Invention

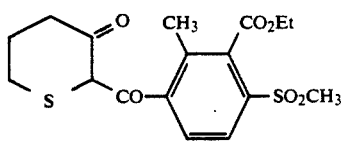

0.59 g (3.5 mmol) of the enamine obtained in Preparation Example 1 and 0.53 g (1.5 equivalent) of triethylamine were dissolved in 50 ml of dry tetrehydrofuran, and 0.93 g (3.5 mmol) of 2-methyl-3-ethoxycarbonyl-4-methylsulfonylbenzoic acid chloride was dropwise added, while cooling the solution with an ice bath. The mixture was stirred at room temperature for two hours. The mixture was then heated to 65° C. and stirred for further two hours.

Tetrahydrofuran was distilled off under reduced pressure, and 30 ml of chloroform was added to the residue. Further, 20 ml of a 2N hydrochloric acid aqueous solution was added thereto, and the mixture was stirred for 3 hours. After an addition of water, the product was extracted with chloroform and dried over anhydrous sodium sulfate. Chloroform was distilled off under reduced pressure, and the product was purified by column chromatography to obtain 0.13 g (yield: 10%) of 2-(2-methyl-3-ethoxycarbonyl-4-methylsulfonylbenzoyl)-tetrahydrothiopyran-3-one.

H-NMR δvalue: ((CDCl3)) 1.4 ppm(t, 3H), 2.3 ppm(s, 3H), 3.2 ppm(s, 3H), 1.7–3.3 ppm(m, 6H), 4.5 ppm(q, 2H), 7.1–8.2 ppm (m, 2H), 15.5 ppm(br)]

PREPARATION EXAMPLE 10

Compound No. 30 of the Present Invention

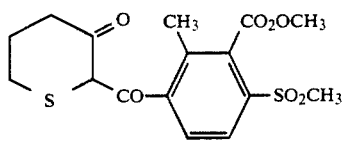

0.8 g (4.7 mmol) of the enamine obtained in Preparation Example 1 and 0.93 g (2 equivalent) of triethylamine were dissolved in 50 ml of dry tetrahydrofuran. Then, 1.27 g (4.6 mmol) of 2-methyl-3-methoxymethyl-4-methylsulfonylbenzoic acid chloride was dropwise added thereto while cooling with an ice bath. The mixture was stirred at room temperature overnight. Then, tetrahydrofuran was distilled off under reduced pressure, and 30 ml of chloroform was added to the residue, and 20 ml of a 2N hydrochloric acid aqueous solution was further added thereto. The mixture was stirred for 3 hours. After an addition of water, the product was extracted with chloroform and dried over anhydrous sodium sulfate. Then, chloroform was distilled off under reduced pressure, and the product was purified by column chromatography to obtain 0.53 g (yield: 32.4%, melting point: 151.5°–154.5° C.) of 2-(2-methyl-3-methoxymethyl-4-methylsulfonylbenzoyl)tetrahydrothiopyran-3-one.

[1H-NMR δvalue: ((CDCl3)) 2≧3 ppm(6H, m), 2.4 ppm(3H, s), 3.15 ppm(3H, s), 3.45 ppm(3H, s), 4.9 ppm(2H, s), 7–8 ppm (2H)

Melting point: 151.5-154.4° C.]

In a manner similar to the above reactions, compounds of the formula I of the present invention as identified in Tables 1 and 2 can be prepared. However, the present invention is not limited to such specific compounds.

The Compound Nos. in Tables 1 and 2 will be referred to in the subsequent Formulation Examples and Test Examples.

When the compound of the present invention is to be used as a herbicide, it is usually mixed with a suitable carrier, for instance, a solid carrier such as clay, talc, bentonite or diatomaceous earth, or a liquid carrier such as water, an alcohol (such as methanol or ethanol), an aromatic hydrocarbon (such as benzene, toluene or xylene), a chlorinated hydrocarbon, an ether, a ketone, an ester (such as ethyl acetate), or an acid amide (such as dimethylformamide). If desired, an emulsifier, a dispersing agent, a suspending agent, a penetrating agent, a spreader or a stabilizer may be added to prepare an optional formulation such as a liquid formulation, an emulsifiable concentrate, a wettable powder, a dust, a granule or a flowable. There is no particular restriction as to the content of the compound of the present invention as the active ingredient in such a formulation. However, the content is usually preferably within a range of from 0.10 to 90.0% by weight. Further, if desired, other herbicides, various insecticides, bacteriocides, plant growth regulating agents or synergism agents, may be combined at the time of the preparation of the formulations or at the time of the application. As such compounds to be combined, there may be mentioned, for instance, compounds disclosed in Farm Chemicals Handbook, the 75th Edition (1989).

The compound of the present invention can be applied to control various weeds not only in the agricultural and horticultural fields such as upland fields, paddy fields or orchards, but also in non-agricultural fields such as play grounds, non-used vacant fields, or rail way sides.

The dose varies depending upon the application site, the season for application, the manner of application, the type of weeds to be controlled, the type of crop plants, etc. However, the dose is usually within a range of from 0.005 to 10 kg per hectare as the amount of the active ingredient.

Now, Formulation Examples of the herbicides containing the compounds of the present invention as active ingredients, will be given. However, it should be understood that the present invention is by no means restricted to such specific Examples. In the following Formulation Examples, "parts" means "parts by weight".

Liquid Formulation

Active ingredient: 5-75 parts, preferably 10-50 parts, more preferably 15-40 parts,
Liquid carrier: 95-25 parts, preferably 88-30 parts, more preferably 82-40 parts,
Surfactant: 1 ∝ 30 parts, preferably 2-20 parts.

Emulsifiable Concentrate

Active ingredient: 1-50 parts, preferably 5-45 parts, more preferably 10-40 parts,
Surfactant: 1-30 parts, preferably 2-25 parts, more preferably 3-20 parts,
Liquid carrier: 20-95 parts, preferably 30-93 parts, more preferably 57-85 parts,

Dust

Active ingredient: 0.5-10 parts, preferably 15-40 parts,
Solid carrier: 95.9-90 parts.

Flowable

Active ingredient: 5-75 parts, preferably 10-50 parts,
Water: 94-25 parts, preferably 90-30 parts,
Surfactant: 1-30 parts, preferably 2-20 parts.

Wettable Powder

Active ingredient: 2.5-90 parts, preferably 10-80 parts, more preferably 20-75 parts,
Surfactant: 0.5-20 parts, preferably 1-15 parts, more preferably 2-10 parts,
Liquid carrier: 5-90 parts, preferably, 7.5-88 parts, more preferably 16-56 parts.

Granule

Active ingredient: 0.1-30 parts,
Solid carrier: 995.-70 parts.

The liquid formulation and the emulsifiable concentrate are prepared by dissolving the active ingredient in a liquid carrier containing a surfactant. The wettable powder is prepared by mixing a surfactant, a solid carrier and the active ingredient, followed by pulverization.

The dust is prepared by mixing a surfactant, a solid carrier and the active ingredient, if necessary, followed pulverization.

The flowable is prepared by suspending and dispersing the active ingredient in an aqueous solution containing a surfactant. The granule is prepared by mixing the active ingredient with an ajuvant.

FORMULATION EXAMPLE 1

Wettable Powder

| | |
|---|---|
| Compound No. 1 of the present invention | 50 parts |
| Zeeklite PFP (tradename for a kaolin-type clay, manufactured by Toho Chemical Co., Ltd.) | 43 parts |
| Sorpol 5039 (tradename for a mixture of a nonionic surfactant and an anionic surfactant, manufactured by Toho Chemical Co., Ltd.) | 5 parts |
| Carplex (tradename for a coagulation-preventing agent composed of a mixture of a surfactant and fine silica powder, manufactured by Shionogi Pharmaceutical Co., Ltd.) | 2 parts |

The above ingredients are homogeneously pulverized and mixed to form a wettable powder. In its use, the above wettable powder is diluted with water from 10 to 10,000 times and applied so that the active ingredient will be from 0.005 to 10 kg per hectare.

FORMULATION EXAMPLE 2

Emulsifiable Concentrate

| | |
|---|---|
| Compound No. 2 of the present invention | 10 parts |
| Xylene | 70 parts |
| N,N-dimethylformamide | 10 parts |
| Sorpol 2680 (tradename for a mixture of a nonionic surfactant and an anionic surfactant, manufactured by Toho Chemical Co., Ltd.) | 10 parts |

The above ingredients are homogeneously mixed to form an emulsifiable concentrate. In its use, the above emulsifiable concentrate is diluted with water from 10 to 10,000 times and applied so that the active ingredient will be from 0.005 to 10 kg per hectare.

FORMULATION EXAMPLE 3

Flowable

| | |
|---|---|
| Compound No. 3 of the present invention | 25 parts |
| Sorpol 3353 (tradename for a nonionic surfactant, manufactured by Toho Chemical Co., Ltd.) | 10 parts |
| Runox 1000C (tradename for an anionic surfactant, manufactured by Toho Chemical Co., Ltd.) | 0.5 part |
| 1% Xanthan gum aqueous solution (natural polymer) | 20 parts |
| Water | 44.5 parts |

Sorpol 3353, Runox 1000C and the 1% Xanthan gum aqueous solution were uniformly dissolved in water, then Compound No. 3 of the present invention was added, and the mixture was thoroughly stirred. Then, the mixture was subjected to wet pulverization by a sand mil to obtain a flowable. In its use, the above flowable is diluted from 10 to 10,000 times and applied so that the active ingredient will be 0.005 to 10 kg per hectare.

FORMULATION EXAMPLE 4

Liquid Formulation

| | |
|---|---|
| Compound No. 7 of the present invention | 20 parts |
| Sorpol W-150 (tradename for a nonionic surfactant, manufactured by Toho Chemical Co., Ltd.) | 10 part |
| Water | 70 parts |

The above ingredients are uniformly mixed to form a liquid formulation. In its use, the above liquid formulation is diluted from 10 to 10,000 times and applied so that the active ingredient will be from 0.005 to 10 kg per hectare.

FORMULATION EXAMPLE 5

Liquid Formulation

| | |
|---|---|
| Compound No. 17 of the present invention | 30 parts |
| Nippol (tradename for a nonionic surfactant, manufactured by Nissan Chemical Industries Ltd.) | 10 parts |
| Water | 60 parts |

The above ingredients are homogeneously mixed to obtain a liquid formulation. In its use, the above liquid formulation is diluted from 10 to 10,000 times and applied to so that the active ingredient will be from 0,005 to 10 kg per hectare.

FORMULATION EXAMPLE 6

Wettable Powder

| | |
|---|---|
| Compound No. 1736 of the present invention | 20 parts |
| Zeeklite PFP (tradename for a kaolin-type clay, manufactured by Zeeklite Industries, Co., Ltd.) | 73 parts |
| Sorpol 5039 (tradename for a mixture of a nonionic surfactant and an anionic surfactant, manufactured by Toho Chemical Co., Ltd.) | 5 parts |
| Carplex (tradename for a coagulation-preventing agent composed of a mixture of a surfactant and fine silica powder, manufactured by Shionogi Pharmaceutical Co., Ltd.) | 2 parts |

The above ingredients are homogeneously pulverized and mixed to form a wettable powder.

FORMULATION EXAMPLE 7

Wettable Powder

| | |
|---|---|
| Compound No. 29 of the present invention | 30 parts |
| Zeeklite PFP (tradename for a kaolin-type clay, manufactured by Zeeklite Industries, Co., Ltd.) | 63 parts |
| Sorpol 5039 (tradename for a mixture of a nonionic surfactant and an anionic surfactant, manufactured by Toho Chemical Co., Ltd.) | 5 parts |
| Carplex (tradename for a coagulation-preventing agent composed of a mixture of a surfactant and fine silica powder, manufactured by Shionogi Pharmaceutical Co., Ltd.) | 2 parts |

The above ingredients are homogeneously pulverized and mixed to form a wettable powder.

FORMULATION EXAMPLE 8

Granule

| | |
|---|---|
| Compound No. 32 of the present invention | 5 parts |
| Bentonite | 54 parts |
| Talc | 40 parts |
| Calcium lignin sulfonate | 1 part |

The above ingredients were homogenously mixed and pulverized, and after an addition of a small amount of water, the mixture was stirred, mixed and granulated by an extrusion-type granulating machine, followed by drying to obtain a granule. In its use, the above granule is applied so that the active ingredient will be from 0.005 to 10 kg per hectare.

Now, the herbicidal activities of the compounds of the present invention will be described in detail with reference to the following Test Examples.

TEST EXAMPLE 1

Test on the Herbicidal Effects in Soil Treatment

A plastic box having a length of 30 cm, a width of 22 cm and a depth of 6 cm was filled with a sterilized diluvium soil, and seeds of *Echinochloa crus-galli, Digitaria adscendens, Cyperus microiria, Solanum nigrum, Galinsoga ciliata, Rorripa indica, Zea mays* and *Triticum aestivum* were sown, and the soil was covered thereon in the thickness of about 1.5 cm, and then a herbicide solution was applied onto the surface of the soil uniformly so that the active ingredient was distributed at a predetermined concentration. The herbicide solution was prepared by diluting the liquid formulation, the wettable powder, the emulsifiable concentrate or the flowable as described in the foregoing Formulation Examples with water and applied onto the entire soil surface by means of a small spray. Three weeks after the application of the herbicidal solution, the herbicidal effects against each weed were determined on the basis of the following standard ratings.

Standard Ratings

5: Growth control rate of more than 90% (almost completely withered)
4: Growth control rate of from 70 to 90%
3: Growth control rate of from 40 to 70%
2: Growth control rate of from 20 to 40%
1: Growth control rate of from 5 to 20%
0: Growth control rate of less than 5% (almost non-effective)

The above growth control rates were calculated by the following equation:

$$\text{Growth control rate (\%)} = \left(1 - \frac{T}{N}\right) \times 100$$

where
T: Weight of the weed growth above the soil surface of the treated area
N: Weight of the weed growth above the soil surface of the non-treated area The results thereby obtained are shown in Table 3.

TEST EXAMPLE 2

Test 1 on the Herbicidal Effects in Foliage Treatment

A plastic box having a length of 30 cm, a width of 22 cm and a depth of 6 cm was filled with a sterilized diluvium soil, and seeds of *Echinochloa crus-galli, Digitaria adscendens, Cyperus microiria, Solanum nigrum, Galinsoga ciliata, Rorripa indica, Zea mays* and *Triticum aestivum* were spot-wisely sown, and the soil was covered thereon in a thickness of about 1.5 cm. When the various weeds and crop plant grew to the 2 to 3 leaf stage, a herbicidal solution was uniformly sprayed on the foliages so that the active ingredient was applied in a predetermined concentration.

The herbicidal solution was prepared by diluting the liquid formulation, the wettable powder, the emulsifiable concentrate or the flowable as described in the above Formulation Examples with water and applied onto the entire surface of the foliages of the weeds and the crop plant by a small spray. Three weeks after the application of the herbicide solution, the herbicidal effects against each weed and the phytotoxicities against each crop plant were determine on the basis of the standard ratings described in Test Example 1. The results are shown in Table 4.

In the following Tables 1 and 2, Me means a methyl group, Et means an ethyl group and Ph means a phenyl group.

In Tables 3 and 4, the following abbreviations are used.

EC: *Echinochloa crus-galli* (barnyardgrass)
Dose: Dose of active ingredient (kg/ha)
DI: *Digitaria adscendens* (large crabgrass)
CY: *Cyperus microiria* (flatsedge)
SO: *solanum nigrum* (black nigthshade)
GA: *Galinsoga ciliate* (hairy galinsoga)
RO: *Rorripa indica*
ZE: *Zea mays* (corn)
TR: *Triticum aestivum* (wheat)

TABLE 1

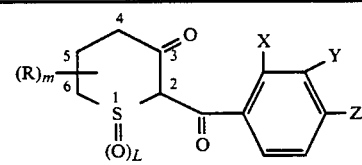

| Compound No. of present invention | $(R)_m$ | L | X | Y | Z | Chracteristic (Physical property) |
|---|---|---|---|---|---|---|
| 1 | — | 0 | Cl | H | Cl | Brown liquid $n_D^{25}$ 1.6288 |
| 2 | — | 0 | Cl | H | $SO_2Me$ | Slightly yellow crystal m.p. 111~113° C. |
| 3 | — | 0 | Cl | H | $NO_2$ | Reddish brown crystal m.p. 59.5~62.5° C. |
| 4 | — | 0 | Cl | H | OMe | |
| 5 | — | 0 | Cl | H | Me | |
| 6 | — | 0 | Cl | H | Br | |
| 7 | — | 0 | Cl | H | F | Yellowish brown liquid |
| 8 | — | 0 | Cl | H | SMe | |
| 9 | — | 0 | Cl | H | S(O)Me | |
| 10 | — | 0 | Cl | H | $CF_3$ | |
| 11 | — | 0 | Cl | H | CN | |
| 12 | — | 0 | Cl | Cl | Cl | |
| 13 | — | 0 | Cl | Cl | OMe | |
| 14 | — | 0 | Cl | Cl | SMe | |
| 15 | — | 0 | Cl | Cl | $SO_2Me$ | |
| 16 | — | 0 | Cl | Me | Cl | Yellow liquid $n_D^{20}$ 1.6312 |
| 17 | — | 0 | Cl | Me | $SO_2Me$ | Yellow crystal m.p. 141.5~144° C. |
| 18 | — | 0 | Cl | OMe | Cl | |
| 19 | — | 0 | Cl | OMe | Br | |
| 20 | — | 0 | Cl | OMe | $SO_2Me$ | |
| 21 | — | 0 | Cl | OEt | Br | |
| 22 | — | 0 | Br | H | OMe | |
| 23 | — | 0 | F | H | F | |
| 24 | — | 0 | I | I | I | |
| 25 | — | 0 | Me | H | CN | |
| 26 | — | 0 | Me | H | Me | |
| 27 | — | 0 | Me | H | OMe | |
| 28 | — | 0 | Me | Cl | Cl | |
| 29 | — | 0 | Me | $CO_2Et$ | $SO_2Me$ | Yellow semicrystal |
| 30 | — | 0 | Me | $CH_2OMe$ | $SO_2Me$ | Slightly yellow crystal m.p. 151.5~154.5° C. |
| 31 | — | 0 | Me | $CO_2Me$ | $SO_2Me$ | |
| 32 | — | 0 | $NO_2$ | H | Cl | Reddish brown crystal m.p. 113~116° C. |
| 33 | — | 0 | $NO_2$ | H | Br | |
| 34 | — | 0 | $NO_2$ | H | F | |
| 35 | — | 0 | $NO_2$ | H | CN | |
| 36 | — | 0 | $NO_2$ | H | SMe | |
| 37 | — | 0 | $NO_2$ | H | $CF_3$ | Slightly yellow crystal m.p. 104~106° C. |
| 38 | — | 0 | $NO_2$ | OMe | Cl | |

TABLE 1-continued

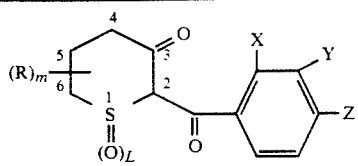

| Compound No. of present invention | (R)$_m$ | L | X | Y | Z | Characteristic (Physical property) |
|---|---|---|---|---|---|---|
| 39 | — | 0 | NO$_2$ | OMe | CF$_3$ | |
| 40 | — | 0 | CF$_3$ | H | Cl | |
| 41 | — | 0 | CF$_3$ | H | Br | |
| 42 | — | 0 | CF$_3$ | H | SMe | |
| 43 | — | 0 | CF$_3$ | H | CF$_3$ | |
| 44 | — | 0 | OMe | H | Cl | |
| 45 | — | 0 | OMe | H | OMe | Slightly yellow crystal m.p. 101~104° C. |
| 46 | — | 1 | Cl | H | Cl | |
| 47 | — | 1 | Cl | H | SO$_2$Me | |
| 48 | — | 1 | Cl | H | NO$_2$ | |
| 49 | — | 1 | Cl | H | OMe | |
| 50 | — | 1 | Cl | H | Me | |
| 51 | — | 1 | Cl | H | Br | |
| 52 | — | 1 | Cl | H | F | |
| 53 | — | 1 | Cl | H | SMe | |
| 54 | — | 1 | Cl | H | S(O)Me | |
| 55 | — | 1 | Cl | H | CF$_3$ | |
| 56 | — | 1 | Cl | H | CN | |
| 57 | — | 1 | Cl | Cl | Cl | |
| 58 | — | 1 | Cl | Cl | OMe | |
| 59 | — | 1 | Cl | Cl | SMe | |
| 60 | — | 1 | Cl | Cl | SO$_2$Me | |
| 61 | — | 1 | Cl | Me | Cl | |
| 62 | — | 1 | Cl | Me | SO$_2$Me | |
| 63 | — | 1 | Cl | OMe | Cl | |
| 64 | — | 1 | Cl | OMe | Br | |
| 65 | — | 1 | Cl | OMe | SO$_2$Me | |
| 66 | — | 1 | Cl | OEt | Br | |
| 67 | — | 1 | Br | H | OMe | |
| 68 | — | 1 | F | H | F | |
| 69 | — | 1 | I | I | I | |
| 70 | — | 1 | Me | H | CN | |
| 71 | — | 1 | Me | H | Me | |
| 72 | — | 1 | Me | H | OMe | |
| 73 | — | 1 | Me | Cl | Cl | |
| 74 | — | 1 | Me | CO$_2$Me | SO$_2$Me | |
| 75 | — | 1 | Me | CH$_2$OMe | SO$_2$Me | |
| 76 | — | 1 | Me | CH(Me)OMe | SO$_2$Me | |
| 77 | — | 1 | NO$_2$ | H | Cl | |
| 78 | — | 1 | NO$_2$ | H | Br | |
| 79 | — | 1 | NO$_2$ | H | F | |
| 80 | — | 1 | NO$_2$ | H | CN | |
| 81 | — | 1 | NO$_2$ | H | SMe | |
| 82 | — | 1 | NO$_2$ | H | CF$_3$ | |
| 83 | — | 1 | NO$_2$ | OMe | Cl | |
| 84 | — | 1 | NO$_2$ | OMe | CF$_3$ | |
| 85 | — | 1 | CF$_3$ | H | Cl | |
| 86 | — | 1 | CF$_3$ | H | Br | |
| 87 | — | 1 | CF$_3$ | H | SMe | |
| 88 | — | 1 | CF$_3$ | H | CF$_3$ | |
| 89 | — | 1 | OMe | H | Cl | |
| 90 | — | 1 | OMe | H | OMe | |
| 91 | — | 2 | Cl | H | Cl | |
| 92 | — | 2 | Cl | H | SO$_2$Me | |
| 93 | — | 2 | Cl | H | NO$_2$ | |
| 94 | — | 2 | Cl | H | OMe | |
| 95 | — | 2 | Cl | H | Me | |
| 96 | — | 2 | Cl | H | Br | |
| 97 | — | 2 | Cl | H | F | |
| 98 | — | 2 | Cl | H | SMe | |
| 99 | — | 2 | Cl | H | S(O)Me | |
| 100 | — | 2 | Cl | H | CF$_3$ | |
| 101 | — | 2 | Cl | H | CN | |
| 102 | — | 2 | Cl | Cl | Cl | |
| 103 | — | 2 | Cl | Cl | OMe | |
| 104 | — | 2 | Cl | Cl | SMe | |
| 105 | — | 2 | Cl | Cl | SO$_2$Me | |
| 106 | — | 2 | Cl | Me | Cl | |
| 107 | — | 2 | Cl | Me | SO$_2$Me | |
| 108 | — | 2 | Cl | OMe | Cl | |

TABLE 1-continued

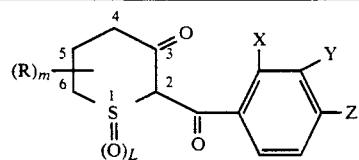

| Compound No. of present invention | $(R)_m$ | L | X | Y | Z | Chracteristic (Physical property) |
|---|---|---|---|---|---|---|
| 109 | — | 2 | Cl | OMe | Br | |
| 110 | — | 2 | Cl | OMe | $SO_2Me$ | |
| 111 | — | 2 | Cl | OEt | Br | |
| 112 | — | 2 | Br | H | OMe | |
| 113 | — | 2 | F | H | F | |
| 114 | — | 2 | I | I | I | |
| 115 | — | 2 | Me | H | CN | |
| 116 | — | 2 | Me | H | Me | |
| 117 | — | 2 | Me | H | OMe | |
| 118 | — | 2 | Me | Cl | Cl | |
| 119 | — | 2 | Me | $CO_2Me$ | $SO_2Me$ | |
| 120 | — | 2 | Me | $CH_2OMe$ | $SO_2Me$ | |
| 121 | — | 2 | Me | CH(Me)OMe | $SO_2Me$ | |
| 122 | — | 2 | $NO_2$ | H | Cl | |
| 123 | — | 2 | $NO_2$ | H | Br | |
| 124 | — | 2 | $NO_2$ | H | F | |
| 125 | — | 2 | $NO_2$ | H | CN | |
| 126 | — | 2 | $NO_2$ | H | SMe | |
| 127 | — | 2 | $NO_2$ | H | $CF_3$ | |
| 128 | — | 2 | $NO_2$ | OMe | Cl | |
| 129 | — | 2 | $NO_2$ | OMe | $CF_3$ | |
| 130 | — | 2 | $CF_3$ | H | Cl | |
| 131 | — | 2 | $CF_3$ | H | Br | |
| 132 | — | 2 | $CF_3$ | H | SMe | |
| 133 | — | 2 | $CF_3$ | H | $CF_3$ | |
| 134 | — | 2 | OMe | H | Cl | |
| 135 | — | 2 | OMe | H | OMe | |
| 136 | 4-Me | 0 | Cl | H | Cl | |
| 137 | 4-Me | 0 | Cl | H | $SO_2Me$ | |
| 138 | 4-Me | 0 | Cl | H | $NO_2$ | |
| 139 | 4-Me | 0 | Cl | H | OMe | |
| 140 | 4-Me | 0 | Cl | H | Me | |
| 141 | 4-Me | 0 | Cl | H | Br | |
| 142 | 4-Me | 0 | Cl | H | F | |
| 143 | 4-Me | 0 | Cl | H | SMe | |
| 144 | 4-Me | 0 | Cl | H | S(O)Me | |
| 145 | 4-Me | 0 | Cl | H | $CF_3$ | |
| 146 | 4-Me | 0 | Cl | H | CN | |
| 147 | 4-Me | 0 | Cl | Cl | Cl | |
| 148 | 4-Me | 0 | Cl | Cl | OMe | |
| 149 | 4-Me | 0 | Cl | Cl | SMe | |
| 150 | 4-Me | 0 | Cl | Cl | $SO_2Me$ | |
| 151 | 4-Me | 0 | Cl | Me | Cl | |
| 152 | 4-Me | 0 | Cl | Me | $SO_2Me$ | |
| 153 | 4-Me | 0 | Cl | OMe | Cl | |
| 154 | 4-Me | 0 | Cl | OMe | Br | |
| 155 | 4-Me | 0 | Cl | OMe | $SO_2Me$ | |
| 156 | 4-Me | 0 | Cl | OEt | Br | |
| 157 | 4-Me | 0 | Br | H | OMe | |
| 158 | 4-Me | 0 | F | H | F | |
| 159 | 4-Me | 0 | I | I | I | |
| 160 | 4-Me | 0 | Me | H | CN | |
| 161 | 4-Me | 0 | Me | H | Me | |
| 162 | 4-Me | 0 | Me | H | OMe | |
| 163 | 4-Me | 0 | Me | Cl | Cl | |
| 164 | 4-Me | 0 | Me | $CO_2Me$ | $SO_2Me$ | |
| 165 | 4-Me | 0 | Me | $CH_2OMe$ | $SO_2Me$ | |
| 166 | 4-Me | 0 | Me | CH(Me)OMe | $SO_2Me$ | |
| 167 | 4-Me | 0 | $NO_2$ | H | Cl | |
| 168 | 4-Me | 0 | $NO_2$ | H | Br | |
| 169 | 4-Me | 0 | $NO_2$ | H | F | |
| 170 | 4-Me | 0 | $NO_2$ | H | CN | |
| 171 | 4-Me | 0 | $NO_2$ | H | SMe | |
| 172 | 4-Me | 0 | $NO_2$ | H | $CF_3$ | |
| 173 | 4-Me | 0 | $NO_2$ | OMe | Cl | |
| 174 | 4-Me | 0 | $NO_2$ | OMe | $CF_3$ | |
| 175 | 4-Me | 0 | $CF_3$ | H | Cl | |
| 176 | 4-Me | 0 | $CF_3$ | H | Br | |
| 177 | 4-Me | 0 | $CF_3$ | H | SMe | |
| 178 | 4-Me | 0 | $CF_3$ | H | $CF_3$ | |
| 179 | 4-Me | 0 | OMe | H | Cl | |

TABLE 1-continued

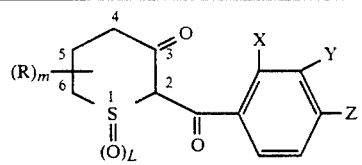

| Compound No. of present invention | (R)$_m$ | L | X | Y | Z | Charcteristic (Physical property) |
|---|---|---|---|---|---|---|
| 180 | 4-Me | 0 | OMe | H | OMe | |
| 181 | 4-Me | 1 | Cl | H | Cl | |
| 182 | 4-Me | 1 | Cl | H | SO$_2$Me | |
| 183 | 4-Me | 1 | Cl | H | NO$_2$ | |
| 184 | 4-Me | 1 | Cl | H | OMe | |
| 185 | 4-Me | 1 | Cl | H | Me | |
| 186 | 4-Me | 1 | Cl | H | Br | |
| 187 | 4-Me | 1 | Cl | H | F | |
| 188 | 4-Me | 1 | Cl | H | SMe | |
| 189 | 4-Me | 1 | Cl | H | S(O)Me | |
| 190 | 4-Me | 1 | Cl | H | CF$_3$ | |
| 191 | 4-Me | 1 | Cl | H | CN | |
| 192 | 4-Me | 1 | Cl | Cl | Cl | |
| 193 | 4-Me | 1 | Cl | Cl | OMe | |
| 194 | 4-Me | 1 | Cl | Cl | SMe | |
| 195 | 4-Me | 1 | Cl | Cl | SO$_2$Me | |
| 196 | 4-Me | 1 | Cl | Me | Cl | |
| 197 | 4-Me | 1 | Cl | Me | SO$_2$Me | |
| 198 | 4-Me | 1 | Cl | OMe | Cl | |
| 199 | 4-Me | 1 | Cl | OMe | Br | |
| 200 | 4-Me | 1 | Cl | OMe | SO$_2$Me | |
| 201 | 4-Me | 1 | Cl | OEt | Br | |
| 202 | 4-Me | 1 | Br | H | OMe | |
| 203 | 4-Me | 1 | F | H | F | |
| 204 | 4-Me | 1 | I | I | I | |
| 205 | 4-Me | 1 | Me | H | CN | |
| 206 | 4-Me | 1 | Me | H | Me | |
| 207 | 4-Me | 1 | Me | H | OMe | |
| 208 | 4-Me | 1 | Me | Cl | Cl | |
| 209 | 4-Me | 1 | Me | CO$_2$Me | SO$_2$Me | |
| 210 | 4-Me | 1 | Me | CH$_2$OMe | SO$_2$Me | |
| 211 | 4-Me | 1 | Me | CH(Me)OMe | SO$_2$Me | |
| 212 | 4-Me | 1 | NO$_2$ | H | Cl | |
| 213 | 4-Me | 1 | NO$_2$ | H | Br | |
| 214 | 4-Me | 1 | NO$_2$ | H | F | |
| 215 | 4-Me | 1 | NO$_2$ | H | CN | |
| 216 | 4-Me | 1 | NO$_2$ | H | SMe | |
| 217 | 4-Me | 1 | NO$_2$ | H | CF$_3$ | |
| 218 | 4-Me | 1 | NO$_2$ | OMe | Cl | |
| 219 | 4-Me | 1 | NO$_2$ | OMe | CF$_3$ | |
| 220 | 4-Me | 1 | CF$_3$ | H | Cl | |
| 221 | 4-Me | 1 | CF$_3$ | H | Br | |
| 222 | 4-Me | 1 | CF$_3$ | H | SMe | |
| 223 | 4-Me | 1 | CF$_3$ | H | CF$_3$ | |
| 224 | 4-Me | 1 | OMe | H | Cl | |
| 225 | 4-Me | 1 | OMe | H | OMe | |
| 226 | 4-Me | 2 | Cl | H | Cl | |
| 227 | 4-Me | 2 | Cl | H | SO$_2$Me | |
| 228 | 4-Me | 2 | Cl | H | NO$_2$ | |
| 229 | 4-Me | 2 | Cl | H | OMe | |
| 230 | 4-Me | 2 | Cl | H | Me | |
| 231 | 4-Me | 2 | Cl | H | Br | |
| 232 | 4-Me | 2 | Cl | H | F | |
| 233 | 4-Me | 2 | Cl | H | SMe | |
| 234 | 4-Me | 2 | Cl | H | S(O)Me | |
| 235 | 4-Me | 2 | Cl | H | CF$_3$ | |
| 236 | 4-Me | 2 | Cl | H | CN | |
| 237 | 4-Me | 2 | Cl | Cl | Cl | |
| 238 | 4-Me | 2 | Cl | Cl | OMe | |
| 239 | 4-Me | 2 | Cl | Cl | SMe | |
| 240 | 4-Me | 2 | Cl | Cl | SO$_2$Me | |
| 241 | 4-Me | 2 | Cl | Me | Cl | |
| 242 | 4-Me | 2 | Cl | Me | SO$_2$Me | |
| 243 | 4-Me | 2 | Cl | OMe | Cl | |
| 244 | 4-Me | 2 | Cl | OMe | Br | |
| 245 | 4-Me | 2 | Cl | OMe | SO$_2$Me | |
| 246 | 4-Me | 2 | Cl | OEt | Br | |
| 247 | 4-Me | 2 | Br | H | OMe | |
| 248 | 4-Me | 2 | F | H | F | |
| 249 | 4-Me | 1 | I | I | | |
| 250 | 4-Me | 2 | Me | H | CN | |

TABLE 1-continued

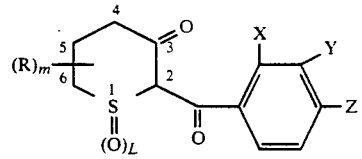

| Compound No. of present invention | (R)$_m$ | L | X | Y | Z | Chracteristic (Physical property) |
|---|---|---|---|---|---|---|
| 251 | 4-Me | 2 | Me | H | Me | |
| 252 | 4-Me | 2 | Me | H | OMe | |
| 253 | 4-Me | 2 | Me | Cl | Cl | |
| 254 | 4-Me | 2 | Me | CO$_2$Me | SO$_2$Me | |
| 255 | 4-Me | 2 | Me | CH$_2$OMe | SO$_2$Me | |
| 256 | 4-Me | 2 | Me | CH(Me)OMe | SO$_2$Me | |
| 257 | 4-Me | 2 | NO$_2$ | H | Cl | |
| 258 | 4-Me | 2 | NO$_2$ | H | Br | |
| 259 | 4-Me | 2 | NO$_2$ | H | F | |
| 260 | 4-Me | 2 | NO$_2$ | H | CN | |
| 261 | 4-Me | 2 | NO$_2$ | H | SMe | |
| 262 | 4-Me | 2 | NO$_2$ | H | CF$_3$ | |
| 263 | 4-Me | 2 | NO$_2$ | OMe | Cl | |
| 264 | 4-Me | 2 | NO$_2$ | OMe | CF$_3$ | |
| 265 | 4-Me | 2 | CF$_3$ | H | Cl | |
| 266 | 4-Me | 2 | CF$_3$ | H | Br | |
| 267 | 4-Me | 2 | CF$_3$ | H | SMe | |
| 268 | 4-Me | 2 | CF$_3$ | H | CF$_3$ | |
| 269 | 4-Me | 2 | OMe | H | Cl | |
| 270 | 4-Me | 2 | OMe | H | OMe | |
| 271 | 5-Me | 0 | Cl | H | Cl | |
| 272 | 5-Me | 0 | Cl | H | SO$_2$Me | |
| 273 | 5-Me | 0 | Cl | H | NO$_2$ | |
| 274 | 5-Me | 0 | Cl | H | OMe | |
| 275 | 5-Me | 0 | Cl | H | Me | |
| 276 | 5-Me | 0 | Cl | H | Br | |
| 277 | 5-Me | 0 | Cl | H | F | |
| 278 | 5-Me | 0 | Cl | H | SMe | |
| 279 | 5-Me | 0 | Cl | H | S(O)Me | |
| 280 | 5-Me | 0 | Cl | H | CF$_3$ | |
| 281 | 5-Me | 0 | Cl | H | CN | |
| 282 | 5-Me | 0 | Cl | Cl | Cl | |
| 283 | 5-Me | 0 | Cl | Cl | OMe | |
| 284 | 5-Me | 0 | Cl | Cl | SMe | |
| 285 | 5-Me | 0 | Cl | Cl | SO$_2$Me | |
| 286 | 5-Me | 0 | Cl | Me | Cl | |
| 287 | 5-Me | 0 | Cl | Me | SO$_2$Me | |
| 288 | 5-Me | 0 | Cl | OMe | Cl | |
| 289 | 5-Me | 0 | Cl | OMe | Br | |
| 290 | 5-Me | 0 | Cl | OMe | SO$_2$Me | |
| 291 | 5-Me | 0 | Cl | OEt | Br | |
| 292 | 5-Me | 0 | Br | H | OMe | |
| 293 | 5-Me | 0 | F | H | F | |
| 294 | 5-Me | 0 | I | I | I | |
| 295 | 5-Me | 0 | Me | H | CN | |
| 296 | 5-Me | 0 | Me | H | Me | |
| 297 | 5-Me | 0 | Me | H | OMe | |
| 298 | 5-Me | 0 | Me | Cl | Cl | |
| 299 | 5-Me | 0 | Me | CO$_2$Me | SO$_2$Me | |
| 300 | 5-Me | 0 | Me | CH$_2$OMe | SO$_2$Me | |
| 301 | 5-Me | 0 | Me | CH(Me)OMe | SO$_2$Me | |
| 302 | 5-Me | 0 | NO$_2$ | H | Cl | |
| 303 | 5-Me | 0 | NO$_2$ | H | Br | |
| 304 | 5-Me | 0 | NO$_2$ | H | F | |
| 305 | 5-Me | 0 | NO$_2$ | H | CN | |
| 306 | 5-Me | 0 | NO$_2$ | H | SMe | |
| 307 | 5-Me | 0 | NO$_2$ | H | CF$_3$ | |
| 308 | 5-Me | 0 | NO$_2$ | OMe | Cl | |
| 309 | 5-Me | 0 | NO$_2$ | OMe | CF$_3$ | |
| 310 | 5-Me | 0 | CF$_3$ | H | Cl | |
| 311 | 5-Me | 0 | CF$_3$ | H | Br | |
| 312 | 5-Me | 0 | CF$_3$ | H | SMe | |
| 313 | 5-Me | 0 | CF$_3$ | H | CF$_3$ | |
| 314 | 5-Me | 0 | OMe | H | Cl | |
| 315 | 5-Me | 0 | OMe | H | OMe | |
| 316 | 5-Me | 1 | Cl | H | Cl | |
| 317 | 5-Me | 1 | Cl | H | SO$_2$Me | |
| 318 | 5-Me | 1 | Cl | H | NO$_2$ | |
| 319 | 5-Me | 1 | Cl | H | OMe | |
| 320 | 5-Me | 1 | Cl | H | Me | |
| 321 | 5-Me | 1 | Cl | H | Br | |

TABLE 1-continued

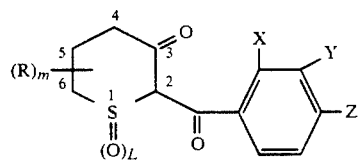

| Compound No. of present invention | (R)$_m$ | L | X | Y | Z | Chracteristic (Physical property) |
|---|---|---|---|---|---|---|
| 322 | 5-Me | 1 | Cl | H | F | |
| 323 | 5-Me | 1 | Cl | H | SMe | |
| 324 | 5-Me | 1 | Cl | H | S(O)Me | |
| 325 | 5-Me | 1 | Cl | H | CF$_3$ | |
| 326 | 5-Me | 1 | Cl | H | CN | |
| 327 | 5-Me | 1 | Cl | Cl | Cl | |
| 328 | 5-Me | 1 | Cl | Cl | OMe | |
| 329 | 5-Me | 1 | Cl | Cl | SMe | |
| 330 | 5-Me | 1 | Cl | Cl | SO$_2$Me | |
| 331 | 5-Me | 1 | Cl | Me | Cl | |
| 332 | 5-Me | 1 | Cl | Me | SO$_2$Me | |
| 333 | 5-Me | 1 | Cl | OMe | Cl | |
| 334 | 5-Me | 1 | Cl | OMe | Br | |
| 335 | 5-Me | 1 | Cl | OMe | SO$_2$Me | |
| 336 | 5-Me | 1 | Cl | OEt | Br | |
| 337 | 5-Me | 1 | Br | H | OMe | |
| 338 | 5-Me | 1 | F | H | F | |
| 339 | 5-Me | 1 | I | I | I | |
| 340 | 5-Me | 1 | Me | H | CN | |
| 341 | 5-Me | 1 | Me | H | Me | |
| 342 | 5-Me | 1 | Me | H | OMe | |
| 343 | 5-Me | 1 | Me | Cl | Cl | |
| 344 | 5-Me | 1 | Me | CO$_2$Me | SO$_2$Me | |
| 345 | 5-Me | 1 | Me | CH$_2$OMe | SO$_2$Me | |
| 346 | 5-Me | 1 | Me | CH(Me)OMe | SO$_2$Me | |
| 347 | 5-Me | 1 | NO$_2$ | H | Cl | |
| 348 | 5-Me | 1 | NO$_2$ | H | Br | |
| 349 | 5-Me | 1 | NO$_2$ | H | F | |
| 350 | 5-Me | 1 | NO$_2$ | H | CN | |
| 351 | 5-Me | 1 | NO$_2$ | H | SMe | |
| 352 | 5-Me | 1 | NO$_2$ | H | CF$_3$ | |
| 353 | 5-Me | 1 | NO$_2$ | OMe | Cl | |
| 354 | 5-Me | 1 | NO$_2$ | OMe | CF$_3$ | |
| 355 | 5-Me | 1 | CF$_3$ | H | Cl | |
| 356 | 5-Me | 1 | CF$_3$ | H | Br | |
| 357 | 5-Me | 1 | CF$_3$ | H | SMe | |
| 358 | 5-Me | 1 | CF$_3$ | H | CF$_3$ | |
| 359 | 5-Me | 1 | OMe | H | Cl | |
| 360 | 5-Me | 1 | OMe | H | OMe | |
| 361 | 5-Me | 2 | Cl | H | Cl | |
| 362 | 5-Me | 2 | Cl | H | SO$_2$Me | |
| 363 | 5-Me | 2 | Cl | H | NO$_2$ | |
| 364 | 5-Me | 2 | Cl | H | OMe | |
| 365 | 5-Me | 2 | Cl | H | Me | |
| 366 | 5-Me | 2 | Cl | H | Br | |
| 367 | 5-Me | 2 | Cl | H | F | |
| 368 | 5-Me | 2 | Cl | H | SMe | |
| 369 | 5-Me | 2 | Cl | H | S(O)Me | |
| 370 | 5-Me | 2 | Cl | H | CF$_3$ | |
| 371 | 5-Me | 2 | Cl | H | CN | |
| 372 | 5-Me | 2 | Cl | Cl | Cl | |
| 373 | 5-Me | 2 | Cl | Cl | OMe | |
| 374 | 5-Me | 2 | Cl | Cl | SMe | |
| 375 | 5-Me | 2 | Cl | Cl | SO$_2$Me | |
| 376 | 5-Me | 2 | Cl | Me | Cl | |
| 377 | 5-Me | 2 | Cl | Me | SO$_2$Me | |
| 378 | 5-Me | 2 | Cl | OMe | Cl | |
| 379 | 5-Me | 2 | Cl | OMe | Br | |
| 380 | 5-Me | 2 | Cl | OMe | SO$_2$Me | |
| 381 | 5-Me | 2 | Cl | OEt | Br | |
| 382 | 5-Me | 2 | Br | H | OMe | |
| 383 | 5-Me | 2 | F | H | F | |
| 384 | 5-Me | 2 | I | I | I | |
| 385 | 5-Me | 2 | Me | H | CN | |
| 386 | 5-Me | 2 | Me | H | Me | |
| 387 | 5-Me | 2 | Me | H | OMe | |
| 388 | 5-Me | 2 | Me | Cl | Cl | |
| 389 | 5-Me | 2 | Me | CO$_2$Me | SO$_2$Me | |
| 390 | 5-Me | 2 | Me | CH$_2$OMe | SO$_2$Me | |
| 391 | 5-Me | 2 | Me | CH(Me)OMe | SO$_2$Me | |
| 392 | 5-Me | 2 | NO$_2$ | H | Cl | |

TABLE 1-continued

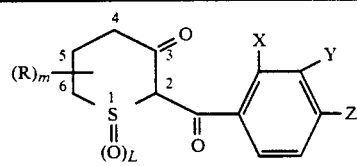

| Compound No. of present invention | (R)$_m$ | L | X | Y | Z | Chracteristic (Physical property) |
|---|---|---|---|---|---|---|
| 393 | 5-Me | 2 | NO$_2$ | H | Br | |
| 394 | 5-Me | 2 | NO$_2$ | H | F | |
| 395 | 5-Me | 2 | NO$_2$ | H | CN | |
| 396 | 5-Me | 2 | NO$_2$ | H | SMe | |
| 397 | 5-Me | 2 | NO$_2$ | H | CF$_3$ | |
| 398 | 5-Me | 2 | NO$_2$ | OMe | Cl | |
| 399 | 5-Me | 2 | NO$_2$ | OMe | CF$_3$ | |
| 400 | 5-Me | 2 | CF$_3$ | H | Cl | |
| 401 | 5-Me | 2 | CF$_3$ | H | Br | |
| 402 | 5-Me | 2 | CF$_3$ | H | SMe | |
| 403 | 5-Me | 2 | CF$_3$ | H | CF$_3$ | |
| 404 | 5-Me | 2 | OMe | H | Cl | |
| 405 | 5-Me | 2 | OMe | H | OMe | |
| 406 | 6-Me | 0 | Cl | H | Cl | Slightly green liquid $n_D^{20}$ 1.6219 |
| 407 | 6-Me | 0 | Cl | H | SO$_2$Me | |
| 408 | 6-Me | 0 | Cl | H | NO$_2$ | |
| 409 | 6-Me | 0 | Cl | H | OMe | |
| 410 | 6-Me | 0 | Cl | H | Me | |
| 411 | 6-Me | 0 | Cl | H | Br | |
| 412 | 6-Me | 0 | Cl | H | F | |
| 413 | 6-Me | 0 | Cl | H | SMe | |
| 414 | 6-Me | 0 | Cl | H | S(O)Me | |
| 415 | 6-Me | 0 | Cl | H | CF$_3$ | |
| 416 | 6-Me | 0 | Cl | H | CN | |
| 417 | 6-Me | 0 | Cl | Cl | Cl | |
| 418 | 6-Me | 0 | Cl | Cl | OMe | |
| 419 | 6-Me | 0 | Cl | Cl | SMe | |
| 420 | 6-Me | 0 | Cl | Cl | SO$_2$Me | |
| 421 | 6-Me | 0 | Cl | Me | Cl | Slightly yellow liquid $n_D^{20}$ 1.6203 |
| 422 | 6-Me | 0 | Cl | Me | SO$_2$Me | |
| 423 | 6-Me | 0 | Cl | OMe | Cl | |
| 424 | 6-Me | 0 | Cl | OMe | Br | |
| 425 | 6-Me | 0 | Cl | OMe | SO$_2$Me | |
| 426 | 6-Me | 0 | Cl | OEt | Br | |
| 427 | 6-Me | 0 | Br | H | OMe | |
| 428 | 6-Me | 0 | F | H | F | |
| 429 | 6-Me | 0 | I | I | I | |
| 430 | 6-Me | 0 | Me | H | CN | |
| 431 | 6-Me | 0 | Me | H | Me | |
| 432 | 6-Me | 0 | Me | H | OMe | |
| 433 | 6-Me | 0 | Me | Cl | Cl | |
| 434 | 6-Me | 0 | Me | CO$_2$Me | SO$_2$Me | |
| 435 | 6-Me | 0 | Me | CH$_2$OMe | SO$_2$Me | |
| 436 | 6-Me | 0 | Me | CH(Me)OMe | SO$_2$Me | |
| 437 | 6-Me | 0 | NO$_2$ | H | Cl | |
| 438 | 6-Me | 0 | NO$_2$ | H | Br | |
| 439 | 6-Me | 0 | NO$_2$ | H | F | |
| 440 | 6-Me | 0 | NO$_2$ | H | CN | |
| 441 | 6-Me | 0 | NO$_2$ | H | SMe | |
| 442 | 6-Me | 0 | NO$_2$ | H | CF$_3$ | Slightly yellow crystal m.p. 88~91° C. |
| 443 | 6-Me | 0 | NO$_2$ | OMe | Cl | |
| 444 | 6-Me | 0 | NO$_2$ | OMe | CF$_3$ | |
| 445 | 6-Me | 0 | CF$_3$ | H | Cl | |
| 446 | 6-Me | 0 | CF$_3$ | H | Br | |
| 447 | 6-Me | 0 | CF$_3$ | H | SMe | |
| 448 | 6-Me | 0 | CF$_3$ | H | CF$_3$ | |
| 449 | 6-Me | 0 | OMe | H | Cl | |
| 450 | 6-Me | 0 | OMe | H | OMe | |
| 451 | 6-Me | 1 | Cl | H | Cl | |
| 452 | 6-Me | 1 | Cl | H | SO$_2$Me | |
| 453 | 6-Me | 1 | Cl | H | NO$_2$ | |
| 454 | 6-Me | 1 | Cl | H | OMe | |
| 455 | 6-Me | 1 | Cl | H | Me | |
| 456 | 6-Me | 1 | Cl | H | Br | |
| 457 | 6-Me | 1 | Cl | H | F | |
| 458 | 6-Me | 1 | Cl | H | SMe | |
| 459 | 6-Me | 1 | Cl | H | S(O)Me | |
| 460 | 6-Me | 1 | Cl | H | CF$_3$ | |

TABLE 1-continued

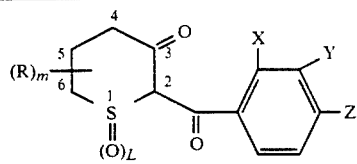

| Compound No. of present invention | (R)$_m$ | L | X | Y | Z | Chracteristic (Physical property) |
|---|---|---|---|---|---|---|
| 461 | 6-Me | 1 | Cl | H | CN | |
| 462 | 6-Me | 1 | Cl | Cl | Cl | |
| 463 | 6-Me | 1 | Cl | Cl | OMe | |
| 464 | 6-Me | 1 | Cl | Cl | SMe | |
| 465 | 6-Me | 1 | Cl | Cl | SO$_2$Me | |
| 466 | 6-Me | 1 | Cl | Me | Cl | |
| 467 | 6-Me | 1 | Cl | Me | SO$_2$Me | |
| 468 | 6-Me | 1 | Cl | OMe | Cl | |
| 469 | 6-Me | 1 | Cl | OMe | Br | |
| 470 | 6-Me | 1 | Cl | OMe | SO$_2$Me | |
| 471 | 6-Me | 1 | Cl | OEt | Br | |
| 472 | 6-Me | 1 | Br | H | OMe | |
| 473 | 6-Me | 1 | F | H | F | |
| 474 | 6-Me | 1 | I | I | I | |
| 475 | 6-Me | 1 | Me | H | CN | |
| 476 | 6-Me | 1 | Me | H | Me | |
| 477 | 6-Me | 1 | Me | H | OMe | |
| 478 | 6-Me | 1 | Me | Cl | Cl | |
| 479 | 6-Me | 1 | Me | CO$_2$Me | SO$_2$Me | |
| 480 | 6-Me | 1 | Me | CH$_2$OMe | SO$_2$Me | |
| 481 | 6-Me | 1 | Me | CH(Me)OMe | SO$_2$Me | |
| 482 | 6-Me | 1 | NO$_2$ | H | Cl | |
| 483 | 6-Me | 1 | NO$_2$ | H | Br | |
| 484 | 6-Me | 1 | NO$_2$ | H | F | |
| 485 | 6-Me | 1 | NO$_2$ | H | CN | |
| 486 | 6-Me | 1 | NO$_2$ | H | SMe | |
| 487 | 6-Me | 1 | NO$_2$ | H | CF$_3$ | |
| 488 | 6-Me | 1 | NO$_2$ | OMe | Cl | |
| 489 | 6-Me | 1 | NO$_2$ | OMe | CF$_3$ | |
| 490 | 6-Me | 1 | CF$_3$ | H | Cl | |
| 491 | 6-Me | 1 | CF$_3$ | H | Br | |
| 492 | 6-Me | 1 | CF$_3$ | H | SMe | |
| 493 | 6-Me | 1 | CF$_3$ | H | CF$_3$ | |
| 494 | 6-Me | 1 | OMe | H | Cl | |
| 495 | 6-Me | 1 | OMe | H | OMe | |
| 496 | 6-Me | 2 | Cl | H | Cl | |
| 497 | 6-Me | 2 | Cl | H | SO$_2$Me | |
| 498 | 6-Me | 2 | Cl | H | NO$_2$ | |
| 499 | 6-Me | 2 | Cl | H | OMe | |
| 500 | 6-Me | 2 | Cl | H | Me | |
| 501 | 6-Me | 2 | Cl | H | Br | |
| 502 | 6-Me | 2 | Cl | H | F | |
| 503 | 6-Me | 2 | Cl | H | SMe | |
| 504 | 6-Me | 2 | Cl | H | S(O)Me | |
| 505 | 6-Me | 2 | Cl | H | CF$_3$ | |
| 506 | 6-Me | 2 | Cl | H | CN | |
| 507 | 6-Me | 2 | Cl | Cl | Cl | |
| 508 | 6-Me | 2 | Cl | Cl | OMe | |
| 509 | 6-Me | 2 | Cl | Cl | SMe | |
| 510 | 6-Me | 2 | Cl | Cl | SO$_2$Me | |
| 511 | 6-Me | 2 | Cl | Me | Cl | |
| 512 | 6-Me | 2 | Cl | Me | SO$_2$Me | |
| 513 | 6-Me | 2 | Cl | OMe | Cl | |
| 514 | 6-Me | 2 | Cl | OMe | Br | |
| 515 | 6-Me | 2 | Cl | OMe | SO$_2$Me | |
| 516 | 6-Me | 2 | Cl | OEt | Br | |
| 517 | 6-Me | 2 | Br | H | OMe | |
| 518 | 6-Me | 2 | F | H | F | |
| 519 | 6-Me | 2 | I | I | I | |
| 520 | 6-Me | 2 | Me | H | CN | |
| 521 | 6-Me | 2 | Me | H | Me | |
| 522 | 6-Me | 2 | Me | H | OMe | |
| 523 | 6-Me | 2 | Me | Cl | Cl | |
| 524 | 6-Me | 2 | Me | CO$_2$Me | SO$_2$Me | |
| 525 | 6-Me | 2 | Me | CH$_2$OMe | SO$_2$Me | |
| 526 | 6-Me | 2 | Me | CH(Me)OMe | SO$_2$Me | |
| 527 | 6-Me | 2 | NO$_2$ | H | Cl | |
| 528 | 6-Me | 2 | NO$_2$ | H | Br | |
| 529 | 6-Me | 2 | NO$_2$ | H | F | |
| 530 | 6-Me | 2 | NO$_2$ | H | CN | |
| 531 | 6-Me | 2 | NO$_2$ | H | SMe | |

TABLE 1-continued

| Compound No. of present invention | (R)$_m$ | L | X | Y | Z | Chracteristic (Physical property) |
|---|---|---|---|---|---|---|
| 532 | 6-Me | 2 | NO$_2$ | H | CF$_3$ | |
| 533 | 6-Me | 2 | NO$_2$ | OMe | Cl | |
| 534 | 6-Me | 2 | NO$_2$ | OMe | CF$_3$ | |
| 535 | 6-Me | 2 | CF$_3$ | H | Cl | |
| 536 | 6-Me | 2 | CF$_3$ | H | Br | |
| 537 | 6-Me | 2 | CF$_3$ | H | SMe | |
| 538 | 6-Me | 2 | CF$_3$ | H | CF$_3$ | |
| 539 | 6-Me | 2 | OMe | H | Cl | |
| 540 | 6-Me | 2 | OMe | H | OMe | |
| 541 | 4.4-diMe | 0 | Cl | H | Cl | |
| 542 | 4.4-diMe | 0 | Cl | H | SO$_2$Me | |
| 543 | 4.4-diMe | 0 | Cl | H | NO$_2$ | |
| 544 | 4.4-diMe | 0 | Cl | H | OMe | |
| 545 | 4.4-diMe | 0 | Cl | H | Me | |
| 546 | 4.4-diMe | 0 | Cl | H | Br | |
| 547 | 4.4-diMe | 0 | Cl | H | F | |
| 548 | 4.4-diMe | O | Cl | H | SMe | |
| 549 | 4.4-diMe | 0 | Cl | H | S(O)Me | |
| 550 | 4.4-diMe | 0 | Cl | H | CF$_3$ | |
| 551 | 4.4-diMe | 0 | Cl | H | CN | |
| 552 | 4.4-diMe | 0 | Cl | Cl | Cl | |
| 553 | 4.4-diMe | 0 | Cl | Cl | OMe | |
| 554 | 4.4-diMe | 0 | Cl | Cl | SMe | |
| 555 | 4.4-diMe | 0 | Cl | Cl | SO$_2$Me | |
| 556 | 4.4-diMe | 0 | Cl | Me | Cl | |
| 557 | 4.4-diMe | 0 | Cl | Me | SO$_2$Me | |
| 558 | 4.4-diMe | 0 | Cl | OMe | Cl | |
| 559 | 4.4-diMe | 0 | Cl | OMe | Br | |
| 560 | 4.4-diMe | 0 | Cl | OMe | SO$_2$Me | |
| 561 | 4.4-diMe | 0 | Cl | OEt | Br | |
| 562 | 4.4-diMe | 0 | Br | H | OMe | |
| 563 | 4.4-diMe | 0 | F | H | F | |
| 564 | 4.4-diMe | 0 | I | I | I | |
| 565 | 4.4-diMe | 0 | Me | H | CN | |
| 566 | 4.4-diMe | 0 | Me | H | Me | |
| 567 | 4.4-diMe | 0 | Me | H | OMe | |
| 568 | 4.4-diMe | 0 | Me | Cl | Cl | |
| 569 | 4.4-diMe | 0 | Me | CO$_2$Me | SO$_2$Me | |
| 570 | 4.4-diMe | 0 | Me | CH$_2$OMe | SO$_2$Me | |
| 571 | 4.4-diMe | 0 | Me | CH(Me)OMe | SO$_2$Me | |
| 572 | 4.4-diMe | 0 | NO$_2$ | H | Cl | |
| 573 | 4.4-diMe | 0 | NO$_2$ | H | Br | |
| 574 | 4.4-diMe | 0 | NO$_2$ | H | F | |
| 575 | 4.4-diMe | 0 | NO$_2$ | H | CN | |
| 576 | 4.4-diMe | 0 | NO$_2$ | H | SMe | |
| 577 | 4.4-diMe | 0 | NO$_2$ | H | CF$_3$ | |
| 578 | 4.4-diMe | 0 | NO$_2$ | OMe | Cl | |
| 579 | 4.4-diMe | 0 | NO$_2$ | OMe | CF$_3$ | |
| 580 | 4.4-diMe | 0 | CF$_3$ | H | Cl | |
| 581 | 4.4-diMe | 0 | CF$_3$ | H | Br | |
| 582 | 4.4-diMe | 0 | CF$_3$ | H | SMe | |
| 583 | 4.4-diMe | 0 | CF$_3$ | H | CF$_3$ | |
| 584 | 4.4-diMe | 0 | OMe | H | Cl | |
| 585 | 4.4-diMe | 0 | OMe | H | OMe | |
| 586 | 4.4-diMe | 1 | Cl | H | Cl | |
| 587 | 4.4-diMe | 1 | Cl | H | SO$_2$Me | |
| 588 | 4.4-diMe | 1 | Cl | H | NO$_2$ | |
| 589 | 4.4-diMe | 1 | Cl | H | OMe | |
| 590 | 4.4-diMe | 1 | Cl | H | Me | |
| 591 | 4.4-diMe | 1 | Cl | H | Br | |
| 592 | 4.4-diMe | 1 | Cl | H | F | |
| 593 | 4.4-diMe | 1 | Cl | H | SMe | |
| 594 | 4.4-diMe | 1 | Cl | H | S(O)Me | |
| 595 | 4.4-diMe | 1 | Cl | H | CF$_3$ | |
| 596 | 4.4-diMe | 1 | Cl | H | CN | |
| 597 | 4.4-diMe | 1 | Cl | Cl | Cl | |
| 598 | 4.4-diMe | 1 | Cl | Cl | OMe | |
| 599 | 4.4-diMe | 1 | Cl | Cl | SMe | |
| 600 | 4.4-diMe | 1 | Cl | Cl | SO$_2$Me | |
| 601 | 4.4-diMe | 1 | Cl | Me | Cl | |
| 602 | 4.4-diMe | 1 | Cl | Me | SO$_2$Me | |

TABLE 1-continued

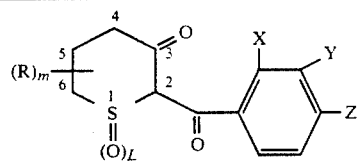

| Compound No. of present invention | (R)$_m$ | L | X | Y | Z | Chracteristic (Physical property) |
|---|---|---|---|---|---|---|
| 603 | 4.4-diMe | 1 | Cl | OMe | Cl | |
| 604 | 4.4-diMe | 1 | Cl | OMe | Br | |
| 605 | 4.4-diMe | 1 | Cl | OMe | SO$_2$Me | |
| 606 | 4.4-diMe | 1 | Cl | OEt | Br | |
| 607 | 4.4-diMe | 1 | Br | H | OMe | |
| 608 | 4.4-diMe | 1 | F | H | F | |
| 609 | 4.4-diMe | 1 | I | I | I | |
| 610 | 4.4-diMe | 1 | Me | H | CN | |
| 611 | 4.4-diMe | 1 | Me | H | Me | |
| 612 | 4.4-diMe | 1 | Me | H | OMe | |
| 613 | 4.4-diMe | 1 | Me | Cl | Cl | |
| 614 | 4.4-diMe | 1 | Me | CO$_2$Me | SO$_2$Me | |
| 615 | 4.4-diMe | 1 | Me | CH$_2$OMe | SO$_2$Me | |
| 616 | 4.4-diMe | 1 | Me | CH(Me)OMe | SO$_2$Me | |
| 617 | 4.4-diMe | 1 | NO$_2$ | H | Cl | |
| 618 | 4.4-diMe | 1 | NO$_2$ | H | Br | |
| 619 | 4.4-diMe | 1 | NO$_2$ | H | F | |
| 620 | 4.4-diMe | 1 | NO$_2$ | H | CN | |
| 621 | 4.4-diMe | 1 | NO$_2$ | H | SMe | |
| 622 | 4.4-diMe | 1 | NO$_2$ | H | CF$_3$ | |
| 623 | 4.4-diMe | 1 | NO$_2$ | OMe | Cl | |
| 624 | 4.4-diMe | 1 | NO$_2$ | OMe | CF$_3$ | |
| 625 | 4.4-diMe | 1 | CF$_3$ | H | Cl | |
| 626 | 4.4-diMe | 1 | CF$_3$ | H | Br | |
| 627 | 4.4-diMe | 1 | CF$_3$ | H | SMe | |
| 628 | 4.4-diMe | 1 | CF$_3$ | H | CF$_3$ | |
| 629 | 4.4-diMe | 1 | OMe | H | Cl | |
| 630 | 4.4-diMe | 1 | OMe | H | OMe | |
| 631 | 4.4-diMe | 2 | Cl | H | Cl | |
| 632 | 4.4-diMe | 2 | Cl | H | SO$_2$Me | |
| 633 | 4.4-diMe | 2 | Cl | H | NO$_2$ | |
| 634 | 4.4-diMe | 2 | Cl | H | OMe | |
| 635 | 4.4-diMe | 2 | Cl | H | Me | |
| 636 | 4.4-diMe | 2 | Cl | H | Br | |
| 637 | 4.4-diMe | 2 | Cl | H | F | |
| 638 | 4.4-diMe | 2 | Cl | H | SMe | |
| 639 | 4.4-diMe | 2 | Cl | H | S(O)Me | |
| 640 | 4.4-diMe | 2 | Cl | H | CF$_3$ | |
| 641 | 4.4-diMe | 2 | Cl | H | CN | |
| 642 | 4.4-diMe | 2 | Cl | Cl | Cl | |
| 643 | 4.4-diMe | 2 | Cl | Cl | OMe | |
| 644 | 4.4-diMe | 2 | Cl | Cl | SMe | |
| 645 | 4.4-diMe | 2 | Cl | Cl | SO$_2$Me | |
| 646 | 4.4-diMe | 2 | Cl | Me | Cl | |
| 647 | 4.4-diMe | 2 | Cl | Me | SO$_2$Me | |
| 648 | 4.4-diMe | 2 | Cl | OMe | Cl | |
| 649 | 4.4-diMe | 2 | Cl | OMe | Br | |
| 650 | 4.4-diMe | 2 | Cl | OMe | SO$_2$Me | |
| 651 | 4.4-diMe | 2 | Cl | OEt | Br | |
| 652 | 4.4-diMe | 2 | Br | H | OMe | |
| 653 | 4.4-diMe | 2 | F | H | F | |
| 654 | 4.4-diMe | 2 | I | I | I | |
| 655 | 4.4-diMe | 2 | Me | H | CN | |
| 656 | 4.4-diMe | 2 | Me | H | Me | |
| 657 | 4.4-diMe | 2 | Me | H | OMe | |
| 658 | 4.4-diMe | 2 | Me | Cl | Cl | |
| 659 | 4.4-diMe | 2 | Me | CO$_2$Me | SO$_2$Me | |
| 660 | 4.4-diMe | 2 | Me | CH$_2$OMe | SO$_2$Me | |
| 661 | 4.4-diMe | 2 | Me | CH(Me)OMe | SO$_2$Me | |
| 662 | 4.4-diMe | 2 | NO$_2$ | H | Cl | |
| 663 | 4.4-diMe | 2 | NO$_2$ | H | Br | |
| 664 | 4.4-diMe | 2 | NO$_2$ | H | F | |
| 665 | 4.4-diMe | 2 | NO$_2$ | H | CN | |
| 666 | 4.4-diMe | 2 | NO$_2$ | H | SMe | |
| 667 | 4.4-diMe | 2 | NO$_2$ | H | CF$_3$ | |
| 668 | 4.4-diMe | 2 | NO$_2$ | OMe | Cl | |
| 669 | 4.4-diMe | 2 | NO$_2$ | OMe | CF$_3$ | |
| 670 | 4.4-diMe | 2 | CF$_3$ | H | Cl | |
| 671 | 4.4-diMe | 2 | CF$_3$ | H | Br | |
| 672 | 4.4-diMe | 2 | CF$_3$ | H | SMe | |
| 673 | 4.4-diMe | 2 | CF$_3$ | H | CF$_3$ | |

TABLE 1-continued

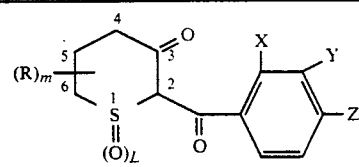

| Compound No. of present invention | (R)$_m$ | L | X | Y | Z | Chracteristic (Physical property) |
|---|---|---|---|---|---|---|
| 674 | 4.4-diMe | 2 | OMe | H | Cl | |
| 675 | 4.4-diMe | 2 | OMe | H | OMe | |
| 676 | 5.5-diMe | 0 | Cl | H | Cl | |
| 677 | 5.5-diMe | 0 | Cl | H | SO$_2$Me | |
| 678 | 5.5-diMe | 0 | Cl | H | NO$_2$ | |
| 679 | 5.5-diMe | 0 | Cl | H | OMe | |
| 680 | 5.5-diMe | 0 | Cl | H | Me | |
| 681 | 5.5-diMe | 0 | Cl | H | Br | |
| 682 | 5.5-diMe | 0 | Cl | H | F | |
| 683 | 5.5-diMe | 0 | Cl | H | SMe | |
| 684 | 5.5-diMe | 0 | Cl | H | S(O)Me | |
| 685 | 5.5-diMe | 0 | Cl | H | CF$_3$ | |
| 686 | 5.5-diMe | 0 | Cl | H | CN | |
| 687 | 5.5-diMe | 0 | Cl | Cl | Cl | |
| 688 | 5.5-diMe | 0 | Cl | Cl | OMe | |
| 689 | 5.5-diMe | 0 | Cl | Cl | SMe | |
| 690 | 5.5-diMe | 0 | Cl | Cl | SO$_2$Me | |
| 691 | 5.5-diMe | 0 | Cl | Me | Cl | |
| 692 | 5.5-diMe | 0 | Cl | Me | SO$_2$Me | |
| 693 | 5.5-diMe | 0 | Cl | OMe | Cl | |
| 694 | 5.5-diMe | 0 | Cl | OMe | Br | |
| 695 | 5.5-diMe | 0 | Cl | OMe | SO$_2$Me | |
| 696 | 5.5-diMe | 0 | Cl | OEt | Br | |
| 697 | 5.5-diMe | 0 | Br | H | OMe | |
| 698 | 5.5-diMe | 0 | F | H | F | |
| 699 | 5.5-diMe | 0 | I | I | I | |
| 700 | 5.5-diMe | 0 | Me | H | CN | |
| 701 | 5.5-diMe | 0 | Me | H | Me | |
| 702 | 5.5-diMe | 0 | Me | H | OMe | |
| 703 | 5.5-diMe | 0 | Me | Cl | Cl | |
| 704 | 5.5-diMe | 0 | Me | CO$_2$Me | SO$_2$Me | |
| 705 | 5.5-diMe | 0 | Me | CH$_2$OMe | SO$_2$Me | |
| 706 | 5.5-diMe | 0 | Me | CH(Me)OMe | SO$_2$Me | |
| 707 | 5.5-diMe | 0 | NO$_2$ | H | Cl | |
| 708 | 5.5-diMe | 0 | NO$_2$ | H | Br | |
| 709 | 5.5-diMe | 0 | NO$_2$ | H | F | |
| 710 | 5.5-diMe | 0 | NO$_2$ | H | CN | |
| 711 | 5.5-diMe | 0 | NO$_2$ | H | SMe | |
| 712 | 5.5-diMe | 0 | NO$_2$ | H | CF$_3$ | |
| 713 | 5.5-diMe | 0 | NO$_2$ | OMe | Cl | |
| 714 | 5.5-diMe | 0 | NO$_2$ | OMe | CF$_3$ | |
| 715 | 5.5-diMe | 0 | CF$_3$ | H | Cl | |
| 716 | 5.5-diMe | 0 | CF$_3$ | H | Br | |
| 717 | 5.5-diMe | 0 | CF$_3$ | H | SMe | |
| 718 | 5.5-diMe | 0 | CF$_3$ | H | CF$_3$ | |
| 719 | 5.5-diMe | 0 | OMe | H | Cl | |
| 720 | 5.5-diMe | 0 | OMe | H | OMe | |
| 721 | 5.5-diMe | 1 | Cl | H | Cl | |
| 722 | 5.5-diMe | 1 | Cl | H | SO$_2$Me | |
| 723 | 5.5-diMe | 1 | Cl | H | NO$_2$ | |
| 724 | 5.5-diMe | 1 | Cl | H | OMe | |
| 725 | 5.5-diMe | 1 | Cl | H | Me | |
| 726 | 5.5-diMe | 1 | Cl | H | Br | |
| 727 | 5.5-diMe | 1 | Cl | H | F | |
| 728 | 5.5-diMe | 1 | Cl | H | SMe | |
| 729 | 5.5-diMe | 1 | Cl | H | S(O)Me | |
| 730 | 5.5-diMe | 1 | Cl | H | CF$_3$ | |
| 731 | 5.5-diMe | 1 | Cl | H | CN | |
| 732 | 5.5-diMe | 1 | Cl | Cl | Cl | |
| 733 | 5.5-diMe | 1 | Cl | Cl | OMe | |
| 734 | 5.5-diMe | 1 | Cl | Cl | SMe | |
| 735 | 5.5-diMe | 1 | Cl | Cl | SO$_2$Me | |
| 736 | 5.5-diMe | 1 | Cl | Me | Cl | |
| 737 | 5.5-diMe | 1 | Cl | Me | SO$_2$Me | |
| 738 | 5.5-diMe | 1 | Cl | OMe | Cl | |
| 739 | 5.5-diMe | 1 | Cl | OMe | Br | |
| 740 | 5.5-diMe | 1 | Cl | OMe | SO$_2$Me | |
| 741 | 5.5-diMe | 1 | Cl | OEt | Br | |
| 742 | 5.5-diMe | 1 | Br | H | OMe | |
| 743 | 5.5-diMe | 1 | F | H | F | |
| 744 | 5.5-diMe | 1 | I | I | I | |

TABLE 1-continued

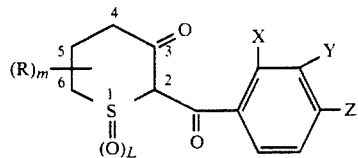

| Compound No. of present invention | (R)$_m$ | L | X | Y | Z | Charateristic (Physical property) |
|---|---|---|---|---|---|---|
| 745 | 5,5-diMe | 1 | Me | H | CN | |
| 746 | 5,5-diMe | 1 | Me | H | Me | |
| 747 | 5,5-diMe | 1 | Me | H | OMe | |
| 748 | 5,5-diMe | 1 | Me | Cl | Cl | |
| 749 | 5,5-diMe | 1 | Me | CO$_2$Me | SO$_2$Me | |
| 750 | 5,5-diMe | 1 | Me | CH$_2$OMe | SO$_2$Me | |
| 751 | 5,5-diMe | 1 | Me | CH(Me)OMe | SO$_2$Me | |
| 752 | 5,5-diMe | 1 | NO$_2$ | H | Cl | |
| 753 | 5,5-diMe | 1 | NO$_2$ | H | Br | |
| 754 | 5,5-diMe | 1 | NO$_2$ | H | F | |
| 755 | 5,5-diMe | 1 | NO$_2$ | H | CN | |
| 756 | 5,5-diMe | 1 | NO$_2$ | H | SMe | |
| 757 | 5,5-diMe | 1 | NO$_2$ | H | CF$_3$ | |
| 758 | 5,5-diMe | 1 | NO$_2$ | OMe | Cl | |
| 759 | 5,5-diMe | 1 | NO$_2$ | OMe | CF$_3$ | |
| 760 | 5,5-diMe | 1 | CF$_3$ | H | Cl | |
| 761 | 5,5-diMe | 1 | CF$_3$ | H | Br | |
| 762 | 5,5-diMe | 1 | CF$_3$ | H | SMe | |
| 763 | 5,5-diMe | 1 | CF$_3$ | H | CF$_3$ | |
| 764 | 5,5-diMe | 1 | OMe | H | Cl | |
| 765 | 5,5-diMe | 1 | OMe | H | OMe | |
| 766 | 5,5-diMe | 2 | Cl | H | Cl | |
| 767 | 5,5-diMe | 2 | Cl | H | SO$_2$Me | |
| 768 | 5,5-diMe | 2 | Cl | H | NO$_2$ | |
| 769 | 5,5-diMe | 2 | Cl | H | OMe | |
| 770 | 5,5-diMe | 2 | Cl | H | Me | |
| 771 | 5,5-diMe | 2 | Cl | H | Br | |
| 772 | 5,5-diMe | 2 | Cl | H | F | |
| 773 | 5,5-diMe | 2 | Cl | H | SMe | |
| 774 | 5,5-diMe | 2 | Cl | H | S(O)Me | |
| 775 | 5,5-diMe | 2 | Cl | H | CF$_3$ | |
| 776 | 5,5-diMe | 2 | Cl | H | CN | |
| 777 | 5,5-diMe | 2 | Cl | Cl | Cl | |
| 778 | 5,5-diMe | 2 | Cl | Cl | OMe | |
| 779 | 5,5-diMe | 2 | Cl | Cl | SMe | |
| 780 | 5,5-diMe | 2 | Cl | Cl | SO$_2$Me | |
| 781 | 5,5-diMe | 2 | Cl | Me | Cl | |
| 782 | 5,5-diMe | 2 | Cl | Me | SO$_2$Me | |
| 783 | 5,5-diMe | 2 | Cl | OMe | Cl | |
| 784 | 5,5-diMe | 2 | Cl | OMe | Br | |
| 785 | 5,5-diMe | 2 | Cl | OMe | SO$_2$Me | |
| 786 | 5,5-diMe | 2 | Cl | OEt | Br | |
| 787 | 5,5-diMe | 2 | Br | H | OMe | |
| 788 | 5,5-diMe | 2 | F | H | F | |
| 789 | 5,5-diMe | 2 | I | I | I | |
| 790 | 5,5-diMe | 2 | Me | H | CN | |
| 791 | 5,5-diMe | 2 | Me | H | Me | |
| 792 | 5,5-diMe | 2 | Me | H | OMe | |
| 793 | 5,5-diMe | 2 | Me | Cl | Cl | |
| 794 | 5,5-diMe | 2 | Me | CO$_2$Me | SO$_2$Me | |
| 795 | 5,5-diMe | 2 | Me | CH$_2$OMe | SO$_2$Me | |
| 796 | 5,5-diMe | 2 | Me | CH(Me)OMe | SO$_2$Me | |
| 797 | 5,5-diMe | 2 | NO$_2$ | H | Cl | |
| 798 | 5,5-diMe | 2 | NO$_2$ | H | Br | |
| 799 | 5,5-diMe | 2 | NO$_2$ | H | F | |
| 800 | 5,5-diMe | 2 | NO$_2$ | H | CN | |
| 801 | 5,5-diMe | 2 | NO$_2$ | H | SMe | |
| 802 | 5,5-diMe | 2 | NO$_2$ | H | CF$_3$ | |
| 803 | 5,5-diMe | 2 | NO$_2$ | OMe | Cl | |
| 804 | 5,5-diMe | 2 | NO$_2$ | OMe | CF$_3$ | |
| 805 | 5,5-diMe | 2 | CF$_3$ | H | Cl | |
| 806 | 5,5-diMe | 2 | CF$_3$ | H | Br | |
| 807 | 5,5-diMe | 2 | CF$_3$ | H | SMe | |
| 808 | 5,5-diMe | 2 | CF$_3$ | H | CF$_3$ | |
| 809 | 5,5-diMe | 2 | OMe | H | Cl | |
| 810 | 5,5-diMe | 2 | OMe | H | OMe | |
| 811 | 6,6-diMe | 0 | Cl | H | Cl | |
| 812 | 6,6-diMe | 0 | Cl | H | SO$_2$Me | |
| 813 | 6,6-diMe | 0 | Cl | H | NO$_2$ | |
| 814 | 6,6-diMe | 0 | Cl | H | OMe | |
| 815 | 6,6-diMe | 0 | Cl | H | Me | |

TABLE 1-continued

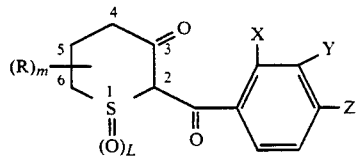

| Compound No. of present invention | (R)$_m$ | L | X | Y | Z | Characteristic (Physical property) |
|---|---|---|---|---|---|---|
| 816 | 6.6-diMe | 0 | Cl | H | Br | |
| 817 | 6.6-diMe | 0 | Cl | H | F | |
| 818 | 6.6-diMe | 0 | Cl | H | SMe | |
| 819 | 6.6-diMe | 0 | Cl | H | S(O)Me | |
| 820 | 6.6-diMe | 0 | Cl | H | CF$_3$ | |
| 821 | 6.6-diMe | 0 | Cl | H | CN | |
| 822 | 6.6-diMe | 0 | Cl | Cl | Cl | |
| 823 | 6.6-diMe | 0 | Cl | Cl | OMe | |
| 824 | 6.6-diMe | 0 | Cl | Cl | SMe | |
| 825 | 6.6-diMe | 0 | Cl | Cl | SO$_2$Me | |
| 826 | 6.6-diMe | 0 | Cl | Me | Cl | |
| 827 | 6.6-diMe | 0 | Cl | Me | SO$_2$Me | |
| 828 | 6.6-diMe | 0 | Cl | OMe | Cl | |
| 829 | 6.6-diMe | 0 | Cl | OMe | Br | |
| 830 | 6.6-diMe | 0 | Cl | OMe | SO$_2$Me | |
| 831 | 6.6-diMe | 0 | Cl | OEt | Br | |
| 832 | 6.6-diMe | 0 | Br | H | OMe | |
| 833 | 6.6-diMe | 0 | F | H | F | |
| 834 | 6.6-diMe | 0 | I | I | I | |
| 835 | 6.6-diMe | 0 | Me | H | CN | |
| 836 | 6.6-diMe | 0 | Me | H | Me | |
| 837 | 6.6-diMe | 0 | Me | H | OMe | |
| 838 | 6.6-diMe | 0 | Me | Cl | Cl | |
| 839 | 6.6-diMe | 0 | Me | CO$_2$Me | SO$_2$Me | |
| 840 | 6.6-diMe | 0 | Me | CH$_2$OMe | SO$_2$Me | |
| 841 | 6.6-diMe | 0 | Me | CH(Me)OMe | SO$_2$Me | |
| 842 | 6.6-diMe | 0 | NO$_2$ | H | Cl | |
| 843 | 6.6-diMe | 0 | NO$_2$ | H | Br | |
| 844 | 6.6-diMe | 0 | NO$_2$ | H | F | |
| 845 | 6.6-diMe | 0 | NO$_2$ | H | CN | |
| 846 | 6.6-diMe | 0 | NO$_2$ | H | SMe | |
| 847 | 6.6-diMe | 0 | NO$_2$ | H | CF$_3$ | |
| 848 | 6.6-diMe | 0 | NO$_2$ | OMe | Cl | |
| 849 | 6.6-diMe | 0 | NO$_2$ | OMe | CF$_3$ | |
| 850 | 6.6-diMe | 0 | CF$_3$ | H | Cl | |
| 851 | 6.6-diMe | 0 | CF$_3$ | H | Br | |
| 852 | 6.6-diMe | 0 | CF$_3$ | H | SMe | |
| 853 | 6.6-diMe | 0 | CF$_3$ | H | CF$_3$ | |
| 854 | 6.6-diMe | 0 | OMe | H | Cl | |
| 855 | 6.6-diMe | 0 | OMe | H | OMe | |
| 856 | 6.6-diMe | 1 | Cl | H | Cl | |
| 857 | 6.6-diMe | 1 | Cl | H | SO$_2$Me | |
| 858 | 6.6-diMe | 1 | Cl | H | NO$_2$ | |
| 859 | 6.6-diMe | 1 | Cl | H | OMe | |
| 860 | 6.6-diMe | 1 | Cl | H | Me | |
| 861 | 6.6-diMe | 1 | Cl | H | Br | |
| 862 | 6.6-diMe | 1 | Cl | H | F | |
| 863 | 6.6-diMe | 1 | Cl | H | SMe | |
| 864 | 6.6-diMe | 1 | Cl | H | S(O)Me | |
| 865 | 6.6-diMe | 1 | Cl | H | CF$_3$ | |
| 866 | 6.6-diMe | 1 | Cl | H | CN | |
| 867 | 6.6-diMe | 1 | Cl | Cl | Cl | |
| 868 | 6.6-diMe | 1 | Cl | Cl | OMe | |
| 869 | 6.6-diMe | 1 | Cl | Cl | SMe | |
| 870 | 6.6-diMe | 1 | Cl | Cl | SO$_2$Me | |
| 871 | 6.6-diMe | 1 | Cl | Me | Cl | |
| 872 | 6.6-diMe | 1 | Cl | Me | SO$_2$Me | |
| 873 | 6.6-diMe | 1 | Cl | OMe | Cl | |
| 874 | 6.6-diMe | 1 | Cl | OMe | Br | |
| 875 | 6.6-diMe | 1 | Cl | OMe | SO$_2$Me | |
| 876 | 6.6-diMe | 1 | Cl | OEt | Br | |
| 877 | 6.6-diMe | 1 | Br | H | OMe | |
| 878 | 6.6-diMe | 1 | F | H | F | |
| 879 | 6.6-diMe | 1 | I | I | I | |
| 880 | 6.6-diMe | 1 | Me | H | CN | |
| 881 | 6.6-diMe | 1 | Me | H | Me | |
| 882 | 6.6-diMe | 1 | Me | H | OMe | |
| 883 | 6.6-diMe | 1 | Me | Cl | Cl | |
| 884 | 6.6-diMe | 1 | Me | CO$_2$Me | SO$_2$Me | |
| 885 | 6.6-diMe | 1 | Me | CH$_2$OMe | SO$_2$Me | |
| 886 | 6.6-diMe | 1 | Me | CH(Me)OMe | SO$_2$Me | |

TABLE 1-continued

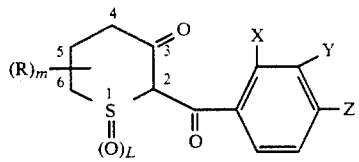

| Compound No. of present invention | (R)$_m$ | L | X | Y | Z | Charcteristic (Physical property) |
|---|---|---|---|---|---|---|
| 887 | 6.6-diMe | 1 | NO$_2$ | H | Cl | |
| 888 | 6.6-diMe | 1 | NO$_2$ | H | Br | |
| 889 | 6.6-diMe | 1 | NO$_2$ | H | F | |
| 890 | 6.6-diMe | 1 | NO$_2$ | H | CN | |
| 891 | 6.6-diMe | 1 | NO$_2$ | H | SMe | |
| 892 | 6.6-diMe | 1 | NO$_2$ | H | CF$_3$ | |
| 893 | 6.6-diMe | 1 | NO$_2$ | OMe | Cl | |
| 894 | 6.6-diMe | 1 | NO$_2$ | OMe | CF$_3$ | |
| 895 | 6.6-diMe | 1 | CF$_3$ | H | Cl | |
| 896 | 6.6-diMe | 1 | CF$_3$ | H | Br | |
| 897 | 6.6-diMe | 1 | CF$_3$ | H | SMe | |
| 898 | 6.6-diMe | 1 | CF$_3$ | H | CF$_3$ | |
| 899 | 6.6-diMe | 1 | OMe | H | Cl | |
| 900 | 6.6-diMe | 1 | OMe | H | OMe | |
| 901 | 6.6-diMe | 2 | Cl | H | Cl | |
| 902 | 6.6-diMe | 2 | Cl | H | SO$_2$Me | |
| 903 | 6.6-diMe | 2 | Cl | H | NO$_2$ | |
| 904 | 6.6-diMe | 2 | Cl | H | OMe | |
| 905 | 6.6-diMe | 2 | Cl | H | Me | |
| 906 | 6.6-diMe | 2 | Cl | H | Br | |
| 907 | 6.6-diMe | 2 | Cl | H | F | |
| 908 | 6.6-diMe | 2 | Cl | H | SMe | |
| 909 | 6.6-diMe | 2 | Cl | H | S(O)Me | |
| 910 | 6.6-diMe | 2 | Cl | H | CF$_3$ | |
| 911 | 6.6-diMe | 2 | Cl | H | CN | |
| 912 | 6.6-diMe | 2 | Cl | Cl | Cl | |
| 913 | 6.6-diMe | 2 | Cl | Cl | OMe | |
| 914 | 6.6-diMe | 2 | Cl | Cl | SMe | |
| 915 | 6.6-diMe | 2 | Cl | Cl | SO$_2$Me | |
| 916 | 6.6-diMe | 2 | Cl | Me | Cl | |
| 917 | 6.6-diMe | 2 | Cl | Me | SO$_2$Me | |
| 918 | 6.6-diMe | 2 | Cl | OMe | Cl | |
| 919 | 6.6-diMe | 2 | Cl | OMe | Br | |
| 920 | 6.6-diMe | 2 | Cl | OMe | SO$_2$Me | |
| 921 | 6.6-diMe | 2 | Cl | OEt | Br | |
| 922 | 6.6-diMe | 2 | Br | H | OMe | |
| 923 | 6.6-diMe | 2 | F | H | F | |
| 924 | 6.6-diMe | 2 | I | I | I | |
| 925 | 6.6-diMe | 2 | Me | H | CN | |
| 926 | 6.6-diMe | 2 | Me | H | Me | |
| 927 | 6.6-diMe | 2 | Me | H | OMe | |
| 928 | 6.6-diMe | 2 | Me | Cl | Cl | |
| 929 | 6.6-diMe | 2 | Me | CO$_2$Me | SO$_2$Me | |
| 930 | 6.6-diMe | 2 | Me | CH$_2$OMe | SO$_2$Me | |
| 931 | 6.6-diMe | 2 | Me | CH(Me)OMe | SO$_2$Me | |
| 932 | 6.6-diMe | 2 | NO$_2$ | H | Cl | |
| 933 | 6.6-diMe | 2 | NO$_2$ | H | Br | |
| 934 | 6.6-diMe | 2 | NO$_2$ | H | F | |
| 935 | 6.6-diMe | 2 | NO$_2$ | H | CN | |
| 936 | 6.6-diMe | 2 | NO$_2$ | H | SMe | |
| 937 | 6.6-diMe | 2 | NO$_2$ | H | CF$_3$ | |
| 938 | 6.6-diMe | 2 | NO$_2$ | OMe | Cl | |
| 939 | 6.6-diMe | 2 | NO$_2$ | OMe | CF$_3$ | |
| 940 | 6.6-diMe | 2 | CF$_3$ | H | Cl | |
| 941 | 6.6-diMe | 2 | CF$_3$ | H | Br | |
| 942 | 6.6-diMe | 2 | CF$_3$ | H | SMe | |
| 943 | 6.6-diMe | 2 | CF$_3$ | H | CF$_3$ | |
| 944 | 6.6-diMe | 2 | OMe | H | Cl | |
| 945 | 6.6-diMe | 2 | OMe | H | OMe | |
| 946 | 4-Ph | 0 | Cl | H | Cl | |
| 947 | 4-Ph | 0 | Cl | H | SO$_2$Me | |
| 948 | 4-Ph | 0 | Cl | H | NO$_2$ | |
| 949 | 4-Ph | 0 | Cl | H | OMe | |
| 950 | 4-Ph | 0 | Cl | H | Me | |
| 951 | 4-Ph | 0 | Cl | H | Br | |
| 952 | 4-Ph | 0 | Cl | H | F | |
| 953 | 4-Ph | 0 | Cl | H | SMe | |
| 954 | 4-Ph | 0 | Cl | H | S(O)Me | |
| 955 | 4-Ph | 0 | Cl | H | CF$_3$ | |
| 956 | 4-Ph | 0 | Cl | H | CN | |
| 957 | 4-Ph | 0 | Cl | Cl | Cl | |

TABLE 1-continued

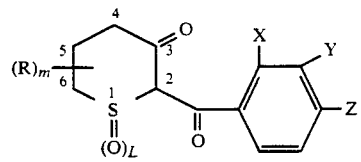

| Compound No. of present invention | (R)$_m$ | L | X | Y | Z | Chracteristic (Physical property) |
|---|---|---|---|---|---|---|
| 958 | 4-Ph | 0 | Cl | Cl | OMe | |
| 959 | 4-Ph | 0 | Cl | Cl | SMe | |
| 960 | 4-Ph | 0 | Cl | Cl | SO$_2$Me | |
| 961 | 4-Ph | 0 | Cl | Me | Cl | |
| 962 | 4-Ph | 0 | Cl | Me | SO$_2$Me | |
| 963 | 4-Ph | 0 | Cl | OMe | Cl | |
| 964 | 4-Ph | 0 | Cl | OMe | Br | |
| 965 | 4-Ph | 0 | Cl | OMe | SO$_2$Me | |
| 966 | 4-Ph | 0 | Cl | OEt | Br | |
| 967 | 4-Ph | 0 | Br | H | OMe | |
| 968 | 4-Ph | 0 | F | H | F | |
| 969 | 4-Ph | 0 | I | I | I | |
| 970 | 4-Ph | 0 | Me | H | CN | |
| 971 | 4-Ph | 0 | Me | H | Me | |
| 972 | 4-Ph | 0 | Me | H | OMe | |
| 973 | 4-Ph | 0 | Me | Cl | Cl | |
| 974 | 4-Ph | 0 | Me | CO$_2$Me | SO$_2$Me | |
| 975 | 4-Ph | 0 | Me | CH$_2$OMe | SO$_2$Me | |
| 976 | 4-Ph | 0 | Me | CH(Me)OMe | SO$_2$Me | |
| 977 | 4-Ph | 0 | NO$_2$ | H | Cl | |
| 978 | 4-Ph | 0 | NO$_2$ | H | Br | |
| 979 | 4-Ph | 0 | NO$_2$ | H | F | |
| 980 | 4-Ph | 0 | NO$_2$ | H | CN | |
| 981 | 4-Ph | 0 | NO$_2$ | H | SMe | |
| 982 | 4-Ph | 0 | NO$_2$ | H | CF$_3$ | |
| 983 | 4-Ph | 0 | NO$_2$ | OMe | Cl | |
| 984 | 4-Ph | 0 | NO$_2$ | OMe | CF$_3$ | |
| 985 | 4-Ph | 0 | CF$_3$ | H | Cl | |
| 986 | 4-Ph | 0 | CF$_3$ | H | Br | |
| 987 | 4-Ph | 0 | CF$_3$ | H | SMe | |
| 988 | 4-Ph | 0 | CF$_3$ | H | CF$_3$ | |
| 989 | 4-Ph | 0 | OMe | H | Cl | |
| 990 | 4-Ph | 0 | OMe | H | OMe | |
| 991 | 4-Ph | 1 | Cl | H | Cl | |
| 992 | 4-Ph | 1 | Cl | H | SO$_2$Me | |
| 993 | 4-Ph | 1 | Cl | H | NO$_2$ | |
| 994 | 4-Ph | 1 | Cl | H | OMe | |
| 995 | 4-Ph | 1 | Cl | H | Me | |
| 996 | 4-Ph | 1 | Cl | H | Br | |
| 997 | 4-Ph | 1 | Cl | H | F | |
| 998 | 4-Ph | 1 | Cl | H | SMe | |
| 999 | 4-Ph | 1 | Cl | H | S(O)Me | |
| 1000 | 4-Ph | 1 | Cl | H | CF$_3$ | |
| 1001 | 4-Ph | 1 | Cl | H | CN | |
| 1002 | 4-Ph | 1 | Cl | Cl | Cl | |
| 1003 | 4-Ph | 1 | Cl | Cl | OMe | |
| 1004 | 4-Ph | 1 | Cl | Cl | SMe | |
| 1005 | 4-Ph | 1 | Cl | Cl | SO$_2$Me | |
| 1006 | 4-Ph | 1 | Cl | Me | Cl | |
| 1007 | 4-Ph | 1 | Cl | Me | SO$_2$Me | |
| 1008 | 4-Ph | 1 | Cl | OMe | Cl | |
| 1009 | 4-Ph | 1 | Cl | OMe | Br | |
| 1010 | 4-Ph | 1 | Cl | OMe | SO$_2$Me | |
| 1011 | 4-Ph | 1 | Cl | OEt | Br | |
| 1012 | 4-Ph | 1 | Br | H | OMe | |
| 1013 | 4-Ph | 1 | F | H | F | |
| 1014 | 4-Ph | 1 | I | I | I | |
| 1015 | 4-Ph | 1 | Me | H | CN | |
| 1016 | 4-Ph | 1 | Me | H | Me | |
| 1017 | 4-Ph | 1 | Me | H | OMe | |
| 1018 | 4-Ph | 1 | Me | Cl | Cl | |
| 1019 | 4-Ph | 1 | Me | CO$_2$Me | SO$_2$Me | |
| 1020 | 4-Ph | 1 | Me | CH$_2$OMe | SO$_2$Me | |
| 1021 | 4-Ph | 1 | Me | CH(Me)OMe | SO$_2$Me | |
| 1022 | 4-Ph | 1 | NO$_2$ | H | Cl | |
| 1023 | 4-Ph | 1 | NO$_2$ | H | Br | |
| 1024 | 4-Ph | 1 | NO$_2$ | H | F | |
| 1025 | 4-Ph | 1 | NO$_2$ | H | CN | |
| 1026 | 4-Ph | 1 | NO$_2$ | H | SMe | |
| 1027 | 4-Ph | 1 | NO$_2$ | H | CF$_3$ | |
| 1028 | 4-Ph | 1 | NO$_2$ | OMe | Cl | |

TABLE 1-continued

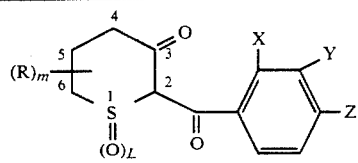

| Compound No. of present invention | (R)$_m$ | L | X | Y | Z | Characteristic (Physical property) |
|---|---|---|---|---|---|---|
| 1029 | 4-Ph | 1 | NO$_2$ | OMe | CF$_3$ | |
| 1030 | 4-Ph | 1 | CF$_3$ | H | Cl | |
| 1031 | 4-Ph | 1 | CF$_3$ | H | Br | |
| 1032 | 4-Ph | 1 | CF$_3$ | H | SMe | |
| 1033 | 4-Ph | 1 | CF$_3$ | H | CF$_3$ | |
| 1034 | 4-Ph | 1 | OMe | H | Cl | |
| 1035 | 4-Ph | 1 | OMe | H | OMe | |
| 1036 | 4-Ph | 2 | Cl | H | Cl | |
| 1037 | 4-Ph | 2 | Cl | H | SO$_2$Me | |
| 1038 | 4-Ph | 2 | Cl | H | NO$_2$ | |
| 1039 | 4-Ph | 2 | Cl | H | OMe | |
| 1040 | 4-Ph | 2 | Cl | H | Me | |
| 1041 | 4-Ph | 2 | Cl | H | Br | |
| 1042 | 4-Ph | 2 | Cl | H | F | |
| 1043 | 4-Ph | 2 | Cl | H | SMe | |
| 1044 | 4-Ph | 2 | Cl | H | S(O)Me | |
| 1045 | 4-Ph | 2 | Cl | H | CF$_3$ | |
| 1046 | 4-Ph | 2 | Cl | H | CN | |
| 1047 | 4-Ph | 2 | Cl | Cl | Cl | |
| 1048 | 4-Ph | 2 | Cl | Cl | OMe | |
| 1049 | 4-Ph | 2 | Cl | Cl | SMe | |
| 1050 | 4-Ph | 2 | Cl | Cl | SO$_2$Me | |
| 1051 | 4-Ph | 2 | Cl | Me | Cl | |
| 1052 | 4-Ph | 2 | Cl | Me | SO$_2$Me | |
| 1053 | 4-Ph | 2 | Cl | OMe | Cl | |
| 1054 | 4-Ph | 2 | Cl | OMe | Br | |
| 1055 | 4-Ph | 2 | Cl | OMe | SO$_2$Me | |
| 1056 | 4-Ph | 2 | Cl | OEt | Br | |
| 1057 | 4-Ph | 2 | Br | H | OMe | |
| 1058 | 4-Ph | 2 | F | H | F | |
| 1059 | 4-Ph | 2 | I | I | I | |
| 1060 | 4-Ph | 2 | Me | H | CN | |
| 1061 | 4-Ph | 2 | Me | H | Me | |
| 1062 | 4-Ph | 2 | Me | H | OMe | |
| 1063 | 4-Ph | 2 | Me | Cl | Cl | |
| 1064 | 4-Ph | 2 | Me | CO$_2$Me | SO$_2$Me | |
| 1065 | 4-Ph | 2 | Me | CH$_2$OMe | SO$_2$Me | |
| 1066 | 4-Ph | 2 | Me | CH(Me)OMe | SO$_2$Me | |
| 1067 | 4-Ph | 2 | NO$_2$ | H | Cl | |
| 1068 | 4-Ph | 2 | NO$_2$ | H | Br | |
| 1069 | 4-Ph | 2 | NO$_2$ | H | F | |
| 1070 | 4-Ph | 2 | NO$_2$ | H | CN | |
| 1071 | 4-Ph | 2 | NO$_2$ | H | SMe | |
| 1072 | 4-Ph | 2 | NO$_2$ | H | CF$_3$ | |
| 1073 | 4-Ph | 2 | NO$_2$ | OMe | Cl | |
| 1074 | 4-Ph | 2 | NO$_2$ | OMe | CF$_3$ | |
| 1075 | 4-Ph | 2 | CF$_3$ | H | Cl | |
| 1076 | 4-Ph | 2 | CF$_3$ | H | Br | |
| 1077 | 4-Ph | 2 | CF$_3$ | H | SMe | |
| 1078 | 4-Ph | 2 | CF$_3$ | H | CF$_3$ | |
| 1079 | 4-Ph | 2 | OMe | H | Cl | |
| 1080 | 4-Ph | 2 | OMe | H | OMe | |
| 1081 | 5-Ph | 0 | Cl | H | Cl | |
| 1082 | 5-Ph | 0 | Cl | H | SO$_2$Me | |
| 1083 | 5-Ph | 0 | Cl | H | NO$_2$ | |
| 1084 | 5-Ph | 0 | Cl | H | OMe | |
| 1085 | 5-Ph | 0 | Cl | H | Me | |
| 1086 | 5-Ph | 0 | Cl | H | Br | |
| 1087 | 5-Ph | 0 | Cl | H | F | |
| 1088 | 5-Ph | 0 | Cl | H | SMe | |
| 1089 | 5-Ph | 0 | Cl | H | S(O)Me | |
| 1090 | 5-Ph | 0 | Cl | H | CF$_3$ | |
| 1091 | 5-Ph | 0 | Cl | H | CN | |
| 1092 | 5-Ph | 0 | Cl | Cl | Cl | |
| 1093 | 5-Ph | 0 | Cl | Cl | OMe | |
| 1094 | 5-Ph | 0 | Cl | Cl | SMe | |
| 1095 | 5-Ph | 0 | Cl | Cl | SO$_2$Me | |
| 1096 | 5-Ph | 0 | Cl | Me | Cl | |
| 1097 | 5-Ph | 0 | Cl | Me | SO$_2$Me | |
| 1098 | 5-Ph | 0 | Cl | OMe | Cl | |
| 1099 | 5-Ph | 0 | Cl | OMe | Br | |

TABLE 1-continued

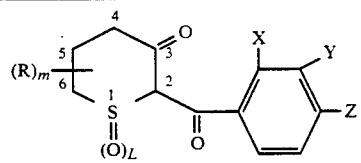

| Compound No. of present invention | (R)$_m$ | L | X | Y | Z | Chracteristic (Physical property) |
|---|---|---|---|---|---|---|
| 1100 | 5-Ph | 0 | Cl | OMe | SO$_2$Me | |
| 1101 | 5-Ph | 0 | Cl | OEt | Br | |
| 1102 | 5-Ph | 0 | Br | H | OMe | |
| 1103 | 5-Ph | 0 | F | H | F | |
| 1104 | 5-Ph | 0 | I | I | I | |
| 1105 | 5-Ph | 0 | Me | H | CN | |
| 1106 | 5-Ph | 0 | Me | H | Me | |
| 1107 | 5-Ph | 0 | Me | H | OMe | |
| 1108 | 5-Ph | 0 | Me | Cl | Cl | |
| 1109 | 5-Ph | 0 | Me | CO$_2$Me | SO$_2$Me | |
| 1110 | 5-Ph | 0 | Me | CH$_2$OMe | SO$_2$Me | |
| 1111 | 5-Ph | 0 | Me | CH(Me)OMe | SO$_2$Me | |
| 1112 | 5-Ph | 0 | NO$_2$ | H | Cl | |
| 1113 | 5-Ph | 0 | NO$_2$ | H | Br | |
| 1114 | 5-Ph | 0 | NO$_2$ | H | F | |
| 1115 | 5-Ph | 0 | NO$_2$ | H | CN | |
| 1116 | 5-Ph | 0 | NO$_2$ | H | SMe | |
| 1117 | 5-Ph | 0 | NO$_2$ | H | CF$_3$ | |
| 1118 | 5-Ph | 0 | NO$_2$ | OMe | Cl | |
| 1119 | 5-Ph | 0 | NO$_2$ | OMe | CF$_3$ | |
| 1120 | 5-Ph | 0 | CF$_3$ | H | Cl | |
| 1121 | 5-Ph | 0 | CF$_3$ | H | Br | |
| 1122 | 5-Ph | 0 | CF$_3$ | H | SMe | |
| 1123 | 5-Ph | 0 | CF$_3$ | H | CF$_3$ | |
| 1124 | 5-Ph | 0 | OMe | H | Cl | |
| 1125 | 5-Ph | 0 | OMe | H | OMe | |
| 1126 | 5-Ph | 1 | Cl | H | Cl | |
| 1127 | 5-Ph | 1 | Cl | H | SO$_2$Me | |
| 1128 | 5-Ph | 1 | Cl | H | NO$_2$ | |
| 1129 | 5-Ph | 1 | Cl | H | OMe | |
| 1130 | 5-Ph | 1 | Cl | H | Me | |
| 1131 | 5-Ph | 1 | Cl | H | Br | |
| 1132 | 5-Ph | 1 | Cl | H | F | |
| 1133 | 5-Ph | 1 | Cl | H | SMe | |
| 1134 | 5-Ph | 1 | Cl | H | S(O)Me | |
| 1135 | 5-Ph | 1 | Cl | H | CF$_3$ | |
| 1136 | 5-Ph | 1 | Cl | H | CN | |
| 1137 | 5-Ph | 1 | Cl | Cl | Cl | |
| 1138 | 5-Ph | 1 | Cl | Cl | OMe | |
| 1139 | 5-Ph | 1 | Cl | Cl | SMe | |
| 1140 | 5-Ph | 1 | Cl | Cl | SO$_2$Me | |
| 1141 | 5-Ph | 1 | Cl | Me | Cl | |
| 1142 | 5-Ph | 1 | Cl | Me | SO$_2$Me | |
| 1143 | 5-Ph | 1 | Cl | OMe | Cl | |
| 1144 | 5-Ph | 1 | Cl | OMe | Br | |
| 1145 | 5-Ph | 1 | Cl | OMe | SO$_2$Me | |
| 1146 | 5-Ph | 1 | Cl | OEt | Br | |
| 1147 | 5-Ph | 1 | Br | H | OMe | |
| 1148 | 5-Ph | 1 | F | H | F | |
| 1149 | 5-Ph | 1 | I | I | I | |
| 1150 | 5-Ph | 1 | Me | H | CN | |
| 1151 | 5-Ph | 1 | Me | H | Me | |
| 1152 | 5-Ph | 1 | Me | H | OMe | |
| 1153 | 5-Ph | 1 | Me | Cl | Cl | |
| 1154 | 5-Ph | 1 | Me | CO$_2$Me | SO$_2$Me | |
| 1155 | 5-Ph | 1 | Me | CH$_2$OMe | SO$_2$Me | |
| 1156 | 5-Ph | 1 | Me | CH(Me)OMe | SO$_2$Me | |
| 1157 | 5-Ph | 1 | NO$_2$ | H | Cl | |
| 1158 | 5-Ph | 1 | NO$_2$ | H | Br | |
| 1159 | 5-Ph | 1 | NO$_2$ | H | F | |
| 1160 | 5-Ph | 1 | NO$_2$ | H | CN | |
| 1161 | 5-Ph | 1 | NO$_2$ | H | SMe | |
| 1162 | 5-Ph | 1 | NO$_2$ | H | CF$_3$ | |
| 1163 | 5-Ph | 1 | NO$_2$ | OMe | Cl | |
| 1164 | 5-Ph | 1 | NO$_2$ | OMe | CF$_3$ | |
| 1165 | 5-Ph | 1 | CF$_3$ | H | Cl | |
| 1166 | 5-Ph | 1 | CF$_3$ | H | Br | |
| 1167 | 5-Ph | 1 | CF$_3$ | H | SMe | |
| 1168 | 5-Ph | 1 | CF$_3$ | H | CF$_3$ | |
| 1169 | 5-Ph | 1 | OMe | H | Cl | |
| 1170 | 5-Ph | 1 | OMe | H | OMe | |

TABLE 1-continued

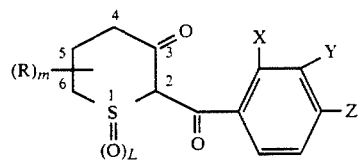

| Compound No. of present invention | (R)$_m$ | L | X | Y | Z | Chracteristic (Physical property) |
|---|---|---|---|---|---|---|
| 1171 | 5-Ph | 2 | Cl | H | Cl | |
| 1172 | 5-Ph | 2 | Cl | H | SO$_2$Me | |
| 1173 | 5-Ph | 2 | Cl | H | NO$_2$ | |
| 1174 | 5-Ph | 2 | Cl | H | OMe | |
| 1175 | 5-Ph | 2 | Cl | H | Me | |
| 1176 | 5-Ph | 2 | Cl | H | Br | |
| 1177 | 5-Ph | 2 | Cl | H | F | |
| 1178 | 5-Ph | 2 | Cl | H | SMe | |
| 1179 | 5-Ph | 2 | Cl | H | S(O)Me | |
| 1180 | 5-Ph | 2 | Cl | H | CF$_3$ | |
| 1181 | 5-Ph | 2 | Cl | H | CN | |
| 1182 | 5-Ph | 2 | Cl | Cl | Cl | |
| 1183 | 5-Ph | 2 | Cl | Cl | OMe | |
| 1184 | 5-Ph | 2 | Cl | Cl | SMe | |
| 1185 | 5-Ph | 2 | Cl | Cl | SO$_2$Me | |
| 1186 | 5-Ph | 2 | Cl | Me | Cl | |
| 1187 | 5-Ph | 2 | Cl | Me | SO$_2$Me | |
| 1188 | 5-Ph | 2 | Cl | OMe | Cl | |
| 1189 | 5-Ph | 2 | Cl | OMe | Br | |
| 1190 | 5-Ph | 2 | Cl | OMe | SO$_2$Me | |
| 1191 | 5-Ph | 2 | Cl | OEt | Br | |
| 1192 | 5-Ph | 2 | Br | H | OMe | |
| 1193 | 5-Ph | 2 | F | H | F | |
| 1194 | 5-Ph | 2 | I | I | I | |
| 1195 | 5-Ph | 2 | Me | H | CN | |
| 1196 | 5-Ph | 2 | Me | H | Me | |
| 1197 | 5-Ph | 2 | Me | H | OMe | |
| 1198 | 5-Ph | 2 | Me | Cl | Cl | |
| 1199 | 5-Ph | 2 | Me | CO$_2$Me | SO$_2$Me | |
| 1200 | 5-Ph | 2 | Me | CH$_2$OMe | SO$_2$Me | |
| 1201 | 5-Ph | 2 | Me | CH(Me)OMe | SO$_2$Me | |
| 1202 | 5-Ph | 2 | NO$_2$ | H | Cl | |
| 1203 | 5-Ph | 2 | NO$_2$ | H | Br | |
| 1204 | 5-Ph | 2 | NO$_2$ | H | F | |
| 1205 | 5-Ph | 2 | NO$_2$ | H | CN | |
| 1206 | 5-Ph | 2 | NO$_2$ | H | SMe | |
| 1207 | 5-Ph | 2 | NO$_2$ | H | CF$_3$ | |
| 1208 | 5-Ph | 2 | NO$_2$ | OMe | Cl | |
| 1209 | 5-Ph | 2 | NO$_2$ | OMe | CF$_3$ | |
| 1210 | 5-Ph | 2 | CF$_3$ | H | Cl | |
| 1211 | 5-Ph | 2 | CF$_3$ | H | Br | |
| 1212 | 5-Ph | 2 | CF$_3$ | H | SMe | |
| 1213 | 5-Ph | 2 | CF$_3$ | H | CF$_3$ | |
| 1214 | 5-Ph | 2 | OMe | H | Cl | |
| 1215 | 5-Ph | 2 | OMe | H | OMe | |
| 1216 | 6-Ph | 0 | Cl | H | Cl | |
| 1217 | 6-Ph | 0 | Cl | H | SO$_2$Me | |
| 1218 | 6-Ph | 0 | Cl | H | NO$_2$ | |
| 1219 | 6-Ph | 0 | Cl | H | OMe | |
| 1220 | 6-Ph | 0 | Cl | H | Me | |
| 1221 | 6-Ph | 0 | Cl | H | Br | |
| 1222 | 6-Ph | 0 | Cl | H | F | |
| 1223 | 6-Ph | 0 | Cl | H | SMe | |
| 1224 | 6-Ph | 0 | Cl | H | S(O)Me | |
| 1225 | 6-Ph | 0 | Cl | H | CF$_3$ | |
| 1226 | 6-Ph | 0 | Cl | H | CN | |
| 1227 | 6-Ph | 0 | Cl | Cl | Cl | |
| 1228 | 6-Ph | 0 | Cl | Cl | OMe | |
| 1229 | 6-Ph | 0 | Cl | Cl | SMe | |
| 1230 | 6-Ph | 0 | Cl | Cl | SO$_2$Me | |
| 1231 | 6-Ph | 0 | Cl | Me | Cl | |
| 1232 | 6-Ph | 0 | Cl | Me | SO$_2$Me | |
| 1233 | 6-Ph | 0 | Cl | OMe | Cl | |
| 1234 | 6-Ph | 0 | Cl | OMe | Br | |
| 1235 | 6-Ph | 0 | Cl | OMe | SO$_2$Me | |
| 1236 | 6-Ph | 0 | Cl | OEt | Br | |
| 1237 | 6-Ph | 0 | Br | H | OMe | |
| 1238 | 6-Ph | 0 | F | H | F | |
| 1239 | 6-Ph | 0 | I | I | I | |
| 1240 | 6-Ph | 0 | Me | H | CN | |
| 1241 | 6-Ph | 0 | Me | H | Me | |

TABLE 1-continued

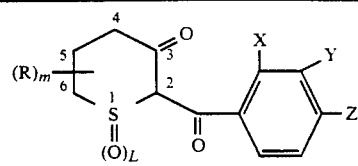

| Compound No. of present invention | (R)$_m$ | L | X | Y | Z | Chracteristic (Physical property) |
|---|---|---|---|---|---|---|
| 1242 | 6-Ph | 0 | Me | H | OMe | |
| 1243 | 6-Ph | 0 | Me | Cl | Cl | |
| 1244 | 6-Ph | 0 | Me | CO$_2$Me | SO$_2$Me | |
| 1245 | 6-Ph | 0 | Me | CH$_2$OMe | SO$_2$Me | |
| 1246 | 6-Ph | 0 | Me | CH(Me)OMe | SO$_2$Me | |
| 1247 | 6-Ph | 0 | NO$_2$ | H | Cl | |
| 1248 | 6-Ph | 0 | NO$_2$ | H | Br | |
| 1249 | 6-Ph | 0 | NO$_2$ | H | F | |
| 1250 | 6-Ph | 0 | NO$_2$ | H | CN | |
| 1251 | 6-Ph | 0 | NO$_2$ | H | SMe | |
| 1252 | 6-Ph | 0 | NO$_2$ | H | CF$_3$ | |
| 1253 | 6-Ph | 0 | NO$_2$ | OMe | Cl | |
| 1254 | 6-Ph | 0 | NO$_2$ | OMe | CF$_3$ | |
| 1255 | 6-Ph | 0 | CF$_3$ | H | Cl | |
| 1256 | 6-Ph | 0 | CF$_3$ | H | Br | |
| 1257 | 6-Ph | 0 | CF$_3$ | H | SMe | |
| 1258 | 6-Ph | 0 | CF$_3$ | H | CF$_3$ | |
| 1259 | 6-Ph | 0 | OMe | H | Cl | |
| 1260 | 6-Ph | 0 | OMe | H | OMe | |
| 1261 | 6-Ph | 1 | Cl | H | Cl | |
| 1262 | 6-Ph | 1 | Cl | H | SO$_2$Me | |
| 1263 | 6-Ph | 1 | Cl | H | NO$_2$ | |
| 1264 | 6-Ph | 1 | Cl | H | OMe | |
| 1265 | 6-Ph | 1 | Cl | H | Me | |
| 1266 | 6-Ph | 1 | Cl | H | Br | |
| 1267 | 6-Ph | 1 | Cl | H | F | |
| 1268 | 6-Ph | 1 | Cl | H | SMe | |
| 1269 | 6-Ph | 1 | Cl | H | S(O)Me | |
| 1270 | 6-Ph | 1 | Cl | H | CF$_3$ | |
| 1271 | 6-Ph | 1 | Cl | H | CN | |
| 1272 | 6-Ph | 1 | Cl | Cl | Cl | |
| 1273 | 6-Ph | 1 | Cl | Cl | OMe | |
| 1274 | 6-Ph | 1 | Cl | Cl | SMe | |
| 1275 | 6-Ph | 1 | Cl | Cl | SO$_2$Me | |
| 1276 | 6-Ph | 1 | Cl | Me | Cl | |
| 1277 | 6-Ph | 1 | Cl | Me | SO$_2$Me | |
| 1278 | 6-Ph | 1 | Cl | OMe | Cl | |
| 1279 | 6-Ph | 1 | Cl | OMe | Br | |
| 1280 | 6-Ph | 1 | Cl | OMe | SO$_2$Me | |
| 1281 | 6-Ph | 1 | Cl | OEt | Br | |
| 1282 | 6-Ph | 1 | Br | H | OMe | |
| 1283 | 6-Ph | 1 | F | H | F | |
| 1284 | 6-Ph | 1 | I | I | I | |
| 1285 | 6-Ph | 1 | Me | H | CN | |
| 1286 | 6-Ph | 1 | Me | H | Me | |
| 1287 | 6-Ph | 1 | Me | H | OMe | |
| 1288 | 6-Ph | 1 | Me | Cl | Cl | |
| 1289 | 6-Ph | 1 | Me | CO$_2$Me | SO$_2$Me | |
| 1290 | 6-Ph | 1 | Me | CH$_2$OMe | SO$_2$Me | |
| 1291 | 6-Ph | 1 | Me | CH(Me)OMe | SO$_2$Me | |
| 1292 | 6-Ph | 1 | NO$_2$ | H | Cl | |
| 1293 | 6-Ph | 1 | NO$_2$ | H | Br | |
| 1294 | 6-Ph | 1 | NO$_2$ | H | F | |
| 1295 | 6-Ph | 1 | NO$_2$ | H | CN | |
| 1296 | 6-Ph | 1 | NO$_2$ | H | SMe | |
| 1297 | 6-Ph | 1 | NO$_2$ | H | CF$_3$ | |
| 1298 | 6-Ph | 1 | NO$_2$ | OMe | Cl | |
| 1299 | 6-Ph | 1 | NO$_2$ | OMe | CF$_3$ | |
| 1300 | 6-Ph | 1 | CF$_3$ | H | Cl | |
| 1301 | 6-Ph | 1 | CF$_3$ | H | Br | |
| 1302 | 6-Ph | 1 | CF$_3$ | H | SMe | |
| 1303 | 6-Ph | 1 | CF$_3$ | H | CF$_3$ | |
| 1304 | 6-Ph | 1 | OMe | H | Cl | |
| 1305 | 6-Ph | 1 | OMe | H | OMe | |
| 1306 | 6-Ph | 2 | Cl | H | Cl | |
| 1307 | 6-Ph | 2 | Cl | H | SO$_2$Me | |
| 1308 | 6-Ph | 2 | Cl | H | NO$_2$ | |
| 1309 | 6-Ph | 2 | Cl | H | OMe | |
| 1310 | 6-Ph | 2 | Cl | H | Me | |
| 1311 | 6-Ph | 2 | Cl | H | Br | |
| 1312 | 6-Ph | 2 | Cl | H | F | |

TABLE 1-continued

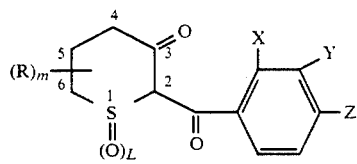

| Compound No. of present invention | (R)$_m$ | L | X | Y | Z | Chracteristic (Physical property) |
|---|---|---|---|---|---|---|
| 1313 | 6-Ph | 2 | Cl | H | SMe | |
| 1314 | 6-Ph | 2 | Cl | H | S(O)Me | |
| 1315 | 6-Ph | 2 | Cl | H | CF$_3$ | |
| 1316 | 6-Ph | 2 | Cl | H | CN | |
| 1317 | 6-Ph | 2 | Cl | Cl | Cl | |
| 1318 | 6-Ph | 2 | Cl | Cl | OMe | |
| 1319 | 6-Ph | 2 | Cl | Cl | SMe | |
| 1320 | 6-Ph | 2 | Cl | Cl | SO$_2$Me | |
| 1321 | 6-Ph | 2 | Cl | Me | Cl | |
| 1322 | 6-Ph | 2 | Cl | Me | SO$_2$Me | |
| 1323 | 6-Ph | 2 | Cl | OMe | Cl | |
| 1324 | 6-Ph | 2 | Cl | OMe | Br | |
| 1325 | 6-Ph | 2 | Cl | OMe | SO$_2$Me | |
| 1326 | 6-Ph | 2 | Cl | OEt | Br | |
| 1327 | 6-Ph | 2 | Br | H | OMe | |
| 1328 | 6-Ph | 2 | F | H | F | |
| 1329 | 6-Ph | 2 | I | I | I | |
| 1330 | 6-Ph | 2 | Me | H | CN | |
| 1331 | 6-Ph | 2 | Me | H | Me | |
| 1332 | 6-Ph | 2 | Me | H | OMe | |
| 1333 | 6-Ph | 2 | Me | Cl | Cl | |
| 1334 | 6-Ph | 2 | Me | CO$_2$Me | SO$_2$Me | |
| 1335 | 6-Ph | 2 | Me | CH$_2$OMe | SO$_2$Me | |
| 1336 | 6-Ph | 2 | Me | CH(Me)OMe | SO$_2$Me | |
| 1337 | 6-Ph | 2 | NO$_2$ | H | Cl | |
| 1338 | 6-Ph | 2 | NO$_2$ | H | Br | |
| 1339 | 6-Ph | 2 | NO$_2$ | H | F | |
| 1340 | 6-Ph | 2 | NO$_2$ | H | CN | |
| 1341 | 6-Ph | 2 | NO$_2$ | H | SMe | |
| 1342 | 6-Ph | 2 | NO$_2$ | H | CF$_3$ | |
| 1343 | 6-Ph | 2 | NO$_2$ | OMe | Cl | |
| 1344 | 6-Ph | 2 | NO$_2$ | OMe | CF$_3$ | |
| 1345 | 6-Ph | 2 | CF$_3$ | H | Cl | |
| 1346 | 6-Ph | 2 | CF$_3$ | H | Br | |
| 1347 | 6-Ph | 2 | CF$_3$ | H | SMe | |
| 1348 | 6-Ph | 2 | CF$_3$ | H | CF$_3$ | |
| 1349 | 6-Ph | 2 | OMe | H | Cl | |
| 1350 | 6-Ph | 2 | OMe | H | OMe | |
| 1351 | 5-(4-Cl—Ph) | 0 | Cl | H | Cl | |
| 1352 | 5-(4-Cl—Ph) | 0 | Cl | H | SO$_2$Me | |
| 1353 | 5-(4-Cl—Ph) | 0 | Cl | H | NO$_2$ | |
| 1354 | 5-(4-Cl—Ph) | 0 | Cl | H | OMe | |
| 1355 | 5-(4-Cl—Ph) | 0 | Cl | H | Me | |
| 1356 | 5-(4-Cl—Ph) | 0 | Cl | H | Br | |
| 1357 | 5-(4-Cl—Ph) | 0 | Cl | H | F | |
| 1358 | 5-(4-Cl—Ph) | 0 | Cl | H | SMe | |
| 1359 | 5-(4-Cl—Ph) | 0 | Cl | H | S(O)Me | |
| 1360 | 5-(4-Cl—Ph) | 0 | Cl | H | CF$_3$ | |
| 1361 | 5-(4-Cl—Ph) | 0 | Cl | H | CN | |
| 1362 | 5-(4-Cl—Ph) | 0 | Cl | Cl | Cl | |
| 1363 | 5-(4-Cl—Ph) | 0 | Cl | Cl | OMe | |
| 1364 | 5-(4-Cl—Ph) | 0 | Cl | Cl | SMe | |
| 1365 | 5-(4-Cl—Ph) | 0 | Cl | Cl | SO$_2$Me | |
| 1366 | 5-(4-Cl—Ph) | 1 | Cl | Me | Cl | |
| 1367 | 5-(4-Cl—Ph) | 1 | Cl | Me | SO$_2$Me | |
| 1368 | 5-(4-Cl—Ph) | 1 | Cl | OMe | Cl | |
| 1369 | 5-(4-Cl—Ph) | 1 | Cl | OMe | Br | |
| 1370 | 5-(4-Cl—Ph) | 0 | Cl | OMe | SO$_2$Me | |
| 1371 | 5-(4-Cl—Ph) | 0 | Cl | OEt | Br | |
| 1372 | 5-(4-Cl—Ph) | 0 | Br | H | OMe | |
| 1373 | 5-(4-Cl—Ph) | 0 | F | H | F | |
| 1374 | 5-(4-Cl—Ph) | 0 | I | I | I | |
| 1375 | 5-(4-Cl—Ph) | 0 | Me | H | CN | |
| 1376 | 5-(4-Cl—Ph) | 0 | Me | H | Me | |
| 1377 | 5-(4-Cl—Ph) | 0 | Me | H | OMe | |
| 1378 | 5-(4-Cl—Ph) | 0 | Me | Cl | Cl | |
| 1379 | 5-(4-Cl—Ph) | 0 | Me | CO$_2$Me | SO$_2$Me | |
| 1380 | 5-(4-Cl—Ph) | 0 | Me | CH$_2$OMe | SO$_2$Me | |
| 1381 | 5-(4-Cl—Ph) | 0 | Me | CH(Me)OMe | SO$_2$Me | |
| 1382 | 5-(4-Cl—Ph) | 0 | NO$_2$ | H | Cl | |
| 1383 | 5-(4-Cl—Ph) | 0 | NO$_2$ | H | Br | |

TABLE 1-continued

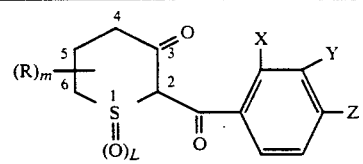

| Compound No. of present invention | (R)$_m$ | L | X | Y | Z | Chracteristic (Physical property) |
|---|---|---|---|---|---|---|
| 1384 | 5-(4-Cl—Ph) | 0 | NO$_2$ | H | F | |
| 1385 | 5-(4-Cl—Ph) | 0 | NO$_2$ | H | CN | |
| 1386 | 5-(4-Cl—Ph) | 0 | NO$_2$ | H | SMe | |
| 1387 | 5-(4-Cl—Ph) | 0 | NO$_2$ | H | CF$_3$ | |
| 1388 | 5-(4-Cl—Ph) | 0 | NO$_2$ | OMe | Cl | |
| 1389 | 5-(4-Cl—Ph) | 0 | NO$_2$ | OMe | CF$_3$ | |
| 1390 | 5-(4-Cl—Ph) | 0 | CF$_3$ | H | Cl | |
| 1391 | 5-(4-Cl—Ph) | 0 | CF$_3$ | H | Br | |
| 1392 | 5-(4-Cl—Ph) | 0 | CF$_3$ | H | SMe | |
| 1393 | 5-(4-Cl—Ph) | 0 | CF$_3$ | H | CF$_3$ | |
| 1394 | 5-(4-Cl—Ph) | 0 | OMe | H | Cl | |
| 1395 | 5-(4-Cl—Ph) | 0 | OMe | H | OMe | |
| 1396 | 5-(4-Cl—Ph) | 1 | Cl | H | Cl | |
| 1397 | 5-(4-Cl—Ph) | 1 | Cl | H | SO$_2$Me | |
| 1398 | 5-(4-Cl—Ph) | 1 | Cl | H | NO$_2$ | |
| 1399 | 5-(4-Cl—Ph) | 1 | Cl | H | OMe | |
| 1400 | 5-(4-Cl—Ph) | 1 | Cl | H | Me | |
| 1401 | 5-(4-Cl—Ph) | 1 | Cl | H | Br | |
| 1402 | 5-(4-Cl—Ph) | 1 | Cl | H | F | |
| 1403 | 5-(4-Cl—Ph) | 1 | Cl | H | SMe | |
| 1404 | 5-(4-Cl—Ph) | 1 | Cl | H | S(O)Me | |
| 1405 | 5-(4-Cl—Ph) | 1 | Cl | H | CF$_3$ | |
| 1406 | 5-(4-Cl—Ph) | 1 | Cl | H | CN | |
| 1407 | 5-(4-Cl—Ph) | 1 | Cl | Cl | Cl | |
| 1408 | 5-(4-Cl—Ph) | 1 | Cl | Cl | OMe | |
| 1409 | 5-(4-Cl—Ph) | 1 | Cl | Cl | SMe | |
| 1410 | 5-(4-Cl—Ph) | 1 | Cl | Cl | SO$_2$Me | |
| 1411 | 5-(4-Cl—Ph) | 1 | Cl | Me | Cl | |
| 1412 | 5-(4-Cl—Ph) | 1 | Cl | Me | SO$_2$Me | |
| 1413 | 5-(4-Cl—Ph) | 1 | Cl | OMe | Cl | |
| 1414 | 5-(4-Cl—Ph) | 1 | Cl | OMe | Br | |
| 1415 | 5-(4-Cl—Ph) | 1 | Cl | OMe | SO$_2$Me | |
| 1416 | 5-(4-Cl—Ph) | 1 | Cl | OEt | Br | |
| 1417 | 5-(4-Cl—Ph) | 1 | Br | H | OMe | |
| 1418 | 5-(4-Cl—Ph) | 1 | F | H | F | |
| 1419 | 5-(4-Cl—Ph) | 1 | I | I | I | |
| 1420 | 5-(4-Cl—Ph) | 1 | Me | H | CN | |
| 1421 | 5-(4-Cl—Ph) | 1 | Me | H | Me | |
| 1422 | 5-(4-Cl—Ph) | 1 | Me | H | OMe | |
| 1423 | 5-(4-Cl—Ph) | 1 | Me | Cl | Cl | |
| 1424 | 5-(4-Cl—Ph) | 1 | Me | CO$_2$Me | SO$_2$Me | |
| 1425 | 5-(4-Cl—Ph) | 1 | Me | CH$_2$OMe | SO$_2$Me | |
| 1426 | 5-(4-Cl—Ph) | 1 | Me | CH(Me)OMe | SO$_2$Me | |
| 1427 | 5-(4-Cl—Ph) | 1 | NO$_2$ | H | Cl | |
| 1428 | 5-(4-Cl—Ph) | 1 | NO$_2$ | H | Br | |
| 1429 | 5-(4-Cl—Ph) | 1 | NO$_2$ | H | F | |
| 1430 | 5-(4-Cl—Ph) | 1 | NO$_2$ | H | CN | |
| 1431 | 5-(4-Cl—Ph) | 1 | NO$_2$ | H | SMe | |
| 1432 | 5-(4-Cl—Ph) | 1 | NO$_2$ | H | CF$_3$ | |
| 1433 | 5-(4-Cl—Ph) | 1 | NO$_2$ | OMe | Cl | |
| 1434 | 5-(4-Cl—Ph) | 1 | NO$_2$ | OMe | CF$_3$ | |
| 1435 | 5-(4-Cl—Ph) | 1 | CF$_3$ | H | Cl | |
| 1436 | 5-(4-Cl—Ph) | 1 | CF$_3$ | H | Br | |
| 1437 | 5-(4-Cl—Ph) | 1 | CF$_3$ | H | SMe | |
| 1438 | 5-(4-Cl—Ph) | 1 | CF$_3$ | H | CF$_3$ | |
| 1439 | 5-(4-Cl—Ph) | 1 | OMe | H | Cl | |
| 1440 | 5-(4-Cl—Ph) | 1 | OMe | H | OMe | |
| 1441 | 5-(4-Cl—Ph) | 2 | Cl | H | Cl | |
| 1442 | 5-(4-Cl—Ph) | 2 | Cl | H | SO$_2$Me | |
| 1443 | 5-(4-Cl—Ph) | 2 | Cl | H | NO$_2$ | |
| 1444 | 5-(4-Cl—Ph) | 2 | Cl | H | OMe | |
| 1445 | 5-(4-Cl—Ph) | 2 | Cl | H | Me | |
| 1446 | 5-(4-Cl—Ph) | 2 | Cl | H | Br | |
| 1447 | 5-(4-Cl—Ph) | 2 | Cl | H | F | |
| 1448 | 5-(4-Cl—Ph) | 2 | Cl | H | SMe | |
| 1449 | 5-(4-Cl—Ph) | 2 | Cl | H | S(O)Me | |
| 1450 | 5-(4-Cl—Ph) | 2 | Cl | H | CF$_3$ | |
| 1451 | 5-(4-Cl—Ph) | 2 | Cl | H | CN | |
| 1452 | 5-(4-Cl—Ph) | 2 | Cl | Cl | Cl | |
| 1453 | 5-(4-Cl—Ph) | 2 | Cl | Cl | OMe | |
| 1454 | 5-(4-Cl—Ph) | 2 | Cl | Cl | SMe | |

TABLE 1-continued

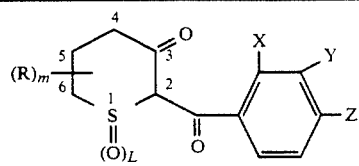

| Compound No. of present invention | (R)$_m$ | L | X | Y | Z | Characteristic (Physical property) |
|---|---|---|---|---|---|---|
| 1455 | 5-(4-Cl—Ph) | 2 | Cl | Cl | SO$_2$Me | |
| 1456 | 5-(4-Cl—Ph) | 2 | Cl | Me | Cl | |
| 1457 | 5-(4-Cl—Ph) | 2 | Cl | Me | SO$_2$Me | |
| 1458 | 5-(4-Cl—Ph) | 2 | Cl | OMe | Cl | |
| 1459 | 5-(4-Cl—Ph) | 2 | Cl | OMe | Br | |
| 1460 | 5-(4-Cl—Ph) | 2 | Cl | OMe | SO$_2$Me | |
| 1461 | 5-(4-Cl—Ph) | 2 | Cl | OEt | Br | |
| 1462 | 5-(4-Cl—Ph) | 2 | Br | H | OMe | |
| 1463 | 5-(4-Cl—Ph) | 2 | F | H | F | |
| 1464 | 5-(4-Cl—Ph) | 2 | I | I | I | |
| 1465 | 5-(4-Cl—Ph) | 2 | Me | H | CN | |
| 1466 | 5-(4-Cl—Ph) | 2 | Me | H | Me | |
| 1467 | 5-(4-Cl—Ph) | 2 | Me | H | OMe | |
| 1468 | 5-(4-Cl—Ph) | 2 | Me | Cl | Cl | |
| 1469 | 5-(4-Cl—Ph) | 2 | Me | CO$_2$Me | SO$_2$Me | |
| 1470 | 5-(4-Cl—Ph) | 2 | Me | CH$_2$OMe | SO$_2$Me | |
| 1471 | 5-(4-Cl—Ph) | 2 | Me | CH(Me)OMe | SO$_2$Me | |
| 1472 | 5-(4-Cl—Ph) | 2 | NO$_2$ | H | Cl | |
| 1473 | 5-(4-Cl—Ph) | 2 | NO$_2$ | H | Br | |
| 1474 | 5-(4-Cl—Ph) | 2 | NO$_2$ | H | F | |
| 1475 | 5-(4-Cl—Ph) | 2 | NO$_2$ | H | CN | |
| 1476 | 5-(4-Cl—Ph) | 2 | NO$_2$ | H | SMe | |
| 1477 | 5-(4-Cl—Ph) | 2 | NO$_2$ | H | CF$_3$ | |
| 1478 | 5-(4-Cl—Ph) | 2 | NO$_2$ | OMe | Cl | |
| 1479 | 5-(4-Cl—Ph) | 2 | NO$_2$ | OMe | CF$_3$ | |
| 1480 | 5-(4-Cl—Ph) | 2 | CF$_3$ | H | Cl | |
| 1481 | 5-(4-Cl—Ph) | 2 | CF$_3$ | H | Br | |
| 1482 | 5-(4-Cl—Ph) | 2 | CF$_3$ | H | SMe | |
| 1483 | 5-(4-Cl—Ph) | 2 | CF$_3$ | H | CF$_3$ | |
| 1484 | 5-(4-Cl—Ph) | 2 | OMe | H | Cl | |
| 1485 | 5-(4-Cl—Ph) | 2 | OMe | H | OMe | |
| 1486 | 5-(4-Me—Ph) | 0 | Cl | H | Cl | |
| 1487 | 5-(4-Me—Ph) | 0 | Cl | H | SO$_2$Me | |
| 1488 | 5-(4-Me—Ph) | 0 | Cl | H | NO$_2$ | |
| 1489 | 5-(4-Me—Ph) | 0 | Cl | H | OMe | |
| 1490 | 5-(4-Me—Ph) | 0 | Cl | H | Me | |
| 1491 | 5-(4-Me—Ph) | 0 | Cl | H | Br | |
| 1492 | 5-(4-Me—Ph) | 0 | Cl | H | F | |
| 1493 | 5-(4-Me—Ph) | 0 | Cl | H | SMe | |
| 1494 | 5-(4-Me—Ph) | 0 | Cl | H | S(O)Me | |
| 1495 | 5-(4-Me—Ph) | 0 | Cl | H | CF$_3$ | |
| 1496 | 5-(4-Me—Ph) | 0 | Cl | H | CN | |
| 1497 | 5-(4-Me—Ph) | 0 | Cl | Cl | Cl | |
| 1498 | 5-(4-Me—Ph) | 0 | Cl | Cl | OMe | |
| 1499 | 5-(4-Me—Ph) | 0 | Cl | Cl | SMe | |
| 1500 | 5-(4-Me—Ph) | 0 | Cl | Cl | SO$_2$Me | |
| 1501 | 5-(4-Me—Ph) | 0 | Cl | Me | Cl | |
| 1502 | 5-(4-Me—Ph) | 0 | Cl | Me | SO$_2$Me | |
| 1503 | 5-(4-Me—Ph) | 0 | Cl | OMe | Cl | |
| 1504 | 5-(4-Me—Ph) | 0 | Cl | OMe | Br | |
| 1505 | 5-(4-Me—Ph) | 0 | Cl | OMe | SO$_2$Me | |
| 1506 | 5-(4-Me—Ph) | 0 | Cl | OEt | Br | |
| 1507 | 5-(4-Me—Ph) | 0 | Br | H | OMe | |
| 1508 | 5-(4-Me—Ph) | 0 | F | H | F | |
| 1509 | 5-(4-Me—Ph) | 0 | I | I | I | |
| 1510 | 5-(4-Me—Ph) | 0 | Me | H | CN | |
| 1511 | 5-(4-Me—Ph) | 0 | Me | H | Me | |
| 1512 | 5-(4-Me—Ph) | 0 | Me | H | OMe | |
| 1513 | 5-(4-Me—Ph) | 0 | Me | Cl | Cl | |
| 1514 | 5-(4-Me—Ph) | 0 | Me | CO$_2$Me | SO$_2$Me | |
| 1515 | 5-(4-Me—Ph) | 0 | Me | CH$_2$OMe | SO$_2$Me | |
| 1516 | 5-(4-Me—Ph) | 0 | Me | CH(Me)OMe | SO$_2$Me | |
| 1517 | 5-(4-Me—Ph) | 0 | NO$_2$ | H | Cl | |
| 1518 | 5-(4-Me—Ph) | 0 | NO$_2$ | H | Br | |
| 1519 | 5-(4-Me—Ph) | 0 | NO$_2$ | H | F | |
| 1520 | 5-(4-Me—Ph) | 0 | NO$_2$ | H | CN | |
| 1521 | 5-(4-Me—Ph) | 0 | NO$_2$ | H | SMe | |
| 1522 | 5-(4-Me—Ph) | 0 | NO$_2$ | H | CF$_3$ | |
| 1523 | 5-(4-Me—Ph) | 0 | NO$_2$ | OMe | Cl | |
| 1524 | 5-(4-Me—Ph) | 0 | NO$_2$ | OMe | CF$_3$ | |
| 1525 | 5-(4-Me—Ph) | 0 | CF$_3$ | H | Cl | |

TABLE 1-continued

| Compound No. of present invention | (R)$_m$ | L | X | Y | Z | Chracteristic (Physical property) |
|---|---|---|---|---|---|---|
| 1526 | 5-(4-Me—Ph) | 0 | CF$_3$ | H | Br | |
| 1527 | 5-(4-Me—Ph) | 0 | CF$_3$ | H | SMe | |
| 1528 | 5-(4-Me—Ph) | 0 | CF$_3$ | H | CF$_3$ | |
| 1529 | 5-(4-Me—Ph) | 0 | OMe | H | Cl | |
| 1530 | 5-(4-Me—Ph) | 0 | OMe | H | OMe | |
| 1531 | 5-(4-Me—Ph) | 1 | Cl | H | Cl | |
| 1532 | 5-(4-Me—Ph) | 1 | Cl | H | SO$_2$Me | |
| 1533 | 5-(4-Me—Ph) | 1 | Cl | H | NO$_2$ | |
| 1534 | 5-(4-Me—Ph) | 1 | Cl | H | OMe | |
| 1535 | 5-(4-Me—Ph) | 1 | Cl | H | Me | |
| 1536 | 5-(4-Me—Ph) | 1 | Cl | H | Br | |
| 1537 | 5-(4-Me—Ph) | 1 | Cl | H | F | |
| 1538 | 5-(4-Me—Ph) | 1 | Cl | H | SMe | |
| 1539 | 5-(4-Me—Ph) | 1 | Cl | H | S(O)Me | |
| 1540 | 5-(4-Me—Ph) | 1 | Cl | H | CF$_3$ | |
| 1541 | 5-(4-Me—Ph) | 1 | Cl | H | CN | |
| 1542 | 5-(4-Me—Ph) | 1 | Cl | Cl | Cl | |
| 1543 | 5-(4-Me—Ph) | 1 | Cl | Cl | OMe | |
| 1544 | 5-(4-Me—Ph) | 1 | Cl | Cl | SMe | |
| 1545 | 5-(4-Me—Ph) | 1 | Cl | Cl | SO$_2$Me | |
| 1546 | 5-(4-Me—Ph) | 1 | Cl | Me | Cl | |
| 1547 | 5-(4-Me—Ph) | 1 | Cl | Me | SO$_2$Me | |
| 1548 | 5-(4-Me—Ph) | 1 | Cl | OMe | Cl | |
| 1549 | 5-(4-Me—Ph) | 1 | Cl | OMe | Br | |
| 1550 | 5-(4-Me—Ph) | 1 | Cl | OMe | SO$_2$Me | |
| 1551 | 5-(4-Me—Ph) | 1 | Cl | OEt | Br | |
| 1552 | 5-(4-Me—Ph) | 1 | Br | H | OMe | |
| 1553 | 5-(4-Me—Ph) | 1 | F | H | F | |
| 1554 | 5-(4-Me—Ph) | 1 | I | I | I | |
| 1555 | 5-(4-Me—Ph) | 1 | Me | H | CN | |
| 1556 | 5-(4-Me—Ph) | 1 | Me | H | Me | |
| 1557 | 5-(4-Me—Ph) | 1 | Me | H | OMe | |
| 1558 | 5-(4-Me—Ph) | 1 | Me | Cl | Cl | |
| 1559 | 5-(4-Me—Ph) | 1 | Me | CO$_2$Me | SO$_2$Me | |
| 1560 | 5-(4-Me—Ph) | 1 | Me | CH$_2$OMe | SO$_2$Me | |
| 1561 | 5-(4-Me—Ph) | 1 | Me | CH(Me)OMe | SO$_2$Me | |
| 1562 | 5-(4-Me—Ph) | 1 | NO$_2$ | H | Cl | |
| 1563 | 5-(4-Me—Ph) | 1 | NO$_2$ | H | Br | |
| 1564 | 5-(4-Me—Ph) | 1 | NO$_2$ | H | F | |
| 1565 | 5-(4-Me—Ph) | 1 | NO$_2$ | H | CN | |
| 1566 | 5-(4-Me—Ph) | 1 | NO$_2$ | H | SMe | |
| 1567 | 5-(4-Me—Ph) | 1 | NO$_2$ | H | CF$_3$ | |
| 1568 | 5-(4-Me—Ph) | 1 | NO$_2$ | OMe | Cl | |
| 1569 | 5-(4-Me—Ph) | 1 | NO$_2$ | OMe | CF$_3$ | |
| 1570 | 5-(4-Me—Ph) | 1 | CF$_3$ | H | Cl | |
| 1571 | 5-(4-Me—Ph) | 1 | CF$_3$ | H | Br | |
| 1572 | 5-(4-Me—Ph) | 1 | CF$_3$ | H | SMe | |
| 1573 | 5-(4-Me—Ph) | 1 | CF$_3$ | H | CF$_3$ | |
| 1574 | 5-(4-Me—Ph) | 1 | OMe | H | Cl | |
| 1575 | 5-(4-Me—Ph) | 1 | OMe | H | OMe | |
| 1576 | 5-(4-Me—Ph) | 2 | Cl | H | Cl | |
| 1577 | 5-(4-Me—Ph) | 2 | Cl | H | SO$_2$Me | |
| 1578 | 5-(4-Me—Ph) | 2 | Cl | H | NO$_2$ | |
| 1579 | 5-(4-Me—Ph) | 2 | Cl | H | OMe | |
| 1580 | 5-(4-Me—Ph) | 2 | Cl | H | Me | |
| 1581 | 5-(4-Me—Ph) | 2 | Cl | H | Br | |
| 1582 | 5-(4-Me—Ph) | 2 | Cl | H | F | |
| 1583 | 5-(4-Me—Ph) | 2 | Cl | H | SMe | |
| 1584 | 5-(4-Me—Ph) | 2 | Cl | H | S(O)Me | |
| 1585 | 5-(4-Me—Ph) | 2 | Cl | H | CF$_3$ | |
| 1586 | 5-(4-Me—Ph) | 2 | Cl | H | CN | |
| 1587 | 5-(4-Me—Ph) | 2 | Cl | Cl | Cl | |
| 1588 | 5-(4-Me—Ph) | 2 | Cl | Cl | OMe | |
| 1589 | 5-(4-Me—Ph) | 2 | Cl | Cl | SMe | |
| 1590 | 5-(4-Me—Ph) | 2 | Cl | Cl | SO$_2$Me | |
| 1591 | 5-(4-Me—Ph) | 2 | Cl | Me | Cl | |
| 1592 | 5-(4-Me—Ph) | 2 | Cl | Me | SO$_2$Me | |
| 1593 | 5-(4-Me—Ph) | 2 | Cl | OMe | Cl | |
| 1594 | 5-(4-Me—Ph) | 2 | Cl | OMe | Br | |
| 1595 | 5-(4-Me—Ph) | 2 | Cl | OMe | SO$_2$Me | |
| 1596 | 5-(4-Me—Ph) | 2 | Cl | OEt | Br | |

TABLE 1-continued

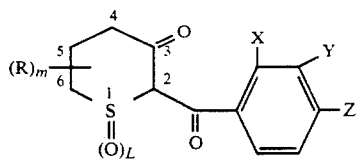

| Compound No. of present invention | (R)$_m$ | L | X | Y | Z | Charicteristic (Physical property) |
|---|---|---|---|---|---|---|
| 1597 | 5-(4-Me—Ph) | 2 | Br | H | OMe | |
| 1598 | 5-(4-Me—Ph) | 2 | F | H | F | |
| 1599 | 5-(4-Me—Ph) | 2 | I | I | I | |
| 1600 | 5-(4-Me—Ph) | 2 | Me | H | CN | |
| 1601 | 5-(4-Me—Ph) | 2 | Me | H | Me | |
| 1602 | 5-(4-Me—Ph) | 2 | Me | H | OMe | |
| 1603 | 5-(4-Me—Ph) | 2 | Me | Cl | Cl | |
| 1604 | 5-(4-Me—Ph) | 2 | Me | CO$_2$Me | SO$_2$Me | |
| 1605 | 5-(4-Me—Ph) | 2 | Me | CH$_2$OMe | SO$_2$Me | |
| 1606 | 5-(4-Me—Ph) | 2 | Me | CH(Me)OMe | SO$_2$Me | |
| 1607 | 5-(4-Me—Ph) | 2 | NO$_2$ | H | Cl | |
| 1608 | 5-(4-Me—Ph) | 2 | NO$_2$ | H | Br | |
| 1609 | 5-(4-Me—Ph) | 2 | NO$_2$ | H | F | |
| 1610 | 5-(4-Me—Ph) | 2 | NO$_2$ | H | CN | |
| 1611 | 5-(4-Me—Ph) | 2 | NO$_2$ | H | SMe | |
| 1612 | 5-(4-Me—Ph) | 2 | NO$_2$ | H | CF$_3$ | |
| 1613 | 5-(4-Me—Ph) | 2 | NO$_2$ | OMe | Cl | |
| 1614 | 5-(4-Me—Ph) | 2 | NO$_2$ | OMe | CF$_3$ | |
| 1615 | 5-(4-Me—Ph) | 2 | CF$_3$ | H | Cl | |
| 1616 | 5-(4-Me—Ph) | 2 | CF$_3$ | H | Br | |
| 1617 | 5-(4-Me—Ph) | 2 | CF$_3$ | H | SMe | |
| 1618 | 5-(4-Me—Ph) | 2 | CF$_3$ | H | CF$_3$ | |
| 1619 | 5-(4-Me—Ph) | 2 | OMe | H | Cl | |
| 1620 | 5-(4-Me—Ph) | 2 | OMe | H | OMe | |

TABLE 2

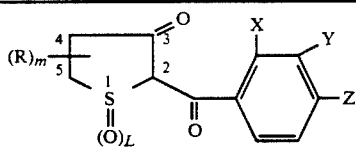

| Compound No. of the present invention | (R)$_m$ | L | X | Y | Z | Chracteristic (Physical property) |
|---|---|---|---|---|---|---|
| 1621 | — | 0 | Cl | H | Cl | |
| 1622 | — | 0 | Cl | H | SO$_2$Me | |
| 1623 | — | 0 | Cl | H | NO$_2$ | |
| 1624 | — | 0 | Cl | H | OMe | |
| 1625 | — | 0 | Cl | H | Me | |
| 1626 | — | 0 | Cl | H | Br | |
| 1627 | — | 0 | Cl | H | F | |
| 1628 | — | 0 | Cl | H | SMe | |
| 1629 | — | 0 | Cl | H | S(O)Me | |
| 1630 | — | 0 | Cl | H | CF$_3$ | |
| 1631 | — | 0 | Cl | H | CN | |
| 1632 | — | 0 | Cl | Cl | Cl | |
| 1633 | — | 0 | Cl | Cl | OMe | |
| 1634 | — | 0 | Cl | Cl | SMe | |
| 1635 | — | 0 | Cl | Cl | SO$_2$Me | |
| 1636 | — | 0 | Cl | Me | Cl | |
| 1637 | — | 0 | Cl | Me | SO$_2$Me | |
| 1638 | — | 0 | Cl | OMe | Cl | |
| 1639 | — | 0 | Cl | OMe | Br | |
| 1640 | — | 0 | Cl | OMe | SO$_2$Me | |
| 1641 | — | 0 | Cl | OEt | Br | |
| 1642 | — | 0 | Br | H | OMe | |
| 1643 | — | 0 | F | H | F | |
| 1644 | — | 0 | I | I | I | |
| 1645 | — | 0 | Me | H | CN | |
| 1626 | — | 0 | Me | H | Me | |
| 1627 | — | 0 | Me | H | OMe | |
| 1628 | — | 0 | Me | Cl | Cl | |
| 1629 | — | 0 | Me | CO$_2$Me | SO$_2$Me | |
| 1630 | — | 0 | Me | CH$_2$OMe | SO$_2$Me | |
| 1631 | — | 0 | Me | CH(Me)OMe | SO$_2$Me | |
| 1632 | — | 0 | NO$_2$ | H | Cl | |
| 1633 | — | 0 | NO$_2$ | H | Br | |

TABLE 2-continued

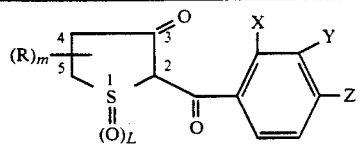

| Compound No. of the present invention | (R)$_m$ | L | X | Y | Z | Characteristic (Physical property) |
|---|---|---|---|---|---|---|
| 1634 | — | 0 | NO$_2$ | H | F | |
| 1635 | — | 0 | NO$_2$ | H | CN | |
| 1636 | — | 0 | NO$_2$ | H | SMe | |
| 1637 | — | 0 | NO$_2$ | H | CF$_3$ | |
| 1638 | — | 0 | NO$_2$ | OMe | Cl | |
| 1639 | — | 0 | NO$_2$ | OMe | CF$_3$ | |
| 1640 | — | 0 | CF$_3$ | H | Cl | |
| 1641 | — | 0 | CF$_3$ | H | Br | |
| 1642 | — | 0 | CF$_3$ | H | SMe | |
| 1643 | — | 0 | CF$_3$ | H | CF$_3$ | |
| 1644 | — | 0 | OMe | H | Cl | |
| 1645 | — | 0 | OMe | H | OMe | |
| 1646 | — | 1 | Cl | H | Cl | |
| 1647 | — | 1 | Cl | H | SO$_2$Me | |
| 1648 | — | 1 | Cl | H | NO$_2$ | |
| 1649 | — | 1 | Cl | H | OMe | |
| 1650 | — | 1 | Cl | H | Me | |
| 1651 | — | 1 | Cl | H | Br | |
| 1652 | — | 1 | Cl | H | F | |
| 1653 | — | 1 | Cl | H | SMe | |
| 1654 | — | 1 | Cl | H | S(O)Me | |
| 1655 | — | 1 | Cl | H | CF$_3$ | |
| 1656 | — | 1 | Cl | H | CN | |
| 1657 | — | 1 | Cl | Cl | Cl | |
| 1658 | — | 1 | Cl | Cl | OMe | |
| 1659 | — | 1 | Cl | Cl | SMe | |
| 1660 | — | 1 | Cl | Cl | SO$_2$Me | |
| 1661 | — | 1 | Cl | Me | Cl | |
| 1662 | — | 1 | Cl | Me | SO$_2$Me | |
| 1663 | — | 1 | Cl | OMe | Cl | |
| 1664 | — | 1 | Cl | OMe | Br | |
| 1665 | — | 1 | Cl | OMe | SO$_2$Me | |
| 1666 | — | 1 | Cl | Oet | Br | |
| 1667 | — | 1 | Br | H | OMe | |
| 1668 | — | 1 | F | H | F | |
| 1669 | — | 1 | I | I | I | |
| 1670 | — | 1 | Me | H | CN | |
| 1671 | — | 1 | Me | H | Me | |
| 1672 | — | 1 | Me | H | OMe | |
| 1673 | — | 1 | Me | Cl | Cl | |
| 1674 | — | 1 | Me | CO$_2$Me | SO$_2$Me | |
| 1675 | — | 1 | Me | CH$_2$OMe | SO$_2$Me | |
| 1676 | — | 1 | Me | CH(Me)OMe | SO$_2$Me | |
| 1677 | — | 1 | NO$_2$ | H | Cl | |
| 1678 | — | 1 | NO$_2$ | H | Br | |
| 1679 | — | 1 | NO$_2$ | H | F | |
| 1680 | — | 1 | NO$_2$ | H | CN | |
| 1681 | — | 1 | NO$_2$ | H | SMe | |
| 1682 | — | 1 | NO$_2$ | H | CF$_3$ | |
| 1683 | — | 1 | NO$_2$ | OMe | Cl | |
| 1684 | — | 1 | NO$_2$ | OMe | CF$_3$ | |
| 1685 | — | 1 | CF$_3$ | H | Cl | |
| 1686 | — | 1 | CF$_3$ | H | Br | |
| 1687 | — | 1 | CF$_3$ | H | SMe | |
| 1688 | — | 1 | CF$_3$ | H | CF$_3$ | |
| 1689 | — | 1 | OMe | H | Cl | |
| 1690 | — | 1 | OMe | H | OMe | |
| 1691 | — | 2 | Cl | H | Cl | |
| 1692 | — | 2 | Cl | H | SO$_2$Me | |
| 1693 | — | 2 | Cl | H | NO$_2$ | |
| 1694 | — | 2 | Cl | H | OMe | |
| 1695 | — | 2 | Cl | H | Me | |
| 1696 | — | 2 | Cl | H | Br | |
| 1697 | — | 2 | Cl | H | F | |
| 1698 | — | 2 | Cl | H | SMe | |
| 1699 | — | 2 | Cl | H | S(O)Me | |
| 1700 | — | 2 | Cl | H | CF$_3$ | |
| 1701 | — | 2 | Cl | H | CN | |
| 1702 | — | 2 | Cl | Cl | Cl | |
| 1703 | — | 2 | Cl | Cl | OMe | |
| 1704 | — | 2 | Cl | Cl | SMe | |
| 1705 | — | 2 | Cl | Cl | SO$_2$Me | |

TABLE 2-continued

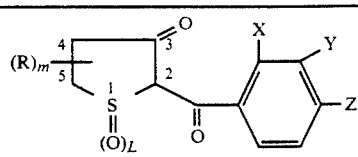

| Compound No. of the present invention | (R)$_m$ | L | X | Y | Z | Characteristic (Physical property) |
|---|---|---|---|---|---|---|
| 1706 | — | 2 | Cl | Me | Cl | |
| 1707 | — | 2 | Cl | Me | SO$_2$Me | |
| 1708 | — | 2 | Cl | OMe | Cl | |
| 1709 | — | 2 | Cl | OMe | Br | |
| 1710 | — | 2 | Cl | OMe | SO$_2$Me | |
| 1711 | — | 2 | Cl | OEt | Br | |
| 1712 | — | 2 | Br | H | OMe | |
| 1713 | — | 2 | F | H | F | |
| 1714 | — | 2 | I | I | I | |
| 1715 | — | 2 | Me | H | CN | |
| 1716 | — | 2 | Me | H | Me | |
| 1717 | — | 2 | Me | H | OMe | |
| 1718 | — | 2 | Me | Cl | Cl | |
| 1719 | — | 2 | Me | CO$_2$Me | SO$_2$Me | |
| 1720 | — | 2 | Me | CH$_2$OMe | SO$_2$Me | |
| 1721 | — | 2 | Me | CH(Me)OMe | SO$_2$Me | |
| 1722 | — | 2 | NO$_2$ | H | Cl | |
| 1723 | — | 2 | NO$_2$ | H | Br | |
| 1724 | — | 2 | NO$_2$ | H | F | |
| 1725 | — | 2 | NO$_2$ | H | CN | |
| 1726 | — | 2 | NO$_2$ | H | SMe | |
| 1727 | — | 2 | NO$_2$ | H | CF$_3$ | |
| 1728 | — | 2 | NO$_2$ | OMe | Cl | |
| 1729 | — | 2 | NO$_2$ | OMe | CF$_3$ | |
| 1730 | — | 2 | CF$_3$ | H | Cl | |
| 1731 | — | 2 | CF$_3$ | H | Br | |
| 1732 | — | 2 | CF$_3$ | H | SMe | |
| 1733 | — | 2 | CF$_3$ | H | CF$_3$ | |
| 1734 | — | 2 | OMe | H | Cl | |
| 1735 | — | 2 | OMe | H | OMe | |
| 1736 | 4-Me | 0 | Cl | H | Cl | Dark green crystal m.p. 55~58° C. |
| 1737 | 4-Me | 0 | Cl | H | SO$_2$Me | |
| 1738 | 4-Me | 0 | Cl | H | NO$_2$ | |
| 1739 | 4-Me | 0 | Cl | H | OMe | |
| 1740 | 4-Me | 0 | Cl | H | Me | |
| 1741 | 4-Me | 0 | Cl | H | Br | |
| 1742 | 4-Me | 0 | Cl | H | F | |
| 1743 | 4-Me | 0 | Cl | H | SMe | |
| 1744 | 4-Me | 0 | Cl | H | S(O)Me | |
| 1745 | 4-Me | 0 | Cl | H | CF$_3$ | |
| 1746 | 4-Me | 0 | Cl | H | CN | |
| 1747 | 4-Me | 0 | Cl | Cl | Cl | |
| 1748 | 4-Me | 0 | Cl | Cl | OMe | |
| 1749 | 4-Me | 0 | Cl | Cl | SMe | |
| 1750 | 4-Me | 0 | Cl | Cl | SO$_2$Me | |
| 1751 | 4-Me | 0 | Cl | Me | Cl | |
| 1752 | 4-Me | 0 | Cl | Me | SO$_2$Me | |
| 1753 | 4-Me | 0 | Cl | OMe | Cl | |
| 1754 | 4-Me | 0 | Cl | OMe | Br | |
| 1755 | 4-Me | 0 | Cl | OMe | SO$_2$Me | |
| 1756 | 4-Me | 0 | Cl | OEt | Br | |
| 1757 | 4-Me | 0 | Br | H | OMe | |
| 1758 | 4-Me | 0 | F | H | F | |
| 1759 | 4-Me | 0 | I | I | I | |
| 1760 | 4-Me | 0 | Me | H | CN | |
| 1761 | 4-Me | 0 | Me | H | Me | |
| 1762 | 4-Me | 0 | Me | H | OMe | |
| 1763 | 4-Me | 0 | Me | Cl | Cl | |
| 1764 | 4-Me | 0 | Me | CO$_2$Me | SO$_2$Me | |
| 1765 | 4-Me | 0 | Me | CH$_2$OMe | SO$_2$Me | |
| 1766 | 4-Me | 0 | Me | CH(Me)OMe | SO$_2$Me | |
| 1767 | 4-Me | 0 | NO$_2$ | H | Cl | |
| 1768 | 4-Me | 0 | NO$_2$ | H | Br | |
| 1769 | 4-Me | 0 | NO$_2$ | H | F | |
| 1770 | 4-Me | 0 | NO$_2$ | H | CN | |
| 1771 | 4-Me | 0 | NO$_2$ | H | SMe | |
| 1772 | 4-Me | 0 | NO$_2$ | H | CF$_3$ | |
| 1773 | 4-Me | 0 | NO$_2$ | OMe | Cl | |
| 1774 | 4-Me | 0 | NO$_2$ | OMe | CF$_3$ | |
| 1775 | 4-Me | 0 | CF$_3$ | H | Cl | |
| 1776 | 4-Me | 0 | CF$_3$ | H | Br | |

TABLE 2-continued

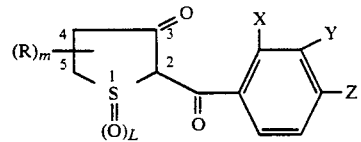

| Compound No. of the present invention | (R)$_m$ | L | X | Y | Z | Characteristic (Physical property) |
|---|---|---|---|---|---|---|
| 1777 | 4-Me | 0 | CF$_3$ | H | SMe | |
| 1778 | 4-Me | 0 | CF$_3$ | H | CF$_3$ | |
| 1779 | 4-Me | 0 | OMe | H | Cl | |
| 1780 | 4-Me | 0 | OMe | H | OMe | |
| 1781 | 4-Me | 1 | Cl | H | Cl | |
| 1782 | 4-Me | 1 | Cl | H | SO$_2$Me | |
| 1783 | 4-Me | 1 | Cl | H | NO$_2$ | |
| 1784 | 4-Me | 1 | Cl | H | OMe | |
| 1785 | 4-Me | 1 | Cl | H | Me | |
| 1786 | 4-Me | 1 | Cl | H | Br | |
| 1787 | 4-Me | 1 | Cl | H | F | |
| 1788 | 4-Me | 1 | Cl | H | SMe | |
| 1789 | 4-Me | 1 | Cl | H | S(O)Me | |
| 1790 | 4-Me | 1 | Cl | H | CF$_3$ | |
| 1791 | 4-Me | 1 | Cl | H | CN | |
| 1792 | 4-Me | 1 | Cl | Cl | Cl | |
| 1793 | 4-Me | 1 | Cl | Cl | OMe | |
| 1794 | 4-Me | 1 | Cl | Cl | SMe | |
| 1795 | 4-Me | 1 | Cl | Cl | SO$_2$Me | |
| 1796 | 4-Me | 1 | Cl | Me | Cl | |
| 1797 | 4-Me | 1 | Cl | Me | SO$_2$Me | |
| 1798 | 4-Me | 1 | Cl | OMe | Cl | |
| 1799 | 4-Me | 1 | Cl | OMe | Br | |
| 1800 | 4-Me | 1 | Cl | OMe | SO$_2$Me | |
| 1801 | 4-Me | 1 | Cl | OEt | Br | |
| 1802 | 4-Me | 1 | Br | H | OMe | |
| 1803 | 4-Me | 1 | F | H | F | |
| 1804 | 4-Me | 1 | I | I | I | |
| 1805 | 4-Me | 1 | Me | H | CN | |
| 1806 | 4-Me | 1 | Me | H | Me | |
| 1807 | 4-Me | 1 | Me | H | OMe | |
| 1808 | 4-Me | 1 | Me | Cl | Cl | |
| 1809 | 4-Me | 1 | Me | CO$_2$Me | SO$_2$Me | |
| 1810 | 4-Me | 1 | Me | CH$_2$OMe | SO$_2$Me | |
| 1811 | 4-Me | 1 | Me | CH(Me)OMe | SO$_2$Me | |
| 1812 | 4-Me | 1 | NO$_2$ | H | Cl | |
| 1813 | 4-Me | 1 | NO$_2$ | H | Br | |
| 1814 | 4-Me | 1 | NO$_2$ | H | F | |
| 1815 | 4-Me | 1 | NO$_2$ | H | CN | |
| 1816 | 4-Me | 1 | NO$_2$ | H | SMe | |
| 1817 | 4-Me | 1 | NO$_2$ | H | CF$_3$ | |
| 1818 | 4-Me | 1 | NO$_2$ | OMe | Cl | |
| 1819 | 4-Me | 1 | NO$_2$ | OMe | CF$_3$ | |
| 1820 | 4-Me | 1 | CF$_3$ | H | Cl | |
| 1821 | 4-Me | 1 | CF$_3$ | H | Br | |
| 1822 | 4-Me | 1 | CF$_3$ | H | SMe | |
| 1823 | 4-Me | 1 | CF$_3$ | H | CF$_3$ | |
| 1824 | 4-Me | 1 | OMe | H | Cl | |
| 1825 | 4-Me | 1 | OMe | H | OMe | |
| 1826 | 4-Me | 2 | Cl | H | Cl | |
| 1827 | 4-Me | 2 | Cl | H | SO$_2$Me | |
| 1828 | 4-Me | 2 | Cl | H | NO$_2$ | |
| 1829 | 4-Me | 2 | Cl | H | OMe | |
| 1830 | 4-Me | 2 | Cl | H | Me | |
| 1831 | 4-Me | 2 | Cl | H | Br | |
| 1832 | 4-Me | 2 | Cl | H | F | |
| 1833 | 4-Me | 2 | Cl | H | SMe | |
| 1834 | 4-Me | 2 | Cl | H | S(O)Me | |
| 1835 | 4-Me | 2 | Cl | H | CF$_3$ | |
| 1836 | 4-Me | 2 | Cl | H | CN | |
| 1837 | 4-Me | 2 | Cl | Cl | Cl | |
| 1838 | 4-Me | 2 | Cl | Cl | OMe | |
| 1839 | 4-Me | 2 | Cl | Cl | SMe | |
| 1840 | 4-Me | 2 | Cl | Cl | SO$_2$Me | |
| 1841 | 4-Me | 2 | Cl | Me | Cl | |
| 1842 | 4-Me | 2 | Cl | Me | SO$_2$Me | |
| 1843 | 4-Me | 2 | Cl | OMe | Cl | |
| 1844 | 4-Me | 2 | Cl | OMe | Br | |
| 1845 | 4-Me | 2 | Cl | OMe | SO$_2$Me | |
| 1846 | 4-Me | 2 | Cl | Oet | Br | |
| 1847 | 4-Me | 2 | Br | H | OMe | |
| 1848 | 4-Me | 2 | F | H | F | |

TABLE 2-continued

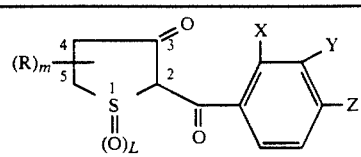

| Compound No. of the present invention | (R)$_m$ | L | X | Y | Z | Characteristic (Physical property) |
|---|---|---|---|---|---|---|
| 1849 | 4-Me | 2 | I | I | I | |
| 1850 | 4-Me | 2 | Me | H | CN | |
| 1851 | 4-Me | 2 | Me | H | Me | |
| 1852 | 4-Me | 2 | Me | H | OMe | |
| 1853 | 4-Me | 2 | Me | Cl | Cl | |
| 1854 | 4-Me | 2 | Me | CO$_2$Me | SO$_2$Me | |
| 1855 | 4-Me | 2 | Me | CH$_2$OMe | SO$_2$Me | |
| 1856 | 4-Me | 2 | Me | CH(Me)OMe | SO$_2$Me | |
| 1857 | 4-Me | 2 | NO$_2$ | H | Cl | |
| 1858 | 4-Me | 2 | NO$_2$ | H | Br | |
| 1859 | 4-Me | 2 | NO$_2$ | H | F | |
| 1860 | 4-Me | 2 | NO$_2$ | H | CN | |
| 1861 | 4-Me | 2 | NO$_2$ | H | SMe | |
| 1862 | 4-Me | 2 | NO$_2$ | H | CF$_3$ | |
| 1863 | 4-Me | 2 | NO$_2$ | OMe | Cl | |
| 1864 | 4-Me | 2 | NO$_2$ | OMe | CF$_3$ | |
| 1865 | 4-Me | 2 | CF$_3$ | H | Cl | |
| 1866 | 4-Me | 2 | CF$_3$ | H | Br | |
| 1867 | 4-Me | 2 | CF$_3$ | H | Br | |
| 1868 | 4-Me | 2 | CF$_3$ | H | CF$_3$ | |
| 1869 | 4-Me | 2 | OMe | H | Cl | |
| 1870 | 4-Me | 2 | OMe | H | OMe | |
| 1871 | 5-Me | 0 | Cl | H | Cl | |
| 1872 | 5-Me | 0 | Cl | H | SO$_2$Me | |
| 1873 | 5-Me | 0 | Cl | H | NO$_2$ | |
| 1874 | 5-Me | 0 | Cl | H | OMe | |
| 1875 | 5-Me | 0 | Cl | H | Me | |
| 1876 | 5-Me | 0 | Cl | H | Br | |
| 1877 | 5-Me | 0 | Cl | H | F | |
| 1878 | 5-Me | 0 | Cl | H | SMe | |
| 1879 | 5-Me | 0 | Cl | H | S(O)Me | |
| 1880 | 5-Me | 0 | Cl | H | CF$_3$ | |
| 1881 | 5-Me | 0 | Cl | H | CN | |
| 1882 | 5-Me | 0 | Cl | Cl | Cl | |
| 1883 | 5-Me | 0 | Cl | Cl | OMe | |
| 1884 | 5-Me | 0 | Cl | Cl | SMe | |
| 1885 | 5-Me | 0 | Cl | Cl | SO$_2$Me | |
| 1886 | 5-Me | 0 | Cl | Me | Cl | |
| 1887 | 5-Me | 0 | Cl | Me | SO$_2$Me | |
| 1888 | 5-Me | 0 | Cl | OMe | Cl | |
| 1889 | 5-Me | 0 | Cl | OMe | Br | |
| 1890 | 5-Me | 0 | Cl | OMe | SO$_2$Me | |
| 1891 | 5-Me | 0 | Cl | OEt | Br | |
| 1892 | 5-Me | 0 | Br | H | OMe | |
| 1893 | 5-Me | 0 | F | H | F | |
| 1894 | 5-Me | 0 | I | I | I | |
| 1895 | 5-Me | 0 | Me | H | CN | |
| 1896 | 5-Me | 0 | Me | H | Me | |
| 1897 | 5-Me | 0 | Me | H | OMe | |
| 1898 | 5-Me | 0 | Me | Cl | Cl | |
| 1899 | 5-Me | 0 | Me | CO$_2$Me | SO$_2$Me | |
| 1900 | 5-Me | 0 | Me | CH$_2$OMe | SO$_2$Me | |
| 1901 | 5-Me | 0 | Me | CH(Me)OMe | SO$_2$Me | |
| 1902 | 5-Me | 0 | NO$_2$ | H | Cl | |
| 1903 | 5-Me | 0 | NO$_2$ | H | Br | |
| 1904 | 5-Me | 0 | NO$_2$ | H | F | |
| 1905 | 5-Me | 0 | NO$_2$ | H | CN | |
| 1906 | 5-Me | 0 | NO$_2$ | H | SMe | |
| 1907 | 5-Me | 0 | NO$_2$ | H | CF$_3$ | |
| 1908 | 5-Me | 0 | NO$_2$ | OMe | Cl | |
| 1909 | 5-Me | 0 | NO$_2$ | OMe | CF$_3$ | |
| 1910 | 5-Me | 0 | CF$_3$ | H | Cl | |
| 1911 | 5-Me | 0 | CF$_3$ | H | Br | |
| 1912 | 5-Me | 0 | CF$_3$ | H | SMe | |
| 1913 | 5-Me | 0 | CF$_3$ | H | CF$_3$ | |
| 1914 | 5-Me | 0 | OMe | H | Cl | |
| 1915 | 5-Me | 0 | OMe | H | OMe | |
| 1916 | 5-Me | 1 | Cl | H | Cl | |
| 1917 | 5-Me | 1 | Cl | H | SO$_2$Me | |
| 1918 | 5-Me | 1 | Cl | H | NO$_2$ | |
| 1919 | 5-Me | 1 | Cl | H | OMe | |
| 1920 | 5-Me | 1 | Cl | H | Me | |

TABLE 2-continued

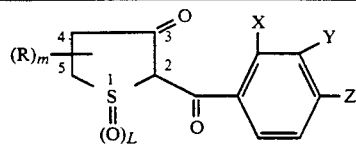

| Compound No. of the present invention | (R)$_m$ | L | X | Y | Z | Characteristic (Physical property) |
|---|---|---|---|---|---|---|
| 1921 | 5-Me | 1 | Cl | H | Br | |
| 1922 | 5-Me | 1 | Cl | H | F | |
| 1923 | 5-Me | 1 | Cl | H | SMe | |
| 1924 | 5-Me | 1 | Cl | H | S(O)Me | |
| 1925 | 5-Me | 1 | Cl | H | CF$_3$ | |
| 1926 | 5-Me | 1 | Cl | H | CN | |
| 1927 | 5-Me | 1 | Cl | Cl | Cl | |
| 1928 | 5-Me | 1 | Cl | Cl | OMe | |
| 1929 | 5-Me | 1 | Cl | Cl | SMe | |
| 1930 | 5-Me | 1 | Cl | Cl | SO$_2$Me | |
| 1931 | 5-Me | 1 | Cl | Me | Cl | |
| 1932 | 5-Me | 1 | Cl | Me | SO$_2$Me | |
| 1933 | 5-Me | 1 | Cl | OMe | Cl | |
| 1934 | 5-Me | 1 | Cl | OMe | Br | |
| 1935 | 5-Me | 1 | Cl | OMe | SO$_2$Me | |
| 1936 | 5-Me | 1 | Cl | OEt | Br | |
| 1937 | 5-Me | 1 | Br | H | OMe | |
| 1938 | 5-Me | 1 | F | H | F | |
| 1939 | 5-Me | 1 | I | I | I | |
| 1940 | 5-Me | 1 | Me | H | CN | |
| 1941 | 5-Me | 1 | Me | H | Me | |
| 1942 | 5-Me | 1 | Me | H | OMe | |
| 1943 | 5-Me | 1 | Me | Cl | Cl | |
| 1944 | 5-Me | 1 | Me | CO$_2$Me | SO$_2$Me | |
| 1945 | 5-Me | 1 | Me | CH$_2$OMe | SO$_2$Me | |
| 1946 | 5-Me | 1 | Me | CH(Me)OMe | SO$_2$Me | |
| 1947 | 5-Me | 1 | NO$_2$ | H | Cl | |
| 1948 | 5-Me | 1 | NO$_2$ | H | Br | |
| 1949 | 5-Me | 1 | NO$_2$ | H | F | |
| 1950 | 5-Me | 1 | NO$_2$ | H | CN | |
| 1951 | 5-Me | 1 | NO$_2$ | H | SMe | |
| 1952 | 5-Me | 1 | NO$_2$ | H | CF$_3$ | |
| 1953 | 5-Me | 1 | NO$_2$ | OMe | Cl | |
| 1954 | 5-Me | 1 | NO$_2$ | OMe | CF$_3$ | |
| 1955 | 5-Me | 1 | CF$_3$ | H | Cl | |
| 1956 | 5-Me | 1 | CF$_3$ | H | Br | |
| 1957 | 5-Me | 1 | CF$_3$ | H | SMe | |
| 1958 | 5-Me | 1 | CF$_3$ | H | CF$_3$ | |
| 1959 | 5-Me | 1 | OMe | H | Cl | |
| 1960 | 5-Me | 1 | OMe | H | OMe | |
| 1961 | 5-Me | 2 | Cl | H | Cl | |
| 1962 | 5-Me | 2 | Cl | H | SO$_2$Me | |
| 1963 | 5-Me | 2 | Cl | H | NO$_2$ | |
| 1964 | 5-Me | 2 | Cl | H | OMe | |
| 1965 | 5-Me | 2 | Cl | H | Me | |
| 1966 | 5-Me | 2 | Cl | H | Br | |
| 1967 | 5-Me | 2 | Cl | H | F | |
| 1968 | 5-Me | 2 | Cl | H | SMe | |
| 1969 | 5-Me | 2 | Cl | H | S(O)Me | |
| 1970 | 5-Me | 2 | Cl | H | CF$_3$ | |
| 1971 | 5-Me | 2 | Cl | H | CN | |
| 1972 | 5-Me | 2 | Cl | Cl | Cl | |
| 1973 | 5-Me | 2 | Cl | Cl | OMe | |
| 1974 | 5-Me | 2 | Cl | Cl | SMe | |
| 1975 | 5-Me | 2 | Cl | Cl | SO$_2$Me | |
| 1976 | 5-Me | 2 | Cl | Me | Cl | |
| 1977 | 5-Me | 2 | Cl | Me | SO$_2$Me | |
| 1978 | 5-Me | 2 | Cl | OMe | Cl | |
| 1979 | 5-Me | 2 | Cl | OMe | Br | |
| 1980 | 5-Me | 2 | Cl | OMe | SO$_2$Me | |
| 1981 | 5-Me | 2 | Cl | OEt | Br | |
| 1982 | 5-Me | 2 | Br | H | OMe | |
| 1983 | 5-Me | 2 | F | H | F | |
| 1984 | 5-Me | 2 | I | I | I | |
| 1985 | 5-Me | 2 | Me | H | CN | |
| 1986 | 5-Me | 2 | Me | H | Me | |
| 1987 | 5-Me | 2 | Me | H | OMe | |
| 1988 | 5-Me | 2 | Me | Cl | Cl | |
| 1989 | 5-Me | 2 | Me | CO$_2$Me | SO$_2$Me | |
| 1990 | 5-Me | 2 | Me | CH$_2$OMe | SO$_2$Me | |
| 1991 | 5-Me | 2 | Me | CH(Me)OMe | SO$_2$Me | |
| 1992 | 5-Me | 2 | NO$_2$ | H | Cl | |

TABLE 2-continued

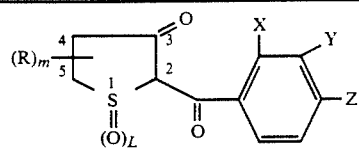

| Compound No. of the present invention | (R)$_m$ | L | X | Y | Z | Characteristic (Physical property) |
|---|---|---|---|---|---|---|
| 1993 | 5-Me | 2 | NO$_2$ | H | Br | |
| 1994 | 5-Me | 2 | NO$_2$ | H | F | |
| 1995 | 5-Me | 2 | NO$_2$ | H | CN | |
| 1996 | 5-Me | 2 | NO$_2$ | H | SMe | |
| 1997 | 5-Me | 2 | NO$_2$ | H | CF$_3$ | |
| 1998 | 5-Me | 2 | NO$_2$ | OMe | Cl | |
| 1999 | 5-Me | 2 | NO$_2$ | OMe | CF$_3$ | |
| 2000 | 5-Me | 2 | CF$_3$ | H | Cl | |
| 2001 | 5-Me | 2 | CF$_3$ | H | Br | |
| 2002 | 5-Me | 2 | CF$_3$ | H | SMe | |
| 2003 | 5-Me | 2 | CF$_3$ | H | CF$_3$ | |
| 2004 | 5-Me | 2 | OMe | H | Cl | |
| 2005 | 5-Me | 2 | OMe | H | OMe | |
| 2006 | 4.4-diMe | 0 | Cl | H | Cl | |
| 2007 | 4.4-diMe | 0 | Cl | H | SO$_2$Me | |
| 2008 | 4.4-diMe | 0 | Cl | H | NO$_2$ | |
| 2009 | 4.4-diMe | 0 | Cl | H | OMe | |
| 2010 | 4.4-diMe | 0 | Cl | H | Me | |
| 2011 | 4.4-diMe | 0 | Cl | H | Br | |
| 2012 | 2.4-diMe | 0 | Cl | H | F | |
| 2013 | 4.4-diMe | 0 | Cl | H | SMe | |
| 2014 | 4.4-diMe | 0 | Cl | H | S(O)Me | |
| 2015 | 4.4-diMe | 0 | Cl | H | CF$_3$ | |
| 2016 | 4.4-diMe | 0 | Cl | H | CN | |
| 2017 | 4.4-diMe | 0 | Cl | Cl | Cl | |
| 2018 | 4.4-diMe | 0 | Cl | Cl | OMe | |
| 2019 | 4.4-diMe | 0 | Cl | Cl | SMe | |
| 2020 | 4.4-diMe | 0 | Cl | Cl | SO$_2$Me | |
| 2021 | 4.4-diMe | 0 | Cl | Me | Cl | |
| 2022 | 4.4-diMe | 0 | Cl | Me | SO$_2$Me | |
| 2023 | 4.4-diMe | 0 | Cl | OMe | Cl | |
| 2024 | 4.4-diMe | 0 | Cl | OMe | Br | |
| 2025 | 4.4-diMe | 0 | Cl | OMe | SO$_2$Me | |
| 2026 | 4.4-diMe | 0 | Cl | OEt | Br | |
| 2027 | 4.4-diMe | 0 | Br | H | OMe | |
| 2028 | 4.4-diMe | 0 | F | H | F | |
| 2029 | 4.4-diMe | 0 | I | I | I | |
| 2030 | 4.4-diMe | 0 | Me | H | CN | |
| 2031 | 4.4-diMe | 0 | Me | H | Me | |
| 2032 | 4.4-diMe | 0 | Me | H | OMe | |
| 2033 | 4.4-diMe | 0 | Me | Cl | Cl | |
| 2034 | 4.4-diMe | 0 | Me | CO$_2$Me | SO$_2$Me | |
| 2035 | 4.4-diMe | 0 | Me | CH$_2$OMe | SO$_2$Me | |
| 2036 | 4.4-diMe | 0 | Me | CH(Me)OMe | SO$_2$Me | |
| 2037 | 4.4-diMe | 0 | NO$_2$ | H | Cl | |
| 2038 | 4.4-diMe | 0 | NO$_2$ | H | Br | |
| 2039 | 4.4-diMe | 0 | NO$_2$ | H | F | |
| 2040 | 4.4-diMe | 0 | NO$_2$ | H | CN | |
| 2041 | 4.4-diMe | 0 | NO$_2$ | H | SMe | |
| 2042 | 4.4-diMe | 0 | NO$_2$ | H | CF$_3$ | |
| 2043 | 4.4-diMe | 0 | NO$_2$ | OMe | Cl | |
| 2044 | 4.4-diMe | 0 | NO$_2$ | OMe | CF$_3$ | |
| 2045 | 4.4-diMe | 0 | CF$_3$ | H | Cl | |
| 2046 | 4.4-diMe | 0 | CF$_3$ | H | Br | |
| 2047 | 4.4-diMe | 0 | CF$_3$ | H | SMe | |
| 2048 | 4.4-diMe | 0 | CF$_3$ | H | CF$_3$ | |
| 2049 | 4.4-diMe | 0 | OMe | H | Cl | |
| 2050 | 4.4-diMe | 0 | OMe | H | OMe | |
| 2051 | 4.4-diMe | 1 | Cl | H | Cl | |
| 2052 | 4.4-diMe | 1 | Cl | H | SO$_2$Me | |
| 2053 | 4.4-diMe | 1 | Cl | H | NO$_2$ | |
| 2054 | 4.4-diMe | 1 | Cl | H | OMe | |
| 2055 | 4.4-diMe | 1 | Cl | H | Me | |
| 2056 | 4.4-diMe | 1 | Cl | H | Br | |
| 2057 | 4.4-diMe | 1 | Cl | H | F | |
| 2058 | 4.4-diMe | 1 | Cl | H | SMe | |
| 2059 | 4.4-diMe | 1 | Cl | H | S(O)Me | |
| 2060 | 4.4-diMe | 1 | Cl | H | CF$_3$ | |
| 2061 | 4.4-diMe | 1 | Cl | H | CN | |
| 2062 | 4.4-diMe | 1 | Cl | Cl | Cl | |
| 2063 | 4.4-diMe | 1 | Cl | Cl | OMe | |
| 2064 | 4.4-diMe | 1 | Cl | Cl | SMe | |

TABLE 2-continued

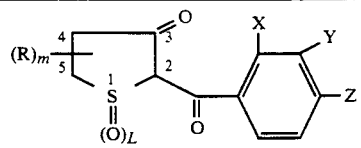

| Compound No. of the present invention | (R)$_m$ | L | X | Y | Z | Characteristic (Physical property) |
|---|---|---|---|---|---|---|
| 2065 | 4.4-diMe | 1 | Cl | Cl | SO$_2$Me | |
| 2066 | 4.4-diMe | 1 | Cl | Me | Cl | |
| 2067 | 4.4-diMe | 1 | Cl | Me | SO$_2$Me | |
| 2068 | 4.4-diMe | 1 | Cl | OMe | Cl | |
| 2069 | 4.4-diMe | 1 | Cl | OMe | Br | |
| 2070 | 4.4-diMe | 1 | Cl | OMe | SO$_2$Me | |
| 2071 | 4.4-diMe | 1 | Cl | OEt | Br | |
| 2072 | 4.4-diMe | 1 | Br | H | OMe | |
| 2073 | 4.4-diMe | 1 | F | H | F | |
| 2074 | 4.4-diMe | 1 | I | I | I | |
| 2075 | 4.4-diMe | 1 | Me | H | CN | |
| 2076 | 4.4-diMe | 1 | Me | H | Me | |
| 2077 | 4.4-diMe | 1 | Me | H | OMe | |
| 2078 | 4.4-diMe | 1 | Me | Cl | Cl | |
| 2079 | 4.4-diMe | 1 | Me | CO$_2$Me | SO$_2$Me | |
| 2080 | 4.4-diMe | 1 | Me | CH$_2$OMe | SO$_2$Me | |
| 2081 | 4.4-diMe | 1 | Me | CH(Me)OMe | SO$_2$Me | |
| 2082 | 4.4-diMe | 1 | NO$_2$ | H | Cl | |
| 2083 | 4.4-diMe | 1 | NO$_2$ | H | Br | |
| 2084 | 4.4-diMe | 1 | NO$_2$ | H | F | |
| 2085 | 4.4-diMe | 1 | NO$_2$ | H | CN | |
| 2086 | 4.4-diMe | 1 | NO$_2$ | H | SMe | |
| 2087 | 4.4-diMe | 1 | NO$_2$ | H | CF$_3$ | |
| 2088 | 4.4-diMe | 1 | NO$_2$ | OMe | Cl | |
| 2089 | 4.4-diMe | 1 | NO$_2$ | OMe | CF$_3$ | |
| 2090 | 4.4-diMe | 1 | CF$_3$ | H | Cl | |
| 2091 | 4.4-diMe | 1 | CF$_3$ | H | Br | |
| 2092 | 4.4-diMe | 1 | CF$_3$ | H | SMe | |
| 2093 | 4.4-diMe | 1 | CF$_3$ | H | CF$_3$ | |
| 2094 | 4.4-diMe | 1 | OMe | H | Cl | |
| 2095 | 4.4-diMe | 1 | OMe | H | OMe | |
| 2096 | 4.4-diMe | 2 | Cl | H | Cl | |
| 2097 | 4.4-diMe | 2 | Cl | H | SO$_2$Me | |
| 2098 | 4.4-diMe | 2 | Cl | H | NO$_2$ | |
| 2099 | 4.4-diMe | 2 | Cl | H | OMe | |
| 2100 | 4.4-diMe | 2 | Cl | H | Me | |
| 2101 | 4.4-diMe | 2 | Cl | H | Br | |
| 2102 | 4.4-diMe | 2 | Cl | H | F | |
| 2103 | 4.4-diMe | 2 | Cl | H | SMe | |
| 2104 | 4.4-diMe | 2 | Cl | H | S(O)Me | |
| 2105 | 4.4-diMe | 2 | Cl | H | CF$_3$ | |
| 2106 | 4.4-diMe | 2 | Cl | H | CN | |
| 2107 | 4.4-diMe | 2 | Cl | Cl | Cl | |
| 2108 | 4.4-diMe | 2 | Cl | Cl | OMe | |
| 2109 | 4.4-diMe | 2 | Cl | Cl | SMe | |
| 2110 | 4.4-diMe | 2 | Cl | Cl | SO$_2$Me | |
| 2111 | 4.4-diMe | 2 | Cl | Me | Cl | |
| 2112 | 4.4-diMe | 2 | Cl | Me | SO$_2$Me | |
| 2113 | 4.4-diMe | 2 | Cl | OMe | Cl | |
| 2114 | 4.4-diMe | 2 | Cl | OMe | Br | |
| 2115 | 4.4-diMe | 2 | Cl | OMe | SO$_2$Me | |
| 2116 | 4.4-diMe | 2 | Cl | OEt | Br | |
| 2117 | 4.4-diMe | 2 | Br | H | OMe | |
| 2118 | 4.4-diMe | 2 | F | H | F | |
| 2119 | 4.4-diMe | 2 | I | I | I | |
| 2120 | 4.4-diMe | 2 | Me | H | CN | |
| 2121 | 4.4-diMe | 2 | Me | H | Me | |
| 2122 | 4.4-diMe | 2 | Me | H | OMe | |
| 2123 | 4.4-diMe | 2 | Me | Cl | Cl | |
| 2124 | 4.4-diMe | 2 | Me | CO$_2$Me | SO$_2$Me | |
| 2125 | 4.4-diMe | 2 | Me | CH$_2$OMe | SO$_2$Me | |
| 2126 | 4.4-diMe | 2 | Me | CH(Me)OMe | SO$_2$Me | |
| 2127 | 4.4-diMe | 2 | NO$_2$ | H | Cl | |
| 2128 | 4.4-diMe | 2 | NO$_2$ | H | Br | |
| 2129 | 4.4-diMe | 2 | NO$_2$ | H | F | |
| 2130 | 4.4-diMe | 2 | NO$_2$ | H | CN | |
| 2131 | 4.4-diMe | 2 | NO$_2$ | H | SMe | |
| 2132 | 4.4-diMe | 2 | NO$_2$ | H | CF$_3$ | |
| 2133 | 4.4-diMe | 2 | NO$_2$ | OMe | Cl | |
| 2134 | 4.4-diMe | 2 | NO$_2$ | OMe | CF$_3$ | |
| 2135 | 4.4-diMe | 2 | CF$_3$ | H | Cl | |
| 2136 | 4.4-diMe | 2 | CF$_3$ | H | Br | |

TABLE 2-continued

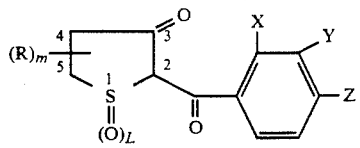

| Compound No. of the present invention | (R)$_m$ | L | X | Y | Z | Characteristic (Physical property) |
|---|---|---|---|---|---|---|
| 2137 | 4.4-diMe | 2 | CF$_3$ | H | SMe | |
| 2138 | 4.4-diMe | 2 | CF$_3$ | H | CF$_3$ | |
| 2139 | 4.4-diMe | 2 | OMe | H | Cl | |
| 2140 | 4.4-diMe | 2 | OMe | H | OMe | |
| 2141 | 5.5-diMe | 0 | Cl | H | Cl | |
| 2142 | 5.5-diMe | 0 | Cl | H | SO$_2$Me | |
| 2143 | 5.5-diMe | 0 | Cl | H | NO$_2$ | |
| 2144 | 5.5-diMe | 0 | Cl | H | OMe | |
| 2145 | 5.5-diMe | 0 | Cl | H | Me | |
| 2146 | 5.5-diMe | 0 | Cl | H | Br | |
| 2147 | 5.5-diMe | 0 | Cl | H | F | |
| 2148 | 5.5-diMe | 0 | Cl | H | SMe | |
| 2149 | 5.5-diMe | 0 | Cl | H | S(O)Me | |
| 2150 | 5.5-diMe | 0 | Cl | H | CF$_3$ | |
| 2151 | 5.5-diMe | 0 | Cl | H | CN | |
| 2152 | 5.5-diMe | 0 | Cl | Cl | Cl | |
| 2153 | 5.5-diMe | 0 | Cl | Cl | OMe | |
| 2154 | 5.5-diMe | 0 | Cl | Cl | SMe | |
| 2155 | 5.5-diMe | 0 | Cl | Cl | SO$_2$Me | |
| 2156 | 5.5-diMe | 0 | Cl | Me | Cl | |
| 2157 | 5.5-diMe | 0 | Cl | Me | SO$_2$Me | |
| 2158 | 5.5-diMe | 0 | Cl | OMe | Cl | |
| 2159 | 5.5-diMe | 0 | Cl | OMe | Br | |
| 2160 | 5.5-diMe | 0 | Cl | OMe | SO$_2$Me | |
| 2161 | 5.5-diMe | 0 | Cl | OEt | Br | |
| 2162 | 5.5-diMe | 0 | Br | H | OMe | |
| 2163 | 5.5-diMe | 0 | F | H | F | |
| 2164 | 5.5-diMe | 0 | I | I | I | |
| 2165 | 5.5-diMe | 0 | Me | H | CN | |
| 2166 | 5.5-diMe | 0 | Me | H | Me | |
| 2167 | 5.5-diMe | 0 | Me | H | OMe | |
| 2168 | 5.5-diMe | 0 | Me | Cl | Cl | |
| 2169 | 5.5-diMe | 0 | Me | CO$_2$Me | SO$_2$Me | |
| 2170 | 5.5-diMe | 0 | Me | CH$_2$OMe | SO$_2$Me | |
| 2171 | 5.5-diMe | 0 | Me | CH(Me)OMe | SO$_2$Me | |
| 2172 | 5.5-diMe | 0 | NO$_2$ | H | Cl | |
| 2173 | 5.5-diMe | 0 | NO$_2$ | H | Br | |
| 2174 | 5.5-diMe | 0 | NO$_2$ | H | F | |
| 2175 | 5.5-diMe | 0 | NO$_2$ | H | CN | |
| 2176 | 5.5-diMe | 0 | NO$_2$ | H | SMe | |
| 2177 | 5.5-diMe | 0 | NO$_2$ | H | CF$_3$ | |
| 2178 | 5.5-diMe | 0 | NO$_2$ | OMe | Cl | |
| 2179 | 5.5-diMe | 0 | NO$_2$ | OMe | CF$_3$ | |
| 2180 | 5.5-diMe | 0 | CF$_3$ | H | Cl | |
| 2181 | 5.5-diMe | 0 | CF$_3$ | H | Br | |
| 2182 | 5.5-diMe | 0 | CF$_3$ | H | SMe | |
| 2183 | 5.5-diMe | 0 | CF$_3$ | H | CF$_3$ | |
| 2184 | 5.5-diMe | 0 | OMe | H | Cl | |
| 2185 | 5.5-diMe | 0 | OMe | H | OMe | |
| 2186 | 5.5-diMe | 0 | Cl | H | Cl | |
| 2187 | 5.5-diMe | 0 | Cl | H | SO$_2$Me | |
| 2188 | 5.5-diMe | 0 | Cl | H | NO$_2$ | |
| 2189 | 5.5-diMe | 0 | Cl | H | OMe | |
| 2190 | 5.5-diMe | 0 | Cl | H | Me | |
| 2191 | 5.5-diMe | 1 | Cl | H | Br | |
| 2192 | 5.5-diMe | 1 | Cl | H | F | |
| 2193 | 5.5-diMe | 1 | Cl | H | SMe | |
| 2194 | 5.5-diMe | 1 | Cl | H | S(O)Me | |
| 2195 | 5.5-diMe | 1 | Cl | H | CF$_3$ | |
| 2196 | 5.5-diMe | 1 | Cl | H | CN | |
| 2197 | 5.5-diMe | 1 | Cl | Cl | Cl | |
| 2198 | 5.5-diMe | 1 | Cl | Cl | OMe | |
| 2199 | 5.5-diMe | 1 | Cl | Cl | SMe | |
| 2200 | 5.5-diMe | 1 | Cl | Cl | SO$_2$Me | |
| 2201 | 5.5-diMe | 1 | Cl | Me | Cl | |
| 2202 | 5.5-diMe | 1 | Cl | Me | SO$_2$Me | |
| 2203 | 5.5-diMe | 1 | Cl | OMe | Cl | |
| 2204 | 5.5-diMe | 1 | Cl | OMe | Br | |
| 2205 | 5.5-diMe | 1 | Cl | OMe | SO$_2$Me | |
| 2206 | 5.5-diMe | 1 | Cl | OEt | Br | |
| 2207 | 5.5-diMe | 1 | Br | H | OMe | |
| 2208 | 5.5-diMe | 1 | F | H | F | |

TABLE 2-continued

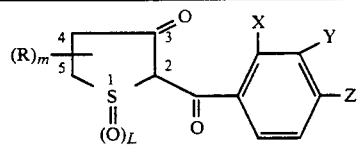

| Compound No. of the present invention | (R)$_m$ | L | X | Y | Z | Characteristic (Physical property) |
|---|---|---|---|---|---|---|
| 2209 | 5,5-diMe | 1 | I | I | I | |
| 2210 | 5,5-diMe | 1 | Me | H | CN | |
| 2211 | 5,5-diMe | 1 | Me | H | Me | |
| 2212 | 5,5-diMe | 1 | Me | H | OMe | |
| 2213 | 5,5-diMe | 1 | Me | Cl | Cl | |
| 2214 | 5,5-diMe | 1 | Me | CO$_2$Me | SO$_2$Me | |
| 2215 | 5,5-diMe | 1 | Me | CH$_2$OMe | SO$_2$Me | |
| 2216 | 5,5-diMe | 1 | Me | CH(Me)OMe | SO$_2$Me | |
| 2217 | 5,5-diMe | 1 | NO$_2$ | H | Cl | |
| 2218 | 5,5-diMe | 1 | NO$_2$ | H | Br | |
| 2219 | 5,5-diMe | 1 | NO$_2$ | H | F | |
| 2220 | 5,5-diMe | 1 | NO$_2$ | H | CN | |
| 2221 | 5,5-diMe | 1 | NO$_2$ | H | SMe | |
| 2222 | 5,5-diMe | 1 | NO$_2$ | H | CF$_3$ | |
| 2223 | 5,5-diMe | 1 | NO$_2$ | OMe | Cl | |
| 2224 | 5,5-diMe | 1 | NO$_2$ | OMe | CF$_3$ | |
| 2225 | 5,5-diMe | 1 | CF$_3$ | H | Cl | |
| 2226 | 5,5-diMe | 1 | CF$_3$ | H | Br | |
| 2227 | 5,5-diMe | 1 | CF$_3$ | H | SMe | |
| 2228 | 5,5-diMe | 1 | CF$_3$ | H | CF$_3$ | |
| 2229 | 5,5-diMe | 1 | OMe | H | Cl | |
| 2230 | 5,5-diMe | 1 | OMe | H | OMe | |
| 2231 | 5,5-diMe | 2 | Cl | H | Cl | |
| 2232 | 5,5-diMe | 2 | Cl | H | SO$_2$Me | |
| 2233 | 5,5-diMe | 2 | Cl | H | NO$_2$ | |
| 2234 | 5,5-diMe | 2 | Cl | H | OMe | |
| 2235 | 5,5-diMe | 2 | Cl | H | Me | |
| 2236 | 5,5-diMe | 2 | Cl | H | Br | |
| 2237 | 5,5-diMe | 2 | Cl | H | F | |
| 2238 | 5,5-diMe | 2 | Cl | H | SMe | |
| 2239 | 5,5-diMe | 2 | Cl | H | S(O)Me | |
| 2240 | 5,5-diMe | 2 | Cl | H | CF$_3$ | |
| 2241 | 5,5-diMe | 2 | Cl | H | CN | |
| 2242 | 5,5-diMe | 2 | Cl | Cl | Cl | |
| 2243 | 5,5-diMe | 2 | Cl | Cl | OMe | |
| 2244 | 5,5-diMe | 2 | Cl | Cl | SMe | |
| 2245 | 5,5-diMe | 2 | Cl | Cl | SO$_2$Me | |
| 2246 | 5,5-diMe | 2 | Cl | Me | Cl | |
| 2247 | 5,5-diMe | 2 | Cl | Me | SO$_2$Me | |
| 2248 | 5,5-diMe | 2 | Cl | OMe | Cl | |
| 2249 | 5,5-diMe | 2 | Cl | OMe | Br | |
| 2250 | 5,5-diMe | 2 | Cl | OMe | SO$_2$Me | |
| 2251 | 5,5-diMe | 2 | Cl | OEt | Br | |
| 2252 | 5,5-diMe | 2 | Br | H | OMe | |
| 2253 | 5,5-diMe | 2 | F | H | F | |
| 2254 | 5,5-diMe | 2 | I | I | I | |
| 2255 | 5,5-diMe | 2 | Me | H | CN | |
| 2256 | 5,5-diMe | 2 | Me | H | Me | |
| 2257 | 5,5-diMe | 2 | Me | H | OMe | |
| 2258 | 5,5-diMe | 2 | Me | Cl | Cl | |
| 2259 | 5,5-diMe | 2 | Me | CO$_2$Me | SO$_2$Me | |
| 2260 | 5,5-diMe | 2 | Me | CH$_2$OMe | SO$_2$Me | |
| 2261 | 5,5-diMe | 2 | Me | CH(Me)OMe | SO$_2$Me | |
| 2262 | 5,5-diMe | 2 | NO$_2$ | H | Cl | |
| 2263 | 5,5-diMe | 2 | NO$_2$ | H | Br | |
| 2264 | 5,5-diMe | 2 | NO$_2$ | H | F | |
| 2265 | 5,5-diMe | 2 | NO$_2$ | H | CN | |
| 2266 | 5,5-diMe | 2 | NO$_2$ | H | SMe | |
| 2267 | 5,5-diMe | 2 | NO$_2$ | H | CF$_3$ | |
| 2268 | 5,5-diMe | 2 | NO$_2$ | OMe | Cl | |
| 2269 | 5,5-diMe | 2 | NO$_2$ | OMe | CF$_3$ | |
| 2270 | 5,5-diMe | 2 | CF$_3$ | H | Cl | |
| 2271 | 5,5-diMe | 2 | CF$_3$ | H | Br | |
| 2272 | 5,5-diMe | 2 | CF$_3$ | H | SMe | |
| 2273 | 5,5-diMe | 2 | CF$_3$ | H | CF$_3$ | |
| 2274 | 5,5-diMe | 2 | OMe | H | Cl | |
| 2275 | 5,5-diMe | 2 | OMe | H | OMe | |
| 2276 | 4,5-diMe | 0 | Cl | H | Cl | |
| 2277 | 4,5-diMe | 0 | Cl | H | SO$_2$Me | |
| 2278 | 4,5-diMe | 0 | Cl | H | NO$_2$ | |
| 2279 | 4,5-diMe | 0 | Cl | H | OMe | |
| 2280 | 4,5-diMe | 0 | Cl | H | Me | |

TABLE 2-continued

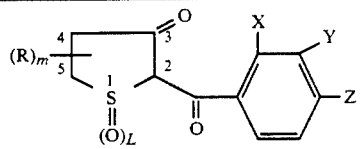

| Compound No. of the present invention | (R)$_m$ | L | X | Y | Z | Characteristic (Physical property) |
|---|---|---|---|---|---|---|
| 2281 | 4.5-diMe | 0 | Cl | H | Br | |
| 2282 | 4.5-diMe | 0 | Cl | H | F | |
| 2283 | 4.5-diMe | 0 | Cl | H | SMe | |
| 2284 | 4.5-diMe | 0 | Cl | H | S(O)Me | |
| 2285 | 4.5-diMe | 0 | Cl | H | CF$_3$ | |
| 2286 | 4.5-diMe | 0 | Cl | H | CN | |
| 2287 | 4.5-diMe | 0 | Cl | Cl | Cl | |
| 2288 | 4.5-diMe | 0 | Cl | Cl | OMe | |
| 2289 | 4.5-diMe | 0 | Cl | Cl | SMe | |
| 2290 | 4.5-diMe | 0 | Cl | Cl | SO$_2$Me | |
| 2291 | 4.5-diMe | 0 | Cl | Me | Cl | |
| 2292 | 4.5-diMe | 0 | Cl | Me | SO$_2$Me | |
| 2293 | 4.5-diMe | 0 | Cl | OMe | Cl | |
| 2294 | 4.5-diMe | 0 | Cl | OMe | Br | |
| 2295 | 4.5-diMe | 0 | Cl | OMe | SO$_2$Me | |
| 2296 | 4.5-diMe | 0 | Cl | OEt | Br | |
| 2297 | 4.5-diMe | 0 | Br | H | OMe | |
| 2298 | 4.5-diMe | 0 | F | H | F | |
| 2299 | 4.5-diMe | 0 | I | I | I | |
| 2300 | 4.5-diMe | 0 | Me | H | CN | |
| 2301 | 4.5-diMe | 0 | Me | H | Me | |
| 2302 | 4.5-diMe | 0 | Me | H | OMe | |
| 2303 | 4.5-diMe | 0 | Me | Cl | Cl | |
| 2304 | 4.5-diMe | 0 | Me | CO$_2$Me | SO$_2$Me | |
| 2305 | 4.5-diMe | 0 | Me | CH$_2$OMe | SO$_2$Me | |
| 2306 | 4.5-diMe | 0 | Me | CH(Me)OMe | SO$_2$Me | |
| 2307 | 4.5-diMe | 0 | NO$_2$ | H | Cl | |
| 2308 | 4.5-diMe | 0 | NO$_2$ | H | Br | |
| 2309 | 4.5-diMe | 0 | NO$_2$ | H | F | |
| 2310 | 4.5-diMe | 0 | NO$_2$ | H | CN | |
| 2311 | 4.5-diMe | 0 | NO$_2$ | H | SMe | |
| 2312 | 4.5-diMe | 0 | NO$_2$ | H | CF$_3$ | |
| 2313 | 4.5-diMe | 0 | NO$_2$ | OMe | Cl | |
| 2314 | 4.5-diMe | 0 | NO$_2$ | OMe | CF$_3$ | |
| 2315 | 4.5-diMe | 0 | CF$_3$ | H | Cl | |
| 2316 | 4.5-diMe | 0 | CF$_3$ | H | Br | |
| 2317 | 4.5-diMe | 0 | CF$_3$ | H | SMe | |
| 2318 | 4.5-diMe | 0 | CF$_3$ | H | CF$_3$ | |
| 2319 | 4.5-diMe | 0 | OMe | H | Cl | |
| 2320 | 4.5-diMe | 0 | OMe | H | OMe | |
| 2321 | 4.5-diMe | 1 | Cl | H | Cl | |
| 2322 | 4.5-diMe | 1 | Cl | H | SO$_2$Me | |
| 2323 | 4.5-diMe | 1 | Cl | H | NO$_2$ | |
| 2324 | 4.5-diMe | 1 | Cl | H | OMe | |
| 2325 | 4.5-diMe | 1 | Cl | H | Me | |
| 2326 | 4.5-diMe | 1 | Cl | H | Br | |
| 2327 | 4.5-diMe | 1 | Cl | H | F | |
| 2328 | 4.5-diMe | 1 | Cl | H | SMe | |
| 2329 | 4.5-diMe | 1 | Cl | H | S(O)Me | |
| 2330 | 4.5-diMe | 1 | Cl | H | CF$_3$ | |
| 2331 | 4.5-diMe | 1 | Cl | H | CN | |
| 2332 | 4.5-diMe | 1 | Cl | Cl | Cl | |
| 2333 | 4.5-diMe | 1 | Cl | Cl | OMe | |
| 2334 | 4.5-diMe | 1 | Cl | Cl | SMe | |
| 2335 | 4.5-diMe | 1 | Cl | Cl | SO$_2$Me | |
| 2336 | 4.5-diMe | 1 | Cl | Me | Cl | |
| 2337 | 4.5-diMe | 1 | Cl | Me | SO$_2$Me | |
| 2338 | 4.5-diMe | 1 | Cl | OMe | Cl | |
| 2339 | 4.5-diMe | 1 | Cl | OMe | Br | |
| 2340 | 4.5-diMe | 1 | Cl | OMe | SO$_2$Me | |
| 2341 | 4.5-diMe | 1 | Cl | OEt | Br | |
| 2342 | 4.5-diMe | 1 | Br | H | OMe | |
| 2343 | 4.5-diMe | 1 | F | H | F | |
| 2344 | 4.5-diMe | 1 | I | I | I | |
| 2345 | 4.5-diMe | 1 | Me | H | CN | |
| 2346 | 4.5-diMe | 1 | Me | H | Me | |
| 2347 | 4.5-diMe | 1 | Me | H | OMe | |
| 2348 | 4.5-diMe | 1 | Me | Cl | Cl | |
| 2349 | 4.5-diMe | 1 | Me | CO$_2$Me | SO$_2$Me | |
| 2350 | 4.5-diMe | 1 | Me | CH$_2$OMe | SO$_2$Me | |
| 2351 | 4.5-diMe | 1 | Me | CH(Me)OMe | SO$_2$Me | |
| 2352 | 4.5-diMe | 1 | NO$_2$ | H | Cl | |

TABLE 2-continued

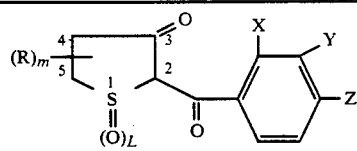

| Compound No. of the present invention | (R)$_m$ | L | X | Y | Z | Characteristic (Physical property) |
|---|---|---|---|---|---|---|
| 2353 | 4.5-diMe | 1 | NO$_2$ | H | Br | |
| 2354 | 4.5-diMe | 1 | NO$_2$ | H | F | |
| 2355 | 4.5-diMe | 1 | NO$_2$ | H | CN | |
| 2356 | 4.5-diMe | 1 | NO$_2$ | H | SMe | |
| 2357 | 4.5-diMe | 1 | NO$_2$ | H | CF$_3$ | |
| 2358 | 4.5-diMe | 1 | NO$_2$ | OMe | Cl | |
| 2359 | 4.5-diMe | 1 | NO$_2$ | OMe | CF$_3$ | |
| 2360 | 4.5-diMe | 1 | CF$_3$ | H | Cl | |
| 2361 | 4.5-diMe | 1 | CF$_3$ | H | Br | |
| 2362 | 4.5-diMe | 1 | CF$_3$ | H | SMe | |
| 2363 | 4.5-diMe | 1 | CF$_3$ | H | CF$_3$ | |
| 2364 | 4.5-diMe | 1 | OMe | H | Cl | |
| 2365 | 4.5-diMe | 1 | OMe | H | OMe | |
| 2366 | 4.5-diMe | 2 | Cl | H | Cl | |
| 2367 | 4.5-diMe | 2 | Cl | H | SO$_2$Me | |
| 2368 | 4.5-diMe | 2 | Cl | H | NO$_2$ | |
| 2369 | 4.5-diMe | 2 | Cl | H | OMe | |
| 2370 | 4.5-diMe | 2 | Cl | H | Me | |
| 2371 | 4.5-diMe | 2 | Cl | H | Br | |
| 2372 | 4.5-diMe | 2 | Cl | H | F | |
| 2373 | 4.5-diMe | 2 | Cl | H | SMe | |
| 2374 | 4.5-diMe | 2 | Cl | H | S(O)Me | |
| 2375 | 4.5-diMe | 2 | Cl | H | CF$_3$ | |
| 2376 | 4.5-diMe | 2 | Cl | H | CN | |
| 2377 | 4.5-diMe | 2 | Cl | Cl | Cl | |
| 2378 | 4.5-diMe | 2 | Cl | Cl | OMe | |
| 2379 | 4.5-diMe | 2 | Cl | Cl | SMe | |
| 2380 | 4.5-diMe | 2 | Cl | Cl | SO$_2$Me | |
| 2381 | 4.5-diMe | 2 | Cl | Me | Cl | |
| 2382 | 4.5-diMe | 2 | Cl | Me | SO$_2$Me | |
| 2383 | 4.5-diMe | 2 | Cl | OMe | Cl | |
| 2384 | 4.5-diMe | 2 | Cl | OMe | Br | |
| 2385 | 4.5-diMe | 2 | Cl | OMe | SO$_2$Me | |
| 2386 | 4.5-diMe | 2 | Cl | OEt | Br | |
| 2387 | 4.5-diMe | 2 | Br | H | OMe | |
| 2388 | 4.5-diMe | 2 | F | H | F | |
| 2389 | 4.5-diMe | 2 | I | I | I | |
| 2390 | 4.5-diMe | 2 | Me | H | CN | |
| 2391 | 4.5-diMe | 2 | Me | H | Me | |
| 2392 | 4.5-diMe | 2 | Me | H | OMe | |
| 2393 | 4.5-diMe | 2 | Me | Cl | Cl | |
| 2394 | 4.5-diMe | 2 | Me | CO$_2$Me | SO$_2$Me | |
| 2395 | 4.5-diMe | 2 | Me | CH$_2$OMe | SO$_2$Me | |
| 2396 | 4.5-diMe | 2 | Me | CH(Me)OMe | SO$_2$Me | |
| 2397 | 4.5-diMe | 2 | NO$_2$ | H | Cl | |
| 2398 | 4.5-diMe | 2 | NO$_2$ | H | Br | |
| 2399 | 4.5-diMe | 2 | NO$_2$ | H | F | |
| 2400 | 4.5-diMe | 2 | NO$_2$ | H | CN | |
| 2401 | 4.5-diMe | 2 | NO$_2$ | H | SMe | |
| 2402 | 4.5-diMe | 2 | NO$_2$ | H | CF$_3$ | |
| 2403 | 4.5-diMe | 2 | NO$_2$ | OMe | Cl | |
| 2404 | 4.5-diMe | 2 | NO$_2$ | OMe | CF$_3$ | |
| 2405 | 4.5-diMe | 2 | CF$_3$ | H | Cl | |
| 2406 | 4.5-diMe | 2 | CF$_3$ | H | Br | |
| 2407 | 4.5-diMe | 2 | CF$_3$ | H | SMe | |
| 2408 | 4.5-diMe | 2 | CF$_3$ | H | CF$_3$ | |
| 2409 | 4.5-diMe | 2 | OMe | H | Cl | |
| 2410 | 4.5-diMe | 2 | OMe | H | OMe | |
| 2411 | 4-Ph | 0 | Cl | H | Cl | |
| 2412 | 4-Ph | 0 | Cl | H | SO$_2$Me | |
| 2413 | 4-Ph | 0 | Cl | H | NO$_2$ | |
| 2414 | 4-Ph | 0 | Cl | H | OMe | |
| 2415 | 4-Ph | 0 | Cl | H | Me | |
| 2416 | 4-Ph | 0 | Cl | H | Br | |
| 2417 | 4-Ph | 0 | Cl | H | F | |
| 2418 | 4-Ph | 0 | Cl | H | SMe | |
| 2419 | 4-Ph | 0 | Cl | H | S(O)Me | |
| 2420 | 4-Ph | 0 | Cl | H | CF$_3$ | |
| 2421 | 4-Ph | 0 | Cl | H | CN | |
| 2422 | 4-Ph | 0 | Cl | Cl | Cl | |
| 2423 | 4-Ph | 0 | Cl | Cl | OMe | |
| 2424 | 4-Ph | 0 | Cl | Cl | SMe | |

TABLE 2-continued

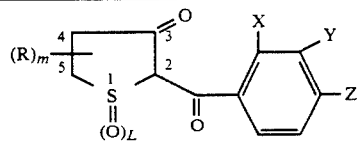

| Compound No. of the present invention | (R)$_m$ | L | X | Y | Z | Characteristic (Physical property) |
|---|---|---|---|---|---|---|
| 2425 | 4-Ph | 0 | Cl | Cl | SO$_2$Me | |
| 2426 | 4-Ph | 0 | Cl | Me | Cl | |
| 2427 | 4-Ph | 0 | Cl | Me | SO$_2$Me | |
| 2428 | 4-Ph | 0 | Cl | OMe | Cl | |
| 2429 | 4-Ph | 0 | Cl | OMe | Br | |
| 2430 | 4-Ph | 0 | Cl | OMe | SO$_2$Me | |
| 2431 | 4-Ph | 0 | Cl | OEt | Br | |
| 2432 | 4-Ph | 0 | Br | H | OMe | |
| 2433 | 4-Ph | 0 | F | H | F | |
| 2434 | 4-Ph | 0 | I | I | I | |
| 2435 | 4-Ph | 0 | Me | H | CN | |
| 2436 | 4-Ph | 0 | Me | H | Me | |
| 2437 | 4-Ph | 0 | Me | H | OMe | |
| 2438 | 4-Ph | 0 | Me | Cl | Cl | |
| 2439 | 4-Ph | 0 | Me | CO$_2$Me | SO$_2$Me | |
| 2440 | 4-Ph | 0 | Me | CH$_2$OMe | SO$_2$Me | |
| 2441 | 4-Ph | 0 | Me | CH(Me)OMe | SO$_2$Me | |
| 2442 | 4-Ph | 0 | NO$_2$ | H | Cl | |
| 2443 | 4-Ph | 0 | NO$_2$ | H | Br | |
| 2444 | 4-Ph | 0 | NO$_2$ | H | F | |
| 2445 | 4-Ph | 0 | NO$_2$ | H | CN | |
| 2446 | 4-Ph | 0 | NO$_2$ | H | SMe | |
| 2447 | 4-Ph | 0 | NO$_2$ | H | CF$_3$ | |
| 2448 | 4-Ph | 0 | NO$_2$ | OMe | Cl | |
| 2449 | 4-Ph | 0 | NO$_2$ | OMe | CF$_3$ | |
| 2450 | 4-Ph | 0 | CF$_3$ | H | Cl | |
| 2451 | 4-Ph | 0 | CF$_3$ | H | Br | |
| 2452 | 4-Ph | 0 | CF$_3$ | H | SMe | |
| 2453 | 4-Ph | 0 | CF$_3$ | H | CF$_3$ | |
| 2454 | 4-Ph | 0 | OMe | H | Cl | |
| 2455 | 4-Ph | 0 | OMe | H | OMe | |
| 2456 | 4-Ph | 1 | Cl | H | Cl | |
| 2457 | 4-Ph | 1 | Cl | H | SO$_2$Me | |
| 2458 | 4-Ph | 1 | Cl | H | NO$_2$ | |
| 2459 | 4-Ph | 1 | Cl | H | OMe | |
| 2460 | 4-Ph | 1 | Cl | H | Me | |
| 2461 | 4-Ph | 1 | Cl | H | Br | |
| 2462 | 4-Ph | 1 | Cl | H | F | |
| 2463 | 4-Ph | 1 | Cl | H | SMe | |
| 2464 | 4-Ph | 1 | Cl | H | S(O)Me | |
| 2465 | 4-Ph | 1 | Cl | H | CF$_3$ | |
| 2466 | 4-Ph | 1 | Cl | H | CN | |
| 2467 | 4-Ph | 1 | Cl | Cl | Cl | |
| 2468 | 4-Ph | 1 | Cl | Cl | OMe | |
| 2469 | 4-Ph | 1 | Cl | Cl | SMe | |
| 2470 | 4-Ph | 1 | Cl | Cl | SO$_2$Me | |
| 2471 | 4-Ph | 1 | Cl | Me | Cl | |
| 2472 | 4-Ph | 1 | Cl | Me | SO$_2$Me | |
| 2473 | 4-Ph | 1 | Cl | OMe | Cl | |
| 2474 | 4-Ph | 1 | Cl | OMe | Br | |
| 2475 | 4-Ph | 1 | Cl | OMe | SO$_2$Me | |
| 2476 | 4-Ph | 1 | Cl | OEt | Br | |
| 2477 | 4-Ph | 1 | Br | H | OMe | |
| 2478 | 4-Ph | 1 | F | H | F | |
| 2479 | 4-Ph | 1 | I | I | I | |
| 2480 | 4-Ph | 1 | Me | H | CN | |
| 2481 | 4-Ph | 1 | Me | H | Me | |
| 2482 | 4-Ph | 1 | Me | H | OMe | |
| 2483 | 4-Ph | 1 | Me | Cl | Cl | |
| 2484 | 4-Ph | 1 | Me | CO$_2$Me | SO$_2$Me | |
| 2485 | 4-Ph | 1 | Me | CH$_2$OMe | SO$_2$Me | |
| 2486 | 4-Ph | 1 | Me | CH(Me)OMe | SO$_2$Me | |
| 2487 | 4-Ph | 1 | NO$_2$ | H | Cl | |
| 2488 | 4-Ph | 1 | NO$_2$ | H | Br | |
| 2489 | 4-Ph | 1 | NO$_2$ | H | F | |
| 2490 | 4-Ph | 1 | NO$_2$ | H | CN | |
| 2491 | 4-Ph | 1 | NO$_2$ | H | SMe | |
| 2492 | 4-Ph | 1 | NO$_2$ | H | CF$_3$ | |
| 2493 | 4-Ph | 1 | NO$_2$ | OMe | Cl | |
| 2494 | 4-Ph | 1 | NO$_2$ | OMe | CF$_3$ | |
| 2495 | 4-Ph | 1 | CF$_3$ | H | Cl | |
| 2496 | 4-Ph | 1 | CF$_3$ | H | Br | |

TABLE 2-continued

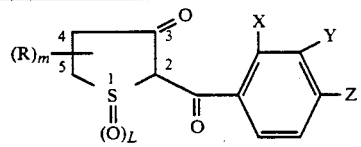

| Compound No. of the present invention | (R)$_m$ | L | X | Y | Z | Characteristic (Physical property) |
|---|---|---|---|---|---|---|
| 2497 | 4-Ph | 1 | CF$_3$ | H | SMe | |
| 2498 | 4-Ph | 1 | CF$_3$ | H | CF$_3$ | |
| 2499 | 4-Ph | 1 | OMe | H | Cl | |
| 2500 | 4-Ph | 1 | OMe | H | OMe | |
| 2501 | 4-Ph | 2 | Cl | H | Cl | |
| 2502 | 4-Ph | 2 | Cl | H | SO$_2$Me | |
| 2503 | 4-Ph | 2 | Cl | H | NO$_2$ | |
| 2504 | 4-Ph | 2 | Cl | H | OMe | |
| 2505 | 4-Ph | 2 | Cl | H | Me | |
| 2506 | 4-Ph | 2 | Cl | H | Br | |
| 2507 | 4-Ph | 2 | Cl | H | F | |
| 2508 | 4-Ph | 2 | Cl | H | SMe | |
| 2509 | 4-Ph | 2 | Cl | H | S(O)Me | |
| 2510 | 4-Ph | 2 | Cl | H | CF$_3$ | |
| 2511 | 4-Ph | 2 | Cl | H | CN | |
| 2512 | 4-Ph | 2 | Cl | Cl | Cl | |
| 2513 | 4-Ph | 2 | Cl | Cl | OMe | |
| 2514 | 4-Ph | 2 | Cl | Cl | SMe | |
| 2515 | 4-Ph | 2 | Cl | Cl | SO$_2$Me | |
| 2516 | 4-Ph | 2 | Cl | Me | Cl | |
| 2517 | 4-Ph | 2 | Cl | Me | SO$_2$Me | |
| 2518 | 4-Ph | 2 | Cl | OMe | Cl | |
| 2519 | 4-Ph | 2 | Cl | OMe | Br | |
| 2520 | 4-Ph | 2 | Cl | OMe | SO$_2$Me | |
| 2521 | 4-Ph | 2 | Cl | OEt | Br | |
| 2522 | 4-Ph | 2 | Br | H | OMe | |
| 2523 | 4-Ph | 2 | F | H | F | |
| 2524 | 4-Ph | 2 | I | I | I | |
| 2525 | 4-Ph | 2 | Me | H | CN | |
| 2526 | 4-Ph | 2 | Me | H | Me | |
| 2527 | 4-Ph | 2 | Me | H | OMe | |
| 2528 | 4-Ph | 2 | Me | Cl | Cl | |
| 2529 | 4-Ph | 2 | Me | CO$_2$Me | SO$_2$Me | |
| 2530 | 4-Ph | 2 | Me | CH$_2$OMe | SO$_2$Me | |
| 2531 | 4-Ph | 2 | Me | CH(Me)OMe | SO$_2$Me | |
| 2532 | 4-Ph | 2 | NO$_2$ | H | Cl | |
| 2533 | 4-Ph | 2 | NO$_2$ | H | Br | |
| 2534 | 4-Ph | 2 | NO$_2$ | H | F | |
| 2535 | 4-Ph | 2 | NO$_2$ | H | CN | |
| 2536 | 4-Ph | 2 | NO$_2$ | H | SMe | |
| 2537 | 4-Ph | 2 | NO$_2$ | H | CF$_3$ | |
| 2538 | 4-Ph | 2 | NO$_2$ | OMe | Cl | |
| 2539 | 4-Ph | 2 | NO$_2$ | OMe | CF$_3$ | |
| 2540 | 4-Ph | 2 | CF$_3$ | H | Cl | |
| 2541 | 4-Ph | 2 | CF$_3$ | H | Br | |
| 2542 | 4-Ph | 2 | CF$_3$ | H | SMe | |
| 2543 | 4-Ph | 2 | CF$_3$ | H | CF$_3$ | |
| 2544 | 4-Ph | 2 | OMe | H | Cl | |
| 2545 | 4-Ph | 2 | OMe | H | OMe | |
| 2546 | 5-Ph | 0 | Cl | H | Cl | |
| 2547 | 5-Ph | 0 | Cl | H | SO$_2$Me | |
| 2548 | 5-Ph | 0 | Cl | H | NO$_2$ | |
| 2549 | 5-Ph | 0 | Cl | H | OMe | |
| 2550 | 5-Ph | 0 | Cl | H | Me | |
| 2551 | 5-Ph | 0 | Cl | H | Br | |
| 2552 | 5-Ph | 0 | Cl | H | F | |
| 2553 | 5-Ph | 0 | Cl | H | SMe | |
| 2554 | 5-Ph | 0 | Cl | H | S(O)Me | |
| 2555 | 5-Ph | 0 | Cl | H | CF$_3$ | |
| 2556 | 5-Ph | 0 | Cl | H | CN | |
| 2557 | 5-Ph | 0 | Cl | Cl | Cl | |
| 2558 | 5-Ph | 0 | Cl | Cl | OMe | |
| 2559 | 5-Ph | 0 | Cl | Cl | SMe | |
| 2560 | 5-Ph | 0 | Cl | Cl | SO$_2$Me | |
| 2561 | 5-Ph | 0 | Cl | Me | Cl | |
| 2562 | 5-Ph | 0 | Cl | Me | SO$_2$Me | |
| 2563 | 5-Ph | 0 | Cl | OMe | Cl | |
| 2564 | 5-Ph | 0 | Cl | OMe | Br | |
| 2565 | 5-Ph | 0 | Cl | OMe | SO$_2$Me | |
| 2566 | 5-Ph | 0 | Cl | OEt | Br | |
| 2567 | 5-Ph | 0 | Br | H | OMe | |
| 2568 | 5-Ph | 0 | F | H | F | |

TABLE 2-continued

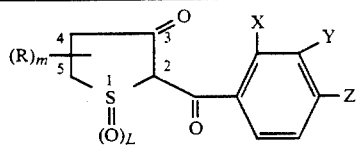

| Compound No. of the present invention | (R)$_m$ | L | X | Y | Z | Characteristic (Physical property) |
|---|---|---|---|---|---|---|
| 2569 | 5-Ph | 0 | I | I | I | |
| 2570 | 5-Ph | 0 | Me | H | CN | |
| 2571 | 5-Ph | 0 | Me | H | Me | |
| 2572 | 5-Ph | 0 | Me | H | OMe | |
| 2573 | 5-Ph | 0 | Me | Cl | Cl | |
| 2574 | 5-Ph | 0 | Me | CO$_2$Me | SO$_2$Me | |
| 2575 | 5-Ph | 0 | Me | CH$_2$OMe | SO$_2$Me | |
| 2576 | 5-Ph | 0 | Me | CH(Me)OMe | SO$_2$Me | |
| 2577 | 5-Ph | 0 | NO$_2$ | H | Cl | |
| 2578 | 5-Ph | 0 | NO$_2$ | H | Br | |
| 2579 | 5-Ph | 0 | NO$_2$ | H | F | |
| 2580 | 5-Ph | 0 | NO$_2$ | H | CN | |
| 2581 | 5-Ph | 0 | NO$_2$ | H | SMe | |
| 2582 | 5-Ph | 0 | NO$_2$ | H | CF$_3$ | |
| 2583 | 5-Ph | 0 | NO$_2$ | OMe | Cl | |
| 2584 | 5-Ph | 0 | NO$_2$ | OMe | CF$_3$ | |
| 2585 | 5-Ph | 0 | CF$_3$ | H | Cl | |
| 2586 | 5-Ph | 0 | CF$_3$ | H | Br | |
| 2587 | 5-Ph | 0 | CF$_3$ | H | SMe | |
| 2588 | 5-Ph | 0 | CF$_3$ | H | CF$_3$ | |
| 2589 | 5-Ph | 0 | OMe | H | Cl | |
| 2590 | 5-Ph | 0 | OMe | H | OMe | |
| 2591 | 5-Ph | 1 | Cl | H | Cl | |
| 2592 | 5-Ph | 1 | Cl | H | SO$_2$Me | |
| 2593 | 5-Ph | 1 | Cl | H | NO$_2$ | |
| 2594 | 5-Ph | 1 | Cl | H | OMe | |
| 2595 | 5-Ph | 1 | Cl | H | Me | |
| 2596 | 5-Ph | 1 | Cl | H | Br | |
| 2597 | 5-Ph | 1 | Cl | H | F | |
| 2598 | 5-Ph | 1 | Cl | H | SMe | |
| 2599 | 5-Ph | 1 | Cl | H | S(O)Me | |
| 2600 | 5-Ph | 1 | Cl | H | CF$_3$ | |
| 2601 | 5-Ph | 1 | Cl | H | CN | |
| 2602 | 5-Ph | 1 | Cl | Cl | Cl | |
| 2603 | 5-Ph | 1 | Cl | Cl | OMe | |
| 2604 | 5-Ph | 1 | Cl | Cl | SMe | |
| 2605 | 5-Ph | 1 | Cl | Cl | SO$_2$Me | |
| 2606 | 5-Ph | 1 | Cl | Me | Cl | |
| 2607 | 5-Ph | 1 | Cl | Me | SO$_2$Me | |
| 2608 | 5-Ph | 1 | Cl | OMe | Cl | |
| 2609 | 5-Ph | 1 | Cl | OMe | Br | |
| 2610 | 5-Ph | 1 | Cl | OMe | SO$_2$Me | |
| 2611 | 5-Ph | 1 | Cl | OEt | Br | |
| 2612 | 5-Ph | 1 | Br | H | OMe | |
| 2613 | 5-Ph | 1 | F | H | F | |
| 2614 | 5-Ph | 1 | I | I | I | |
| 2615 | 5-Ph | 1 | Me | H | CN | |
| 2616 | 5-Ph | 1 | Me | H | Me | |
| 2617 | 5-Ph | 1 | Me | H | OMe | |
| 2618 | 5-Ph | 1 | Me | Cl | Cl | |
| 2619 | 5-Ph | 1 | Me | CO$_2$Me | SO$_2$Me | |
| 2620 | 5-Ph | 1 | Me | CH$_2$OMe | SO$_2$Me | |
| 2621 | 5-Ph | 1 | Me | CH(Me)OMe | SO$_2$Me | |
| 2622 | 5-Ph | 1 | NO$_2$ | H | Cl | |
| 2623 | 5-Ph | 1 | NO$_2$ | H | Br | |
| 2624 | 5-Ph | 1 | NO$_2$ | H | F | |
| 2625 | 5-Ph | 1 | NO$_2$ | H | CN | |
| 2626 | 5-Ph | 1 | NO$_2$ | H | SMe | |
| 2627 | 5-Ph | 1 | NO$_2$ | H | CF$_3$ | |
| 2628 | 5-Ph | 1 | NO$_2$ | OMe | Cl | |
| 2629 | 5-Ph | 1 | NO$_2$ | OMe | CF$_3$ | |
| 2630 | 5-Ph | 1 | CF$_3$ | H | Cl | |
| 2631 | 5-Ph | 1 | CF$_3$ | H | Br | |
| 2632 | 5-Ph | 1 | CF$_3$ | H | SMe | |
| 2633 | 5-Ph | 1 | CF$_3$ | H | CF$_3$ | |
| 2634 | 5-Ph | 1 | OMe | H | Cl | |
| 2635 | 5-Ph | 1 | OMe | H | OMe | |
| 2636 | 5-Ph | 2 | Cl | H | Cl | |
| 2637 | 5-Ph | 2 | Cl | H | SO$_2$Me | |
| 2638 | 5-Ph | 2 | Cl | H | NO$_2$ | |
| 2639 | 5-Ph | 2 | Cl | H | OMe | |
| 2640 | 5-Ph | 2 | Cl | H | Me | |

TABLE 2-continued

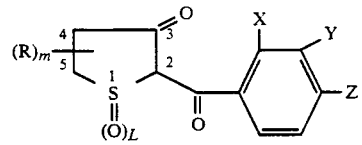

| Compound No. of the present invention | (R)$_m$ | L | X | Y | Z | Characteristic (Physical property) |
|---|---|---|---|---|---|---|
| 2641 | 5-Ph | 2 | Cl | H | Br | |
| 2642 | 5-Ph | 2 | Cl | H | F | |
| 2643 | 5-Ph | 2 | Cl | H | SMe | |
| 2644 | 5-Ph | 2 | Cl | H | S(O)Me | |
| 2645 | 5-Ph | 2 | Cl | H | CF$_3$ | |
| 2646 | 5-Ph | 2 | Cl | H | CN | |
| 2647 | 5-Ph | 2 | Cl | Cl | Cl | |
| 2648 | 5-Ph | 2 | Cl | Cl | OMe | |
| 2649 | 5-Ph | 2 | Cl | Cl | SMe | |
| 2650 | 5-Ph | 2 | Cl | Cl | SO$_2$Me | |
| 2651 | 5-Ph | 2 | Cl | Me | Cl | |
| 2652 | 5-Ph | 2 | Cl | Me | SO$_2$Me | |
| 2653 | 5-Ph | 2 | Cl | OMe | Cl | |
| 2654 | 5-Ph | 2 | Cl | OMe | Br | |
| 2655 | 5-Ph | 2 | Cl | OMe | SO$_2$Me | |
| 2656 | 5-Ph | 2 | Cl | OEt | Br | |
| 2657 | 5-Ph | 2 | Br | H | OMe | |
| 2658 | 5-Ph | 2 | F | H | F | |
| 2659 | 5-Ph | 2 | I | I | I | |
| 2660 | 5-Ph | 2 | Me | H | CN | |
| 2661 | 5-Ph | 2 | Me | H | Me | |
| 2662 | 5-Ph | 2 | Me | H | OMe | |
| 2663 | 5-Ph | 2 | Me | Cl | Cl | |
| 2664 | 5-Ph | 2 | Me | CO$_2$Me | SO$_2$Me | |
| 2665 | 5-Ph | 2 | Me | CH$_2$OMe | SO$_2$Me | |
| 2666 | 5-Ph | 2 | Me | CH(Me)OMe | SO$_2$Me | |
| 2667 | 5-Ph | 2 | NO$_2$ | H | Cl | |
| 2668 | 5-Ph | 2 | NO$_2$ | H | Br | |
| 2669 | 5-Ph | 2 | NO$_2$ | H | F | |
| 2670 | 5-Ph | 2 | NO$_2$ | H | CN | |
| 2671 | 5-Ph | 2 | NO$_2$ | H | SMe | |
| 2672 | 5-Ph | 2 | NO$_2$ | H | CF$_3$ | |
| 2673 | 5-Ph | 2 | NO$_2$ | OMe | Cl | |
| 2674 | 5-Ph | 2 | NO$_2$ | OMe | CF$_3$ | |
| 2675 | 5-Ph | 2 | CF$_3$ | H | Cl | |
| 2676 | 5-Ph | 2 | CF$_3$ | H | Br | |
| 2677 | 5-Ph | 2 | CF$_3$ | H | SMe | |
| 2678 | 5-Ph | 2 | CF$_3$ | H | CF$_3$ | |
| 2679 | 5-Ph | 2 | OMe | H | Cl | |
| 2680 | 5-Ph | 2 | OMe | H | OMe | |

TABLE 3

| Compound No. of the present invention | Dose (kg/ha) | EC | DI | CY | SO | GA | RO | ZE | TR |
|---|---|---|---|---|---|---|---|---|---|
| 1 | 0.5 | 5 | 5 | 5 | 5 | 5 | 5 | 0 | 0 |
| | 1.0 | 5 | 5 | 5 | 5 | 5 | 5 | 0 | 0 |
| | 2.0 | 5 | 5 | 5 | 5 | 5 | 5 | 0 | 0 |
| 7 | 1.0 | 5 | 5 | 5 | 5 | 5 | 5 | 0 | 0 |
| | 2.0 | 5 | 5 | 5 | 5 | 5 | 5 | 0 | 0 |
| 16 | 0.5 | 5 | 5 | 5 | 5 | 5 | 5 | 0 | 0 |
| | 1.0 | 5 | 5 | 5 | 5 | 5 | 5 | 0 | 0 |
| | 2.0 | 5 | 5 | 5 | 5 | 5 | 5 | 0 | 0 |
| 17 | 1.0 | 5 | 5 | 5 | 5 | 5 | 5 | 0 | 0 |
| | 2.0 | 5 | 5 | 5 | 5 | 5 | 5 | 0 | 0 |
| 29 | 1.0 | 5 | 5 | 5 | 5 | 5 | 5 | 0 | 0 |
| | 2.0 | 5 | 5 | 5 | 5 | 5 | 5 | 0 | 0 |
| 30 | 1.0 | 5 | 5 | 5 | 5 | 5 | 5 | 0 | 0 |
| | 2.0 | 5 | 5 | 5 | 5 | 5 | 5 | 0 | 0 |
| 32 | 1.0 | 5 | 5 | 5 | 5 | 5 | 5 | 0 | 0 |
| | 2.0 | 5 | 5 | 5 | 5 | 5 | 5 | 0 | 0 |
| 37 | 1.0 | 5 | 5 | 5 | 5 | 5 | 5 | 0 | 0 |
| | 2.0 | 5 | 5 | 5 | 5 | 5 | 5 | 0 | 0 |
| 1736 | 1.0 | 5 | 5 | 5 | 5 | 5 | 5 | 0 | 0 |
| | 2.0 | 5 | 5 | 5 | 5 | 5 | 5 | 0 | 0 |

TABLE 4

| Compound No. of the present invention | Dose (kg/ha) | EC | DI | CY | SO | GA | RO | ZE | TR |
|---|---|---|---|---|---|---|---|---|---|
| 1 | 0.5 | 5 | 5 | 5 | 5 | 5 | 5 | 0 | 0 |
| | 1.0 | 5 | 5 | 5 | 5 | 5 | 5 | 0 | 0 |
| | 2.0 | 5 | 5 | 5 | 5 | 5 | 5 | 0 | 0 |
| 7 | 1.0 | 5 | 5 | 5 | 5 | 5 | 5 | 0 | 0 |
| | 2.0 | 5 | 5 | 5 | 5 | 5 | 5 | 0 | 0* |
| 16 | 0.5 | 5 | 5 | 5 | 5 | 5 | 5 | 0 | 0 |
| | 1.0 | 5 | 5 | 5 | 5 | 5 | 5 | 0 | 0 |
| | 2.0 | 5 | 5 | 5 | 5 | 5 | 5 | 0 | 0 |
| 17 | 0.5 | 5 | 5 | 5 | 5 | 5 | 5 | 0 | 0 |
| | 1.0 | 5 | 5 | 5 | 5 | 5 | 5 | 0 | 0 |
| | 2.0 | 5 | 5 | 5 | 5 | 5 | 5 | 0 | 0 |
| 30 | 1.0 | 5 | 5 | 5 | 5 | 5 | 5 | 0 | 0 |
| | 2.0 | 5 | 5 | 5 | 5 | 5 | 5 | 0 | 0 |
| 32 | 1.0 | 5 | 5 | 5 | 5 | 5 | 5 | 0 | 0 |
| | 2.0 | 5 | 5 | 5 | 5 | 5 | 5 | 0 | 0 |
| 37 | 1.0 | 5 | 5 | 5 | 5 | 5 | 5 | 0 | 0 |
| | 2.0 | 5 | 5 | 5 | 5 | 5 | 5 | 0 | 0 |
| 1736 | 1.0 | 5 | 5 | 5 | 5 | 5 | 5 | 0 | 0 |
| | 2.0 | 5 | 5 | 5 | 5 | 5 | 5 | 0 | 0 |

What is claimed is:

1. A herbicidal composition, comprising:
a) a herbicidally effective amount of one or more benzoyl derivatives of the formula (I):

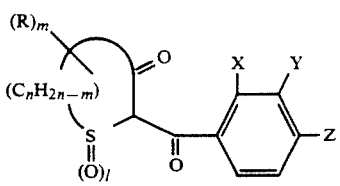 (I)

wherein

R is a lower alkyl group, or a phenyl group which is unsubstituted or substituted by a lower alkyl group, halogen atom or a lower alkoxy group;

n is an integer of 3;

m is an integer of from 0 to 6, and when m is an integer of from 2 to 6, the plurality of R is the same or different from one another;

l is an integer of 0, 1 or 2;

X is a halogen atom, a nitro group, a cyano group, a lower alkyl group, a lower alkoxy group, or a lower haloalkyl group;

Y is a hydrogen atom, halogen atom, a nitro group, a lower alkyl group which is unsubstituted or substituted by a halogen atom or a lower alkoxy group, a lower alkoxy group, or a lower alkoxycarbonyl group; and Z is a halogen atom, a nitro group, a cyano group, a trifluoromethyl group, a lower alkoxy group, a lower alkylthio group, a lower haloalkylthio group, a lower alkylsulfinyl group, a lower haloalkylsulfinyl group, a lower alkylsulfonyl group or a lower haloalkylsulfonyl group; and b) an agriculturally acceptable carrier.

2. The herbicidal composition of claim 1, wherein in the formula (I), Z is a halogen atom, a nitro group, a cyano group, a trifluoromethyl group, a lower alkoxy group, a lower alkylthio group or a lower alkylsulfonyl group.

3. The herbicidal composition of claim 1, wherein in the formula (I) m is an integer of 0 or 1; is an integer of 0 or 1; and Z is a halogen atom, nitro group, cyano group, trifluoromethyl group, lower alkoxy group, lower alkylthio group or a lower alkylsulfonyl group.

4. A herbicidal composition, comprising:
a) a herbicidally effective amount of one or more benzoyl derivatives of the formula:

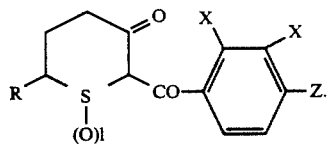

wherein

R is a hydrogen atom or a lower alkyl group;

l is an integer of 0 or 1;

X is a halogen atom or a nitro group;

Y is a hydrogen atom or a lower alkyl group; and

Z is a halogen atom or a trifluoromethyl group; and b) an agriculturally acceptable carrier.

5. A method of controlling weeds, which comprises applying a herbicidally effective amount of the composition of claim 1 to a locus to be protected.

6. A method of controlling weeds, which comprises applying a herbicidally effective amount of the composition of claim 4 to a locus to be protected.

* * * * *